(12) United States Patent
Nagamine et al.

(10) Patent No.: US 9,354,515 B2
(45) Date of Patent: May 31, 2016

(54) RESIST COMPOSITION, ACID GENERATOR, POLYMERIC COMPOUND AND METHOD OF FORMING RESIST PATTERN

(71) Applicant: Tokyo Ohka Kogyo Co., Ltd., Kawasaki-shi (JP)

(72) Inventors: Takashi Nagamine, Kawasaki (JP); Yoshitaka Komuro, Kawasaki (JP); Masatoshi Arai, Kawasaki (JP); Yoshiyuki Utsumi, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

(21) Appl. No.: 14/338,644

(22) Filed: Jul. 23, 2014

(65) Prior Publication Data

US 2015/0037734 A1 Feb. 5, 2015

(30) Foreign Application Priority Data

Jul. 31, 2013 (JP) .................................. 2013-159899

(51) Int. Cl.
| | | |
|---|---|---|
| *C07C 381/12* | (2006.01) | |
| *G03F 7/039* | (2006.01) | |
| *G03F 7/027* | (2006.01) | |
| *G03F 7/30* | (2006.01) | |
| *G03F 7/038* | (2006.01) | |
| *C08F 224/00* | (2006.01) | |

(52) U.S. Cl.
CPC .............. *G03F 7/027* (2013.01); *C07C 381/12* (2013.01); *C08F 224/00* (2013.01); *G03F 7/038* (2013.01); *G03F 7/30* (2013.01)

(58) Field of Classification Search
CPC ..... C07C 381/12; G03F 7/004; G03F 7/0045; G03F 7/039; G03F 7/0392; G03F 7/20
See application file for complete search history.

(56) References Cited

U.S. PATENT DOCUMENTS

| | | | |
|---|---|---|---|
| 6,111,143 A * | 8/2000 | Park et al. ....................... 568/35 | |
| 6,949,325 B2 | 9/2005 | Li et al. | |
| 2001/0049073 A1 | 12/2001 | Hada et al. | |
| 2003/0235775 A1 * | 12/2003 | Padmanaban et al. ...... 430/270.1 | |
| 2004/0110085 A1 | 6/2004 | Iwai et al. | |
| 2005/0042466 A1 * | 2/2005 | Ohno et al. ..................... 428/457 | |
| 2007/0149702 A1 * | 6/2007 | Ando et al. ..................... 524/556 | |
| 2009/0197204 A1 | 8/2009 | Shiono et al. | |
| 2009/0317743 A1 | 12/2009 | Shiono et al. | |
| 2010/0035185 A1 * | 2/2010 | Hagiwara et al. ........... 430/286.1 | |
| 2010/0055608 A1 * | 3/2010 | Ohashi et al. ............... 430/270.1 | |
| 2010/0310985 A1 | 12/2010 | Mori et al. | |
| 2011/0117499 A1 | 5/2011 | Matsumiya et al. | |
| 2011/0172191 A1 * | 7/2011 | Johnson et al. .................. 514/81 | |
| 2012/0184100 A1 * | 7/2012 | Yasuda et al. .................. 438/676 | |

FOREIGN PATENT DOCUMENTS

| | | |
|---|---|---|
| JP | A-2000-206694 | 7/2000 |
| JP | A-2003-241385 | 8/2003 |
| JP | A-2005-336452 | 12/2005 |
| JP | A-2006-259582 | 9/2006 |
| JP | A-2006-317803 | 11/2006 |
| JP | A-2009-025723 | 2/2009 |
| JP | A-2010-002870 | 1/2010 |
| JP | A-2010-032994 | 2/2010 |
| JP | A-2010-277043 | 9/2010 |
| JP | A-2011-013569 | 1/2011 |
| JP | A-2011-128226 | 6/2011 |

* cited by examiner

*Primary Examiner* — Anca Eoff
(74) *Attorney, Agent, or Firm* — Knobbe Martens Olson & Bear LLP

(57) ABSTRACT

A resist composition containing a compound represented by general formula (m0), wherein $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group; and $XO^-$ represents a monovalent organic anion.

(m0)

$$\begin{array}{c} R^3 \\ | \\ V^1 \\ | \\ R^1 \diagdown S^{\oplus} \diagup R^2 \end{array} \quad XO^{\ominus}$$

17 Claims, No Drawings

RESIST COMPOSITION, ACID GENERATOR, POLYMERIC COMPOUND AND METHOD OF FORMING RESIST PATTERN

TECHNICAL FIELD

The present invention relates to a resist composition, an acid generator, a polymeric compound and a method of forming a resist pattern.

Priority is claimed on Japanese Patent Application No. 2013-159899, filed Jul. 31, 2013, the content of which is incorporated herein by reference.

DESCRIPTION OF RELATED ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have led to rapid progress in the field of pattern miniaturization.

Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are starting to be introduced in mass production. Furthermore, research is also being conducted into lithography techniques that use an exposure light source having a wavelength shorter (energy higher) than these excimer lasers, such as electron beam, extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified composition is used, which includes a base material component that exhibits a changed solubility in a developing solution under the action of acid and an acid-generator component that generates acid upon exposure.

For example, in the case where the developing solution is an alkali developing solution (alkali developing process), a chemically amplified positive resist which contains, as a base component (base resin), a resin which exhibits increased solubility in an alkali developing solution under action of acid, and an acid generator is typically used. If a resist film formed using such a resist composition is selectively exposed at the time of forming a resist pattern, in exposed areas, an acid is generated from the acid generator component, and the polarity of the base resin increases by the action of the generated acid, thereby making the exposed areas soluble in the alkali developing solution. Thus, by conducting alkali developing, the unexposed portions remain to form a positive resist pattern. On the other hand, in the case of applying a solvent developing process using a developing solution containing an organic solvent (organic developing solution), when the polarity of the base resin increases, the solubility in the organic developing solution is relatively decreased. Therefore, unexposed areas of the resist film are dissolved in and removed by the organic developing solution, whereby a negative-type resist pattern in which exposed areas remain as a pattern is formed. Such a solvent developing process for forming a negative-tone resist composition is sometimes referred to as "negative-tone developing process" (for example, see Patent Document 1).

Currently, resins that contain structural units derived from (meth)acrylate esters within the main chain (acrylic resins) are now widely used as base resins for resist compositions that use ArF excimer laser lithography, as they exhibit excellent transparency in the vicinity of 193 nm (for example, see Patent Document 2).

On the other hand, as acid generators usable in a chemically amplified resist composition, various types have been proposed including, for example, onium salt acid generators; oxime sulfonate acid generators; diazomethane acid generators; nitrobenzylsulfonate acid generators; iminosulfonate acid generators; and disulfone acid generators.

DOCUMENTS OF RELATED ART

Patent Literature

[Patent Literature 1] Japanese Unexamined Patent Application, First Publication No. 2009-025723

[Patent Document 2] Japanese Unexamined Patent Application, First Publication No. 2003-241385

SUMMARY OF THE INVENTION

Due to further improvement in the performance and downsize of electronic devices, in the pattern formation in the production of semiconductor devices, further improvement in the lithography properties and the resist pattern shape are demanded. However, when a resist composition containing a conventional acid generator is used in the formation of a resist pattern, there was still room for improvement in various lithography properties.

The present invention takes the above circumstances into consideration, with an object of providing a compound useful as an acid generator for a resist composition, a resist composition containing the compound, and a method for forming a resist pattern using the resist composition.

For solving the above-mentioned problems, the present invention employs the following aspects.

Specifically, a first aspect of the present invention is a resist composition containing a compound represented by general formula (m0) shown below.

[Chemical Formula 1]

(m0)

In formula (m0), $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group; and $XO^-$ represents a monovalent organic anion.

A second aspect of the present invention is an acid generator including a compound represented by general formula (M1) shown below.

[Chemical Formula 2]

(M1)

In formula (M1), $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group; and $X^-$ represents a sulfonic acid anion, a carboxylic acid anion, an imide anion or a methide anion.

A third aspect of the present invention is a polymeric compound including an anion group which generates acid upon exposure on a side chain of the polymeric compound, and a structural unit (am0) having a cation moiety containing a cation represented by general formula (m1) shown below.

[Chemical Formula 3]

(m1)

In formula (m1), $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group.

A fourth aspect of the present invention is a method of forming a resist pattern, including: using a resist composition according to the first aspect to form a resist film on a substrate, exposing the resist film, and developing the exposed resist film to form a resist pattern.

According to the present invention, there are provided a compound useful as an acid generator for a resist composition, a resist composition containing the compound, and a method for forming a resist pattern using the resist composition.

DETAILED DESCRIPTION OF THE INVENTION

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified. The same applies for the alkyl group within an alkoxy group.

The term "alkylene group" includes linear, branched or cyclic, divalent saturated hydrocarbon, unless otherwise specified.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group have been substituted with a fluorine atom.

The term "structural unit" refers to a monomer unit that contributes to the formation of a polymeric compound (resin, polymer, copolymer).

The expression "may have a substituent" means that a case where a hydrogen atom (—H) is substituted with a monovalent group, or a case where a methylene (—CH$_2$—) group is substituted with a divalent group.

The term "exposure" is used as a general concept that includes irradiation with any form of radiation.

A "structural unit derived from an acrylate ester" refers to a structural unit that is formed by the cleavage of the ethylenic double bond of an acrylate ester.

An "acrylate ester" refers to a compound in which the terminal hydrogen atom of the carboxy group of acrylic acid (CH$_2$=CH—COOH) has been substituted with an organic group.

The acrylate ester may have the hydrogen atom bonded to the carbon atom on the α-position substituted with a substituent. The substituent ($R^{\alpha 0}$) that substitutes the hydrogen atom bonded to the carbon atom on the α-position is an atom other than hydrogen or a group, and examples thereof include an alkyl group of 1 to 5 carbon atoms and a halogenated alkyl group of 1 to 5 carbon atoms. Further, an acrylate ester having the hydrogen atom bonded to the carbon atom on the α-position substituted with a substituent ($R^{\alpha 0}$) in which the substituent has been substituted with a substituent containing an ester bond (e.g., an itaconic acid diester), or an acrylic acid having the hydrogen atom bonded to the carbon atom on the α-position substituted with a substituent ($R^{\alpha 0}$) in which the substituent has been substituted with a hydroxyalkyl group or a group in which the hydroxy group within a hydroxyalkyl group has been modified (e.g., α-hydroxyalkyl acrylate ester) can be mentioned as an acrylate ester having the hydrogen atom bonded to the carbon atom on the α-position substituted with a substituent. A carbon atom on the α-position of an acrylate ester refers to the carbon atom bonded to the carbonyl group, unless specified otherwise.

Hereafter, an acrylate ester having the hydrogen atom bonded to the carbon atom on the α-position substituted with a substituent is sometimes referred to as "α-substituted acrylate ester". Further, acrylate esters and α-substituted acrylate esters are collectively referred to as "(α-substituted) acrylate ester".

A "structural unit derived from acrylaminde" refers to a structural unit that is formed by the cleavage of the ethylenic double bond of acrylaminde.

The acrylamide may have the hydrogen atom bonded to the carbon atom on the α-position substituted with a substituent, and may have either or both terminal hydrogen atoms on the amino group of acrylamide substituted with a substituent. A carbon atom on the α-position of an acrylamide refers to the carbon atom bonded to the carbonyl group, unless specified otherwise.

As the substituent which substitutes the hydrogen atom on the α-position of acrylamide, the same substituents as those described above for the substituent ($R^{\alpha 0}$) on the α-position of the aforementioned α-position of the aforementioned α-substituted acrylate ester can be mentioned.

A "structural unit derived from hydroxystyrene or a hydroxystyrene derivative" refers to a structural unit that is formed by the cleavage of the ethylenic double bond of hydroxystyrene or a hydroxystyrene derivative.

The term "hydroxystyrene derivative" includes compounds in which the hydrogen atom at the α-position of hydroxystyrene has been substituted with another substituent such as an alkyl group or a halogenated alkyl group; and derivatives thereof. Examples of the derivatives thereof include hydroxystyrene in which the hydrogen atom of the hydroxy group has been substituted with an organic group and may have the hydrogen atom on the α-position substituted with a substituent; and hydroxystyrene which has a substituent other than a hydroxy group bonded to the benzene ring and may have the hydrogen atom on the α-position substituted with a substituent. Here, the α-position (carbon atom on the α-position) of hydroxystyrene refers to the carbon atom having the benzene ring bonded thereto, unless specified otherwise.

As the substituent which substitutes the hydrogen atom on the α-position of hydroxystyrene, the same substituents as those described above for the substituent on the α-position of the aforementioned α-substituted acrylate ester can be mentioned.

A "structural unit derived from vinylbenzoic acid or a vinylbenzoic acid derivative" refers to a structural unit that is formed by the cleavage of the ethylenic double bond of vinylbenzoic acid or a vinylbenzoic acid derivative.

The term "vinylbenzoic acid derivative" includes compounds in which the hydrogen atom at the α-position of vinylbenzoic acid has been substituted with another substituent such as an alkyl group or a halogenated alkyl group; and derivatives thereof. Examples of the derivatives thereof include benzoic acid in which the hydrogen atom of the carboxy group has been substituted with an organic group and may have the hydrogen atom on the α-position substituted with a substituent; and benzoic acid which has a substituent other than a hydroxy group and a carboxy group bonded to the benzene ring and may have the hydrogen atom on the α-position substituted with a substituent. Here, the α-position (carbon atom on the α-position) of vinylbenzoic acid refers to the carbon atom having the benzene ring bonded thereto, unless specified otherwise.

The term "styrene" is a concept including styrene and compounds in which the hydrogen atom at the α-position of styrene is substituted with other substituent such as an alkyl group and a halogenated alkyl group.

A "structural unit derived from styrene" or "structural unit derived from a styrene derivative" refers to a structural unit that is formed by the cleavage of the ethylenic double bond of styrene or a styrene derivative.

As the alkyl group as a substituent on the α-position, a linear or branched alkyl group is preferable, and specific examples include alkyl groups of 1 to 5 carbon atoms, such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group as the substituent on the α-position include groups in which part or all of the hydrogen atoms of the aforementioned "alkyl group as the substituent on the α-position" are substituted with halogen atoms. Examples of the halogen atom include a fluorine atom, a chlorine atom, a bromine atom and an iodine atom, and a fluorine atom is particularly desirable.

Specific examples of the hydroxyalkyl group of 1 to 5 carbon atoms as the substituent on the α-position include groups in which part or all of the hydrogen atoms of the aforementioned "alkyl group as the substituent on the α-position" are substituted with a hydroxy group. The number of hydroxy groups within the hydroxyalkyl group is preferably 1 to 5, and most preferably 1.

<<Resist Composition>>

The resist composition according to a first aspect of the present invention includes a compound represented by general formula (m0) shown below (hereafter, this compound is sometimes referred to as "compound (m0)").

[Chemical Formula 4]

(m0)

In formula (m0), $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group; and $X0^-$ represents a monovalent organic anion.

In formula (m0) above, $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom.

Examples of the aryl group for $R^1$ and $R^2$ include an unsubstituted aryl group of 6 to 20 carbon atoms, and a phenyl group or a naphthyl group is preferable.

As the alkyl group for $R^1$ and $R^2$, a chain-like alkyl group of 1 to 30 carbon atoms or a cyclic alkyl group of 3 to 30 carbon atoms is preferable.

The alkenyl group for $R^1$ and $R^2$ preferably has 2 to 10 carbon atoms.

Specific examples of the substituent for $R^1$ and $R^2$ include an alkyl group, a halogen atom, a halogenated alkyl group, an alkoxy group, a carbonyl group, a cyano group, an amino group, an aryl group, an arylthio group and groups represented by general formulae (ca-r-1) to (ca-r-7) described later. Examples of the arylthio group as the substituent include a phenylthio group and a biphenylthio group.

$R^1$ and/or $R^2$ may have one substituent, or two or more substituents.

When $R^1$ and $R^2$ are mutually bonded to form a ring with the sulfur atom, these groups may be mutually bonded via a hetero atom such as a sulfur atom, an oxygen atom or a nitrogen atom, or a functional group such as a carbonyl group, —SO—, —SO$_2$—, —SO$_3$—, —COO—, —CONH— or —N(R$_N$)— (wherein R$_N$ represents an alkyl group of 1 to 5 carbon atoms). The ring containing the sulfur atom in the skeleton thereof is preferably a 3 to 10-membered ring, and most preferably a 5 to 7-membered ring. Specific examples of the ring formed include a thiophene ring, a thiazole ring, a benzothiophene ring, a thianthrene ring, a benzothiophene ring, a dibenzothiophene ring, a 9H-thioxanthene ring, a thioxanthone ring, a phenoxathiin ring, a tetrahydrothiophenium ring, and a tetrahydrothiopyranium ring.

In formula (m0), $R^3$ represents an aromatic hydrocarbon group which may have a substituent, an alkenyl group which may have a substituent, or an alkynyl group which may have a substituent.

The aromatic hydrocarbon group for $R^3$ is a hydrocarbon group having at least one aromatic ring.

The aromatic ring is not particularly limited, as long as it is a cyclic conjugated compound having (4n+2)π electrons, and may be either monocyclic or polycyclic. The aromatic ring preferably has 5 to 30 carbon atoms, more preferably 5 to 20, still more preferably 6 to 15, and most preferably 6 to 12. Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group for $R^3$ include a group in which one hydrogen atom has been removed from the aforementioned aromatic hydrocarbon ring or aromatic hetero ring (aryl group or heteroaryl group); a group in which one hydrogen atom has been removed from an aromatic compound having two or more aromatic rings (biphenyl, fluorene or the like).

The alkenyl group for $R^3$ may be linear or branched, and preferably has 2 to 10 carbon atoms, more preferably 2 to 5 carbon atoms, still more preferably 2 to 4 carbon atoms, and most preferably 2 carbon atoms. Examples of linear alkenyl groups include a vinyl group, a propenyl group (an allyl group) and a butynyl group. Examples of branched alkenyl groups include a 1-methylvinyl group, a 2-methylvinyl group, a 1-methylpropenyl group and a 2-methylpropenyl group. Among these examples, a linear alkenyl group is preferable, a vinyl group or a propenyl group is more preferable, and a vinyl group is most preferable.

Examples of the alkynyl group for $R^3$ include an ethynyl group (CH≡C—) and a propargyl group (CH≡CCH$_2$—).

Examples of the substituent for $R^3$ include the same substituents as those described above for $R^1$ and $R^2$.

$R^3$ may have one substituent, or two or more substituents.

In formula (m0), $V^1$ represents a single bond or an alkylene group.

The alkylene group for $V^1$ is preferably an alkylene group of 1 to 5 carbon atoms, more preferably an alkylene group of 1 to 3 carbon atoms, and still more preferably a methylene group (—CH$_2$—) or an ethylene group (—CH$_2$CH$_2$—).

However, when $R^3$ is an aromatic hydrocarbon group which may have a substituent, $V^1$ is an alkylene group. In such a case, when $V^1$ is a single bond, it becomes difficult to obtain improvement in the lithography properties and the pattern shape in the formation of a resist pattern.

Specific examples of the cation moiety of the compound represented by general formula (m0) are shown below.

[Chemical Formula 5]

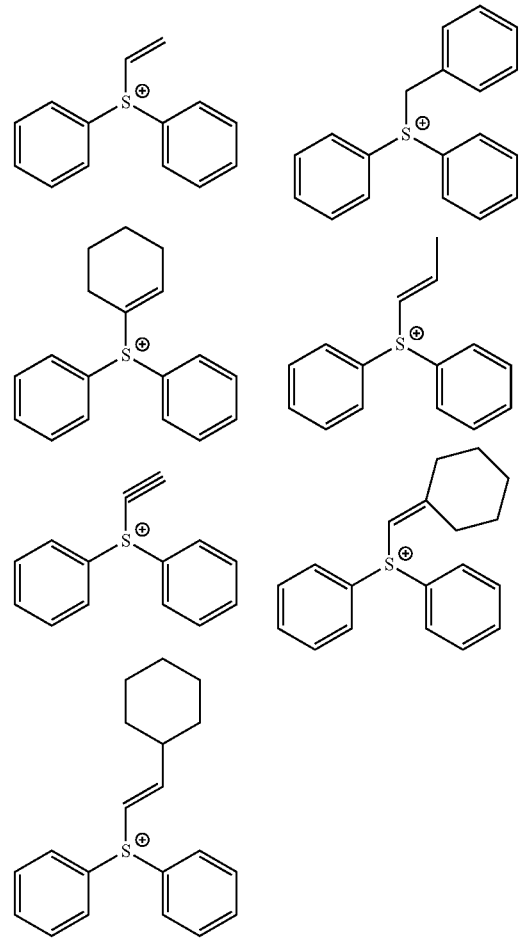

In formula (m0), X0$^-$ represents a monovalent organic anion.

Examples of the monovalent organic anion for X0$^-$ include a sulfonic acid anion, a carboxylic acid anion, an imide anion and a methide anion. Specifically, for example, the same anions as those defined for the anion of compounds represented by any of general formulae (b-1) to (b-3) and (d1-1) to (d1-3) described later, an organic anion represented by any of general formulae (am0-1-1) to (am0-1-3) described later, and an organic anion represented by any of general formulae (am0-2-1) to (am0-2-3) described later can be mentioned.

In the resist composition according to the first aspect of the present embodiment, the amount of the compound (m0) is not particularly limited, and can be appropriately adjusted depending on the desired properties of the resist composition.

The compound (m0) described above capable of being decomposed upon exposure to generate acid. In addition, the compound (m0) is more likely to have the cation moiety decomposed upon exposure than a triphenylsulfonium compound. By using a resist composition containing the compound (m0), the generation efficiency of acid in the formation of a resist pattern is improved. Therefore, according to the resist composition of the present embodiment, sensitivity is improved in the formation of a resist pattern, various lithography properties such as exposure latitude, mask reproducibility and reduction of roughness are improved, and a resist pattern with an excellent shape can be formed. Furthermore, even in the case where the compound (m0) is used as acid diffusion control agent, due to the high decomposition efficiency by exposure, the effect of enhancing the sensitivity can be achieved.

Preferable examples of the resist composition according to the present aspect include the following resist compositions of the first to third embodiments.

<Resist Composition of First Embodiment>

The resist composition of the first embodiment (hereafter, sometimes referred to as "first resist composition") includes a base component (A) (hereafter, referred to as "component (A)") which exhibits changed solubility in a developing solution under action of acid, and an acid-generator component (B) (hereafter, sometimes referred to as "component (B)") which generates acid upon exposure. Further, the component (B) includes a compound represented by general formula (b0) described later.

When a resist film is formed using the first resist composition and the formed resist film is subjected to a selective exposure, acid is generated from the component (B) at exposed portions, and the generated acid acts on the component (A) to change the solubility of the component (A) in a developing solution, whereas the solubility of the component (A) in a developing solution is not changed at unexposed portions, thereby generating difference in solubility in a developing solution between exposed portions and unexposed portions. Therefore, by subjecting the resist film to development, the exposed portions are dissolved and removed to form a positive-tone resist pattern in the case of a positive resist, whereas the unexposed portions are dissolved and removed to form a negative-tone resist pattern in the case of a negative resist.

In the present specification, a resist composition which forms a positive resist pattern by dissolving and removing the exposed portions is called a positive resist composition, and a resist composition which forms a negative resist pattern by dissolving and removing the unexposed portions is called a negative resist composition.

The first resist composition may be either a positive resist composition or a negative resist composition. Further, in the formation of a resist pattern, the first resist composition can be applied to an alkali developing process using an alkali developing solution in the developing treatment, or a solvent developing process using a developing solution containing an organic solvent (organic developing solution) in the developing treatment.

[Component (A)]

The component (A) is a base component which exhibits changed solubility in a developing solution under action of acid.

In the present invention, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compound used as the base component is broadly classified into non-polymers and polymers.

In general, as a non-polymer, any of those which have a molecular weight in the range of 500 to less than 4,000 is used. Hereafter, a "low molecular weight compound" refers to a non-polymer having a molecular weight in the range of 500 to less than 4,000.

As a polymer, any of those which have a molecular weight of 1,000 or more is generally used. Hereafter, a "resin" refers to a polymer having a molecular weight of 1,000 or more.

As the molecular weight of the polymer, the weight average molecular weight in terms of the polystyrene equivalent value determined by gel permeation chromatography (GPC) is used.

As the component (A'), a resin, a low molecular weight compound, or a combination thereof may be used.

The component (A) may be a resin that exhibits increased solubility in a developing solution under action of acid or a resin that exhibits decreased solubility in a developing solution under action of acid.

When the first resist composition is a "negative resist composition for alkali developing process" that forms a negative-tone resist pattern in an alkali developing process (or a "positive resist composition for solvent developing process" that forms a positive-tone resist pattern in a solvent developing process), as the component (A), a base component (A-2) that is soluble in an alkali developing solution (hereafter, this base component is sometimes referred to as "component (A-2)") is preferably used, and a cross-linking component is further added. In such a resist composition, when acid is generated from the component (B) upon exposure, the action of the acid causes cross-linking between the component (A-2) and the cross-linking component. As a result, the solubility of the resist composition in an alkali developing solution is decreased (the solubility of the resist composition in an organic developing solution is increased). Therefore, in the formation of a resist pattern, by conducting selective exposure of a resist film formed by applying the resist composition to a substrate, the exposed portions become insoluble in an alkali developing solution (soluble in an organic developing solution), whereas the unexposed portions remain soluble in an alkali developing solution (insoluble in an organic developing solution), and hence, a negative resist pattern is formed by conducting development using an alkali developing solution. Alternatively, in such a case, by developing using an organic developing solution, a positive resist pattern is formed.

As the component (A-2), a resin that is soluble in an alkali developing solution (hereafter, referred to as "alkali-soluble resin") is used.

Examples of the alkali soluble resin include a resin having a structural unit derived from at least one of α-(hydroxyalkyl)acrylic acid and an alkyl ester of α-(hydroxyalkyl)acrylic acid (preferably an alkyl ester having 1 to 5 carbon atoms), as disclosed in Japanese Unexamined Patent Application, First Publication No. 2000-206694; an acrylic resin which has a sulfonamide group and may have the hydrogen atom bonded to the carbon atom on the α-position substituted with a substituent or polycycloolefin resin having a sulfoneamide group, as disclosed in U.S. Pat. No. 6,949,325; an acrylic resin which may have the hydrogen atom bonded to the carbon atom on the α-position substituted with a substituent and having a fluorinated alcohol, as disclosed in U.S. Pat. No. 6,949,325, Japanese Unexamined Patent Application, First Publication No. 2005-336452 or Japanese Unexamined Patent Application, First Publication No. 2006-317803; and a polycyclolefin resin having a fluorinated alcohol, as disclosed in Japanese Unexamined Patent Application, First Publication No. 2006-259582. These resins are preferable in that a resist pattern can be formed with minimal swelling.

Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group, or a melamine-based cross-linking agent is preferable, as it enables formation of a resist pattern with minimal swelling. The amount of the cross-linker added is preferably within a range from 1 to 50 parts by weight, relative to 100 parts by weight of the alkali-soluble resin.

In the case where the resist composition of the present invention is a resist composition which forms a positive pattern in an alkali developing process (i.e, a positive resist compound for alkali developing process) or a resist composition which forms a negative pattern in a solvent developing process (i.e., a negative type resist composition for solvent developing process), as a component (A), it is preferable to use a base component (A-1) (hereafter, referred to as "component (A-1)") which exhibits increased polarity by the action of acid. By using the component (A-1), since the polarity of the base component changes prior to and after exposure, an excellent development contrast can be obtained not only in an alkali developing process, but also in a solvent developing process.

More specifically, in the case of applying an alkali developing process, the component (A-1) is substantially insoluble in an alkali developing solution prior to exposure, but when acid is generated upon exposure, the action of this acid causes an increase in the polarity of the base component, thereby increasing the solubility of the component (A-1) in an alkali developing solution. Therefore, in the formation of a resist pattern, by conducting selective exposure of a resist film formed by applying the resist composition to a substrate, the exposed portions change from an insoluble state to a soluble state in an alkali developing solution, whereas the unexposed portions remain insoluble in an alkali developing solution, and hence, a positive resist pattern is formed by alkali developing.

On the other hand, in the case of a solvent developing process, the component (A-1) exhibits high solubility in an organic developing solution prior to exposure, and when acid is generated upon exposure, the polarity of the component (A-1) is increased by the action of the generated acid, thereby decreasing the solubility of the component (A-1) in an organic developing solution. Therefore, in the formation of a resist pattern, by conducting selective exposure of a resist film formed by applying the resist composition to a substrate, the exposed portions changes from an soluble state to an insoluble state in an organic developing solution, whereas the unexposed portions remain soluble in an organic developing solution. As a result, by conducting development using an organic developing solution, a contrast can be made between the exposed portions and unexposed portions, thereby forming a negative resist pattern.

In the first resist composition, the component (A) is preferably a component (A-1).

In the case where the component (A) is a component (A-1), the component (A-1) preferably includes a polymeric compound (A1) (hereafter, referred to as "component (A1)") which has a structural unit (a1) containing an acid decomposable group that exhibits increased polarity by the action of acid.

As the component (A1), It is preferable to use a polymeric compound having, in addition to the structural unit (a1), a structural unit (a2) containing a lactone-containing cyclic group, an $_2$-containing cyclic group, or a carbonate-containing cyclic group.

Further, as the component (A1), it is preferable to use a polymeric compound having, in addition to the structural unit (a1), or in addition to the structural unit (a1) and the structural unit (a2), a structural unit (a3) containing a polar group (provided that structural units which fall under the definition of the structural unit (a1) or the structural unit (a2) are excluded).

(Structural Unit (a1))

The structural unit (a1) is a structural unit containing an acid decomposable group that exhibits increased polarity by the action of acid.

The term "acid decomposable group" refers to a group in which at least a part of the bond within the structure thereof is cleaved by the action of an acid.

Examples of acid decomposable groups which exhibit increased polarity by the action of an acid include groups which are decomposed by the action of an acid to form a polar group.

Examples of the polar group include a carboxy group, a hydroxy group, an amino group and a sulfo group ($—SO_3H$). Among these, a polar group containing —OH in the structure thereof (hereafter, referred to as "OH-containing polar group") is preferable, a carboxy group or a hydroxy group is more preferable, and a carboxy group is particularly desirable.

More specifically, as an example of an acid decomposable group, a group in which the aforementioned polar group has been protected with an acid dissociable group (such as a group in which the hydrogen atom of the OH-containing polar group has been protected with an acid dissociable group) can be given.

Here, the "acid dissociable group" includes:

(i) a group in which the bond between the acid dissociable group and the adjacent atom is cleaved by the action of acid; and (ii) a group in which one of the bonds is cleaved by the action of acid, and then a decarboxylation reaction occurs, thereby cleaving the bond between the acid dissociable group and the adjacent atom.

It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire component (A1) is increased. By the increase in the polarity, the solubility in an alkali developing solution changes, and the solubility in an alkali developing solution is relatively increased, whereas the solubility in an organic developing solution is relatively decreased.

The acid dissociable group is not particularly limited, and any of the groups that have been conventionally proposed as acid dissociable groups for the base resins of chemically amplified resists can be used.

Examples of the acid dissociable group for protecting the carboxy group or hydroxy group as a polar group include the acid dissociable group represented by general formula (a1-r-

1) shown below (hereafter, for the sake of convenience, sometimes referred to as "acetal-type acid dissociable group").

[Chemical Formula 6]

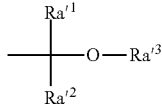

(a1-r-1)

In the formula, $Ra'^1$ and $Ra'^2$ represents a hydrogen atom or an alkyl group; and $Ra'^3$ represents a hydrocarbon group, provided that $Ra'^3$ may be bonded to $Ra'^1$ or $Ra'^2$.

In formula (a1-r-1), as the lower alkyl group for $Ra'^1$ and $Ra'^2$, the same lower alkyl groups as those described above the alkyl groups as the substituent which may be bonded to the carbon atom on the α-position of the aforementioned α-substituted alkylester can be used, although a methyl group or ethyl group is preferable, and a methyl group is particularly desirable.

The hydrocarbon group for $Ra'^3$ is preferably an alkyl group of 1 to 20 carbon atoms, more preferably an alkyl group of 1 to 10 carbon atoms, and still more preferably a linear or branched alkyl group. Specific examples thereof include a methyl group, an ethyl group, a propyl group, an isopropyl group, an n-butyl group, an isobutyl group, a tert-butyl group, a pentyl group, an isopentyl group, a neopentyl group, a 1,1-dimethylethyl group, a 1,1-diethylpropyl group, a 2,2-dimethylpropyl group and a 2,2-dimethylbutyl group.

In the case where $Ra'^3$ represents a cyclic hydrocarbon group, the cyclic hydrocarbon group may be aliphatic or aromatic, and may be polycyclic or monocyclic. As the monocyclic aliphatic hydrocarbon group, a group in which 1 hydrogen atom has been removed from a monocycloalkane is preferable. The monocycloalkane preferably has 3 to 8 carbon atoms, and specific examples thereof include cyclopentane, cyclohexane and cyclooctane. As the polycyclic group, a group in which 1 hydrogen atom has been removed from a polycycloalkane is preferable, and the polycyclic group preferably has 7 to 12 carbon atoms. Examples of the polycycloalkane include adamantane, norbornane, isobornane, tricyclodecane and tetracyclododecane.

In the case where the hydrocarbon group is an aromatic hydrocarbon group, examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which 1 hydrogen atom has been removed from the aforementioned aromatic hydrocarbon ring (aryl group); and a group in which 1 hydrogen atom of the aforementioned aryl group has been substituted with an alkylene group (an arylalkyl group such as a benzyl group, a phenethyl group, a 1-naphthylmethyl group, a 2-naphthylmethyl group, a 1-naphthylethyl group or a 2-naphthylethyl group). The alkylene group (alkyl chain within the arylalkyl group) preferably has 1 to 4 carbon atom, more preferably 1 or 2, and most preferably 1.

In the case where $Ra'^3$ is bonded to $Ra'^1$ or $Ra'^2$ to form a ring, the cyclic group is preferably a 4 to 7-membered ring, and more preferably a 4 to 6-membered ring. Specific examples of the cyclic group include tetrahydropyranyl group and tetrahydrofuranyl group.

Examples of the acid dissociable group for protecting the carboxy group as a polar group include the acid dissociable group represented by general formula (a1-r-2) shown below (hereafter, with respect to the acid dissociable group represented by the following formula (a1-r-2), the acid dissociable group constituted of alkyl groups is referred to as "tertiary ester-type acid dissociable group").

[Chemical Formula 7]

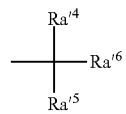

(a1-r-2)

In the formula, $Ra'^4$ to $Ra'^6$ each independently represents a hydrocarbon group, provided that $Ra'^5$ and $Ra'^6$ may be mutually bonded to form a ring.

As the hydrocarbon group for $Ra'^4$ to $Ra'^6$, the same groups as those described above for $Ra'^3$ can be mentioned.

$Ra'^4$ is preferably an alkyl group of 1 to 5 carbon atoms. In the case where $Ra'^5$ and $Ra'^6$ are mutually bonded to form a ring, a group represented by general formula (a1-r2-1) shown below can be mentioned.

On the other hand, in the case where $Ra'^4$ to $Ra'^6$ are not mutually bonded and independently represent a hydrocarbon group, the group represented by general formula (a1-r2-2) shown below can be mentioned.

[Chemical Formula 8]

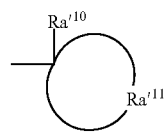

(a1-r2-1)

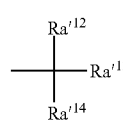

(a1-r2-2)

In the formulae, $Ra'^{10}$ represents an alkyl group of 1 to 10 carbon atoms; $Ra'^{11}$ is a group which forms an aliphatic cyclic group together with a carbon atom having $Ra'^{10}$ bonded thereto; $Ra'^{12}$ to $Ra'^{14}$ each independently represents a hydrocarbon group.

In the formula (a1-r2-1), as the alkyl group of 1 to 10 carbon atoms for $Ra'^{10}$, the same groups as described above for the linear or branched alkyl group for $Ra'^3$ in the formula (a1-r-1) are preferable. In the formula (a1-r2-1), as the aliphatic cyclic group which is formed by $Ra'^{11}$, the same groups as those described above for the cyclic alkyl group for $Ra'^3$ in the formula (a1-r-1) are preferable.

In the formula (a1-r2-2), it is preferable that $Ra'^{12}$ and $Ra'^{14}$ each independently represents an alkyl group or 1 to 10 carbon atoms, and it is more preferable that the alkyl group is the same group as the described above for the linear or branched alkyl group for $Ra'^3$ in the formula (a1-r-1), it is still more preferable that the alkyl group is a linear alkyl group of 1 to 5 carbon atoms, and it is particularly preferable that the alkyl group is a methyl group or an ethyl group.

In the formula (a1-r2-2), it is preferable that Ra'^13 is the same group as described above for the linear, branched or cyclic alkyl group for Ra'^3 in the formula (a1-r-1).

Among these, the same cyclic alkyl group as those describe above for Ra'^3 is more preferable.

Specific examples of the group represented by the aforementioned formula (a1-r2-1) are shown below. In the formulae below, "*" represents a valence bond (the same applies hereafter).

[Chemical Formula 9]

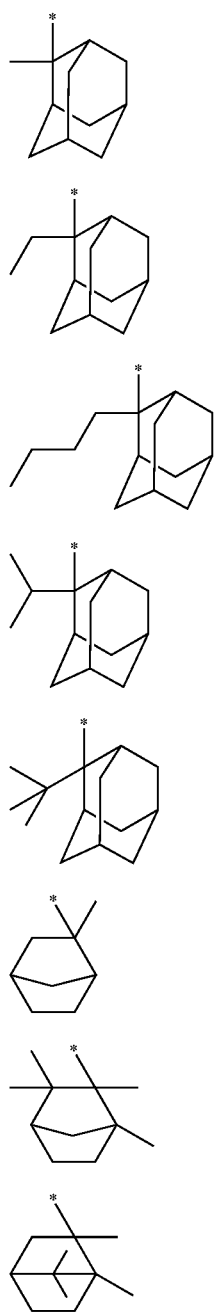

(r-pr-m1)

(r-pr-m2)

(r-pr-m3)

(r-pr-m4)

(r-pr-m5)

(r-pr-m6)

(r-pr-m7)

(r-pr-m8)

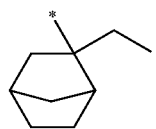

(r-pr-m9)

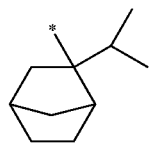

(r-pr-m10)

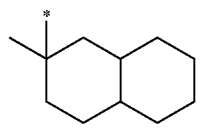

(r-pr-m11)

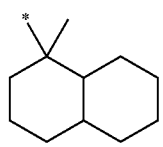

(r-pr-m12)

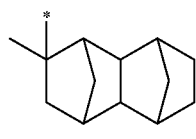

(r-pr-m13)

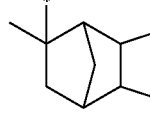

(r-pr-m14)

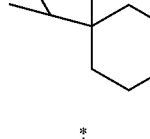

(r-pr-m15)

(r-pr-m16)

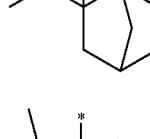

(r-pr-m17)

(r-pr-s1)

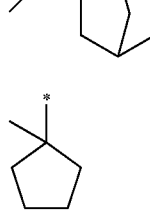

(r-pr-s2)

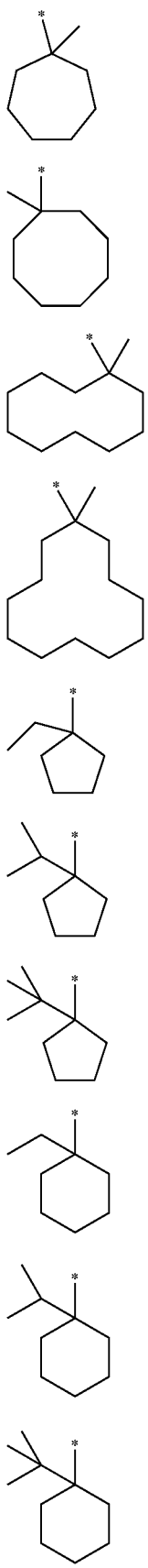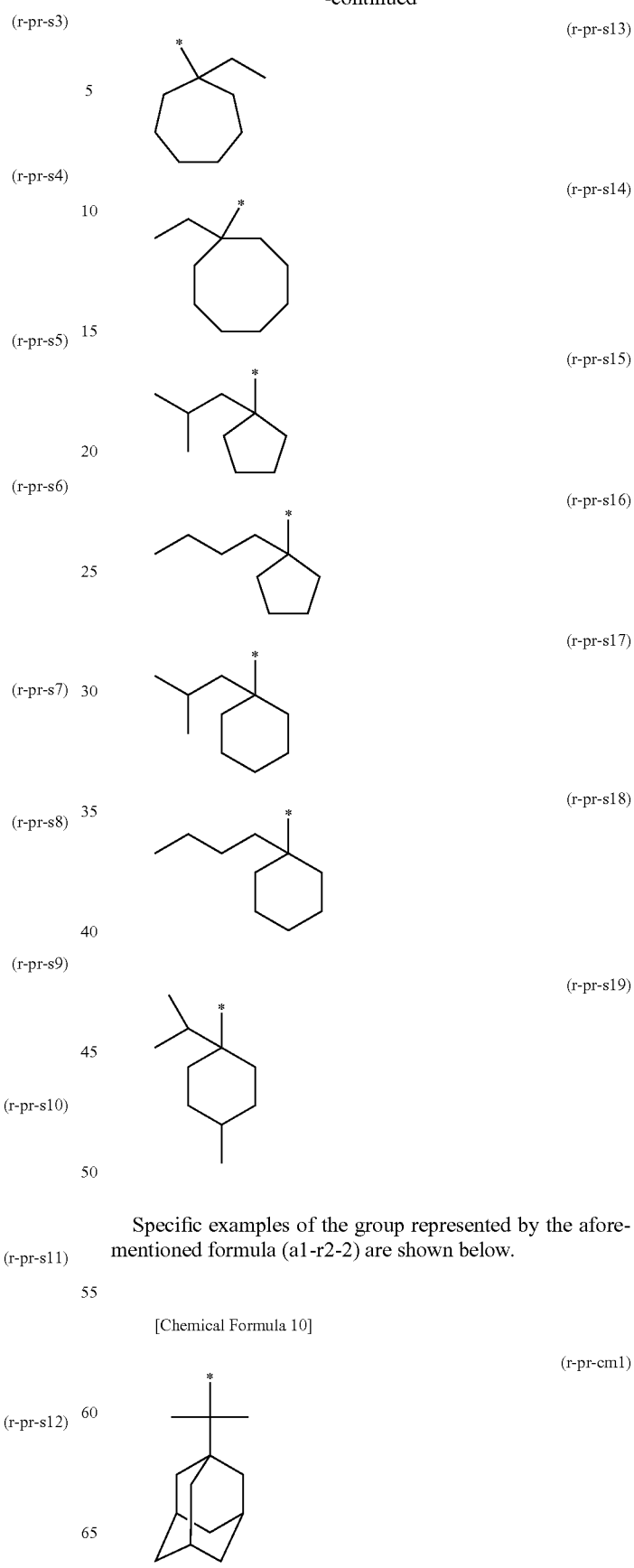
Specific examples of the group represented by the aforementioned formula (a1-r2-2) are shown below.
[Chemical Formula 10]

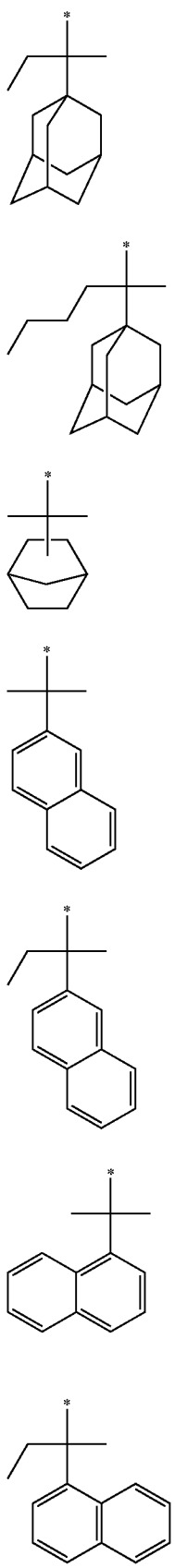
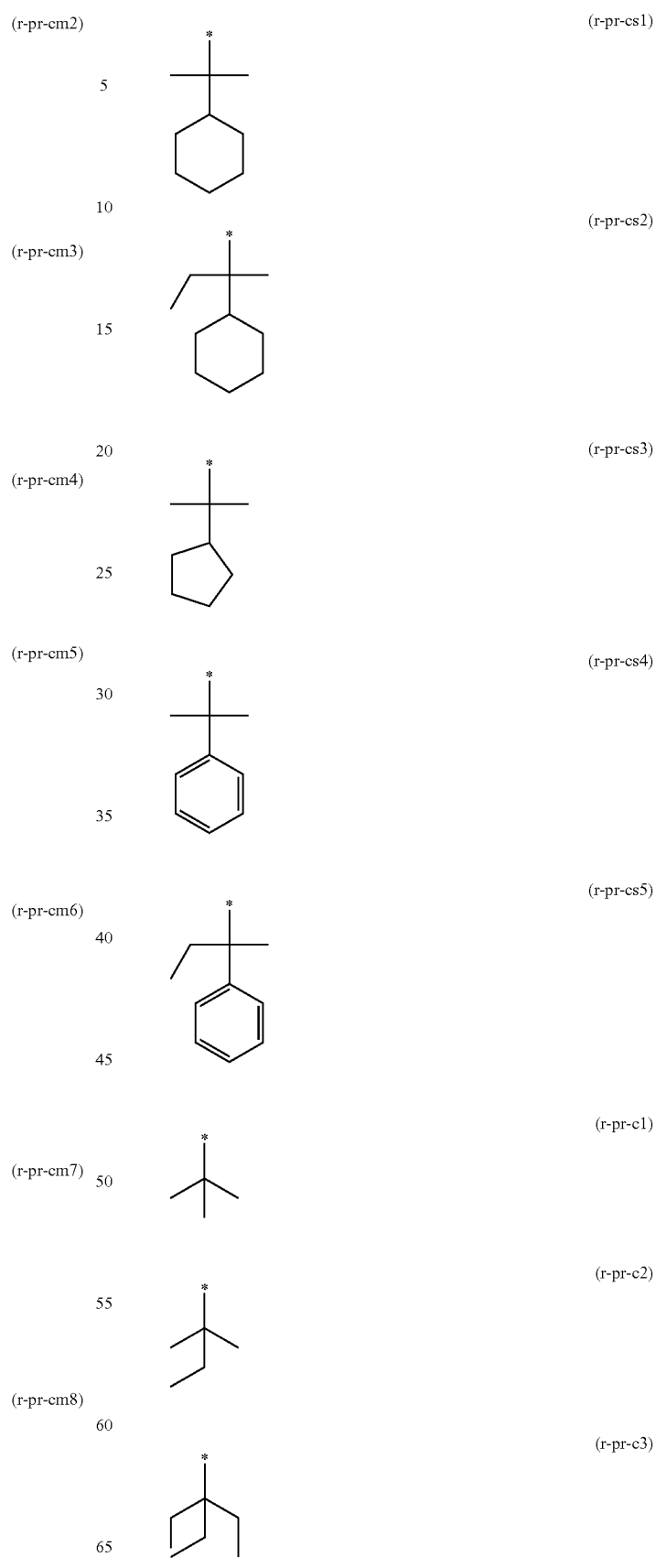

(r-pr-c4)

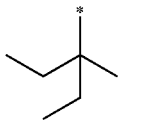

(r-pr-c5)

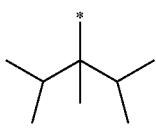

Examples of the acid dissociable group for protecting a hydroxy group as a polar group include the acid dissociable group represented by general formula (a1-r-3) shown below (hereafter, referred to as "tertiary alkyloxycarbonyl-type acid dissociable group").

[Chemical Formula 11]

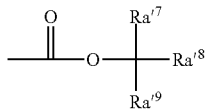

(a1-r-3)

In the formula, $Ra'^7$ to $Ra'^9$ each independently represents an alkyl group.

In the formula (a1-r-3), $Ra'^7$ to $Ra'^9$ is preferably an alkyl group of 1 to 5 carbon atoms, and more preferably an alkyl group of 1 to 3 carbon atoms.

Further, the total number of carbon atoms within the alkyl group is preferably 3 to 7, more preferably 3 to 5, and most preferably 3 or 4.

Examples of the structural unit (a1) include a structural unit derived from an acrylate ester which may have the hydrogen atom bonded to the carbon atom on the α-position substituted with a substituent and contains an acid decomposable group which exhibits increased polarity by the action of acid; a structural unit derived from hydroxystyrene or a hydroxystyrene derivative in which at least a part of the hydrogen atom of the hydroxy group is protected with a substituent containing an acid decomposable group; and a structural unit derived from vinylbenzoic acid or a vinylbenzoic acid derivative in which at least a part of the hydrogen atom within —C(=O)—OH is protected with a substituent containing an acid decomposable group.

As the structural unit (a1), a structural unit derived from an acrylate ester which may have the hydrogen atom bonded to the carbon atom on the α-position substituted with a substituent is preferable.

As the structural unit (a1), structural units represented by general formulae (a1-1) to (a1-3) shown below are preferable.

[Chemical Formula 12]

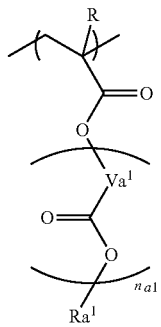

(a1-1)

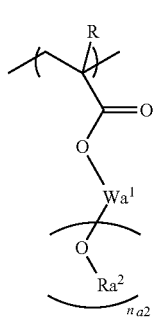

(a1-2)

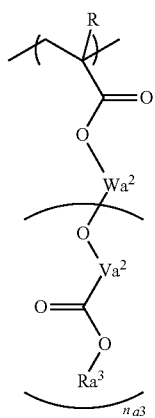

(a1-3)

In the formulae, R represents a hydrogen atom, an alkyl group of 1 to 5 carbon atoms or a halogenated alkyl group of 1 to 5 carbon atoms; $Va^1$ represents a divalent hydrocarbon group which may contain an ether bond, an urethane bond or an amide bond; each $n_{a1}$ represents an integer of 0 to 2; $Ra^1$ represents an acid dissociable group represented by the aforementioned formula (a1-r-1) or (a1-r-2); $Wa^1$ represents a hydrocarbon group having a valency of $n_{a2}+1$; $n_{a2}$ represents an integer of 1 to 3; $Ra^2$ represents an acid dissociable group represented by the aforementioned formula (a1-r-1) or (a1-r-3); $Wa^2$ represents a hydrocarbon group having a valency of $n_{a3}+1$; $n_{a3}$ represents an integer of 1 to 3; $Va^2$ represents a divalent hydrocarbon group which may contain an ether bond, an urethane bond or an amide bond; $Ra^3$ represents an acid dissociable group represented by the aforementioned formula (a1-r-1) or (a1-r-2).

In general formulae (a1-1) to (a1-3), as the alkyl group of 1 to 5 carbon atoms for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group.

The halogenated alkyl group of 1 to 5 carbon atoms represented by R is a group in which part or all of the hydrogen atoms of the aforementioned alkyl group of 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In general formula (a1-1), the hydrocarbon group for $Va^1$ may be either an aliphatic hydrocarbon group or an aromatic hydrocarbon group. An "aliphatic hydrocarbon group" refers to a hydrocarbon group that has no aromaticity. The aliphatic hydrocarbon group as the divalent hydrocarbon group for $Va^1$ may be either saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

Further, as the group for $Va^1$, a group in which the aforementioned divalent hydrocarbon group has been bonded via an ether bond, urethane bond or amide bond can be mentioned.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

As examples of the hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given. As the linear or branched aliphatic hydrocarbon group, the same groups as those described above can be used.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The aromatic hydrocarbon group is a hydrocarbon group having an aromatic ring.

The aromatic hydrocarbon group as the divalent hydrocarbon group for $Va^1$ preferably has 3 to 30 carbon atoms, more preferably 5 to 30, still more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring (arylene group); and a group in which one hydrogen atom has been removed from the aforementioned aromatic hydrocarbon ring (aryl group) and one hydrogen atom has been substituted with an alkylene group (such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atom, more preferably 1 or 2, and most preferably 1.

In the aforementioned formula (a1-2), the hydrocarbon group for $Wa^1$ having a valency of $n_{a2}+1$ may be either an aliphatic hydrocarbon group or an aromatic hydrocarbon group. The aliphatic cyclic group refers to a hydrocarbon group that has no aromaticity, and may be either saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof. As the specific examples thereof, the same groups as those described above for $Va^1$ in the aforementioned formula (a1-1) can be mentioned.

The valency of $n_{a2}+1$ is preferably divalent, trivalent or tetravalent, and divalent or trivalent is more preferable.

In the aforementioned formula (a1-3), the hydrocarbon group for $Wa^2$ having a valency of $n_{a3}+1$ may be either an aliphatic hydrocarbon group or an aromatic hydrocarbon group. The aliphatic cyclic group refers to a hydrocarbon group that has no aromaticity, and may be either saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof. As the specific examples thereof, the same groups as those described above for $Va^1$ in the aforementioned formula (a1-1) can be mentioned.

The valency of $n_{a3}+1$ is preferably divalent, trivalent or tetravalent, and divalent or trivalent is more preferable.

In formula (a1-3), examples of $Va^2$ are the same as defined for the groups for $Va^1$ in formula (a1-1).

As the structural unit (a1-2), a structural unit represented by general formula (a1-2-01) shown below is particularly desirable.

[Chemical Formula 13]

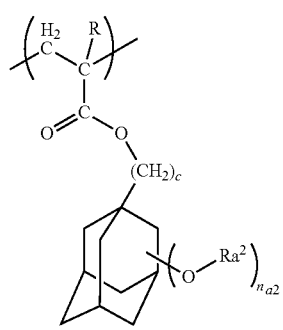

(a1-2-01)

In the formula (a1-2-01), $Ra^2$ represents an acid dissociable group represented by the aforementioned formula (a1-r-1) or (a1-r-3); $n_{a2}$ is an integer of 1 to 3, preferably 1 or 2, and more preferably 1; c is an integer of 0 to 3, preferably 0 or 1, and more preferably 1; R is the same as defined above.

Specific examples of structural units represented by general formulae (a1-1) and (a1-2) are shown below. In the formulae shown below, $R^\alpha$ represents a hydrogen atom, a methyl group or a trifluoromethyl group.

[Chemical Formula 14]

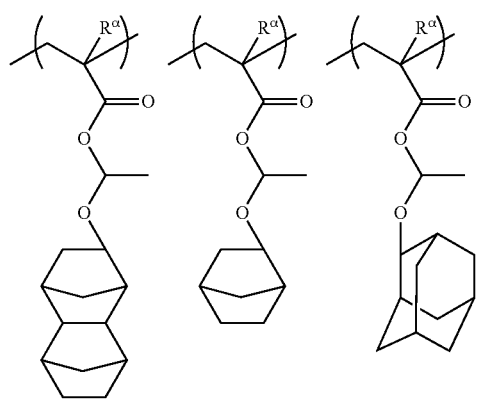

-continued

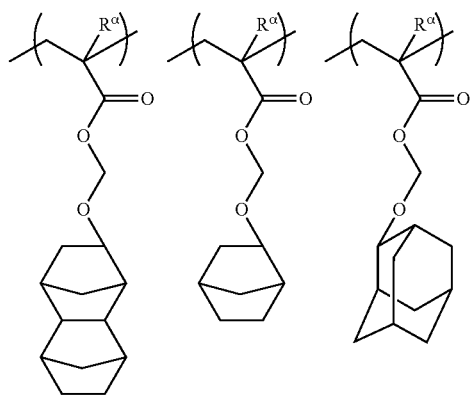

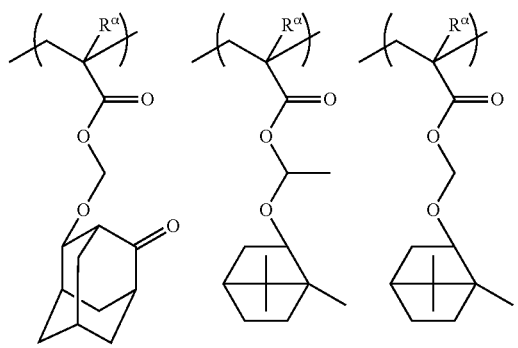

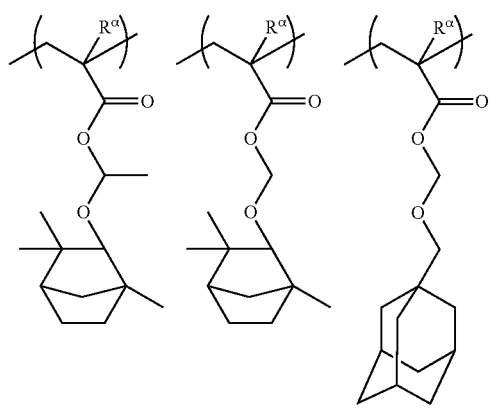

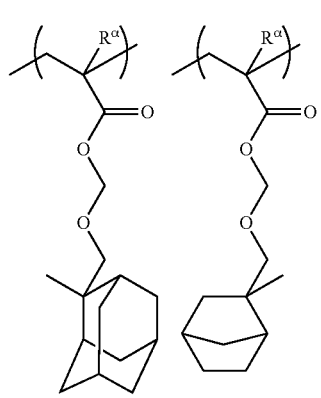

[Chemical Formula 15]
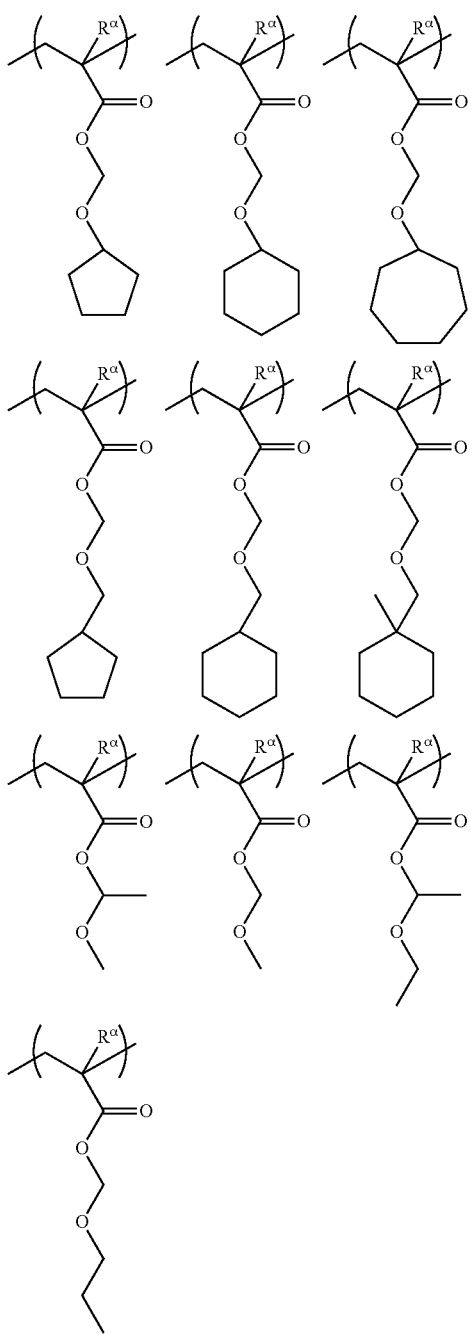
[Chemical Formula 16]
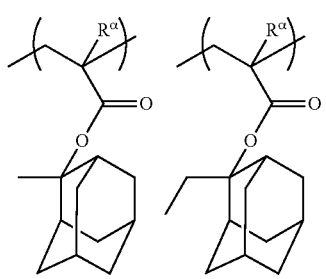
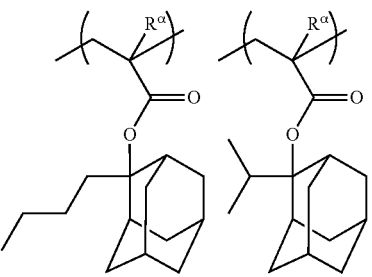
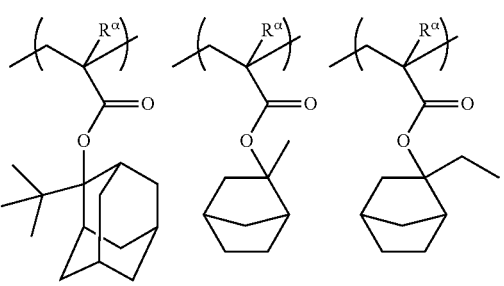
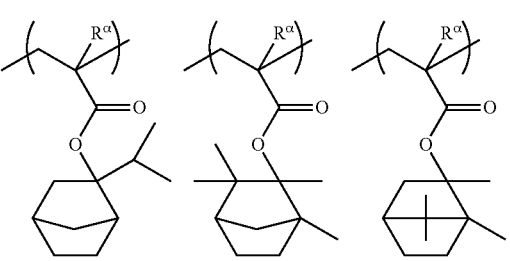
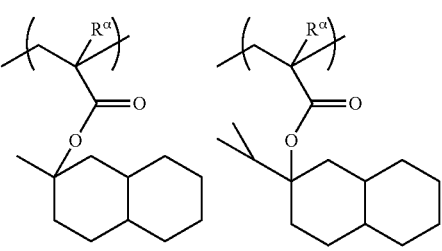
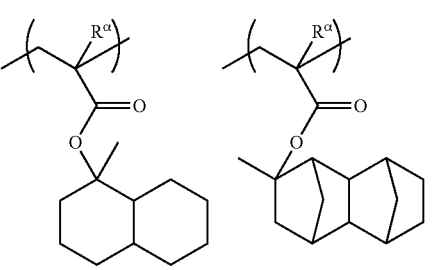
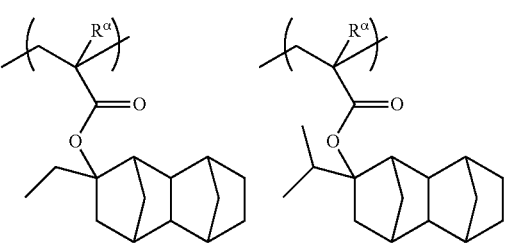

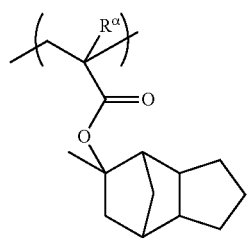
[Chemical Formula 17]
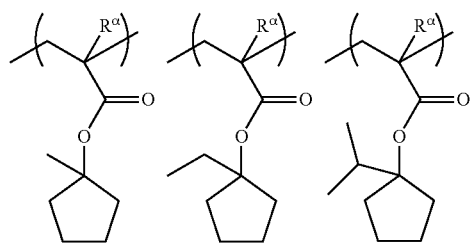
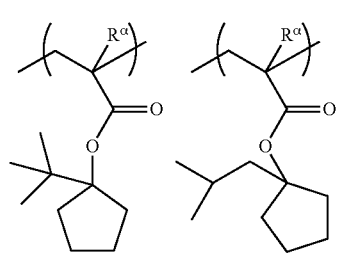
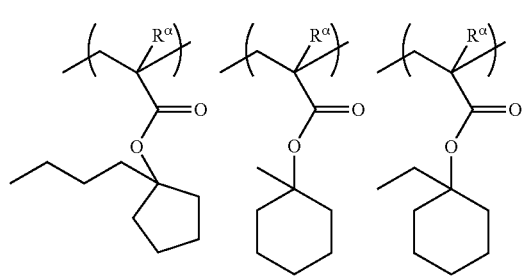
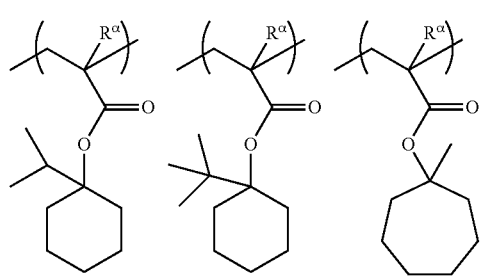
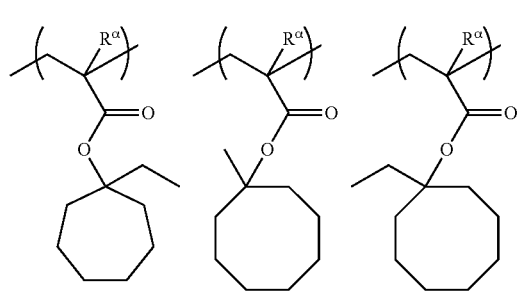
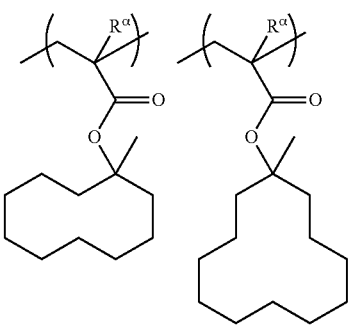
[Chemical Formula 18]
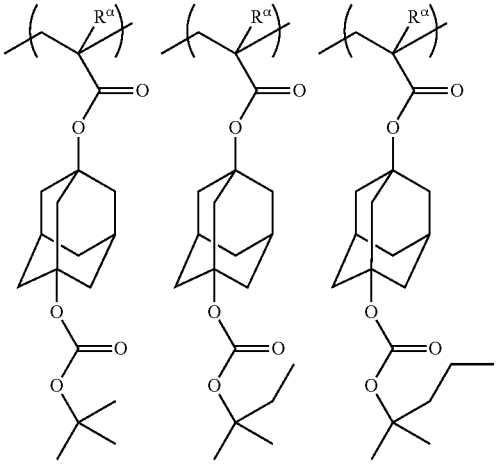
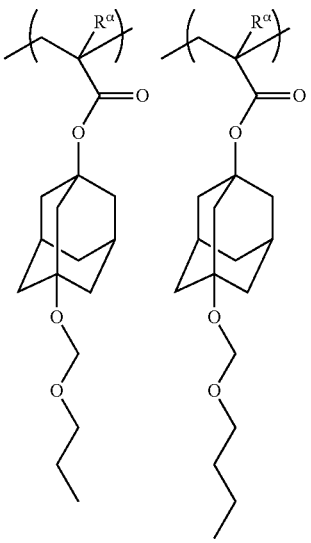

-continued

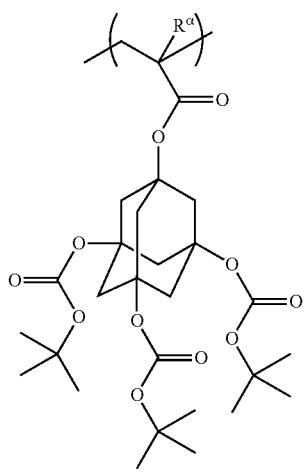

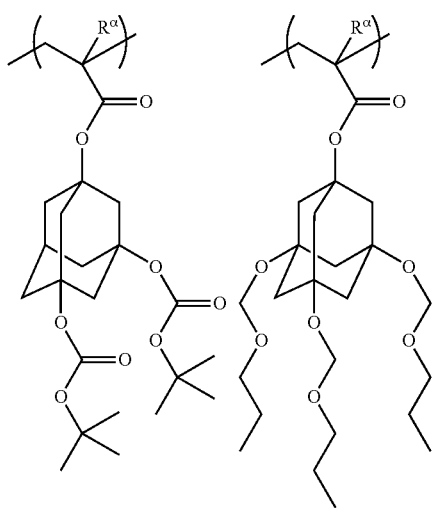

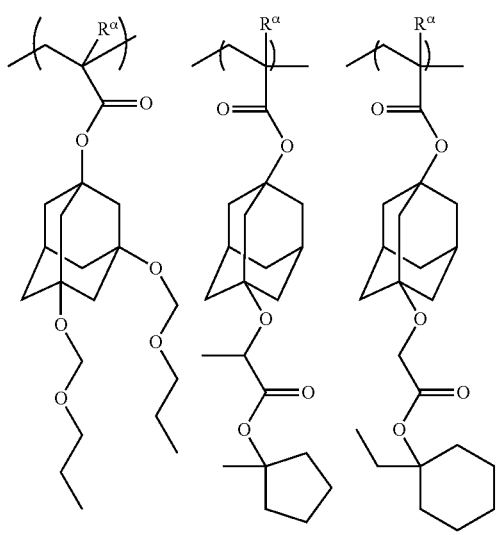

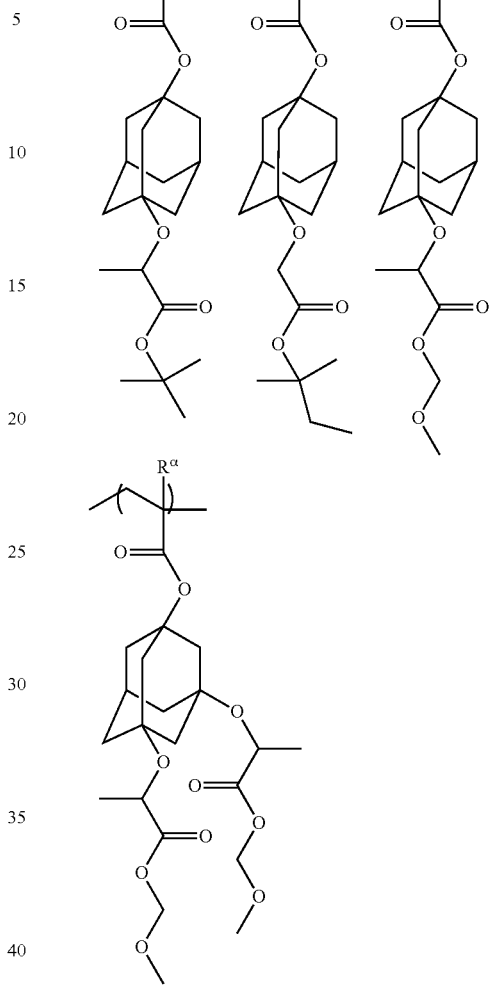

As the structural unit (a1) contained in the component (A1), 1 type of structural unit may be used, or 2 or more types may be used.

In the component (A1), the amount of the structural unit (a1) based on the combined total of all structural units constituting the component (A1) is preferably 20 to 80 mol %, more preferably 20 to 75 mol %, and still more preferably 25 to 70 mol %. By ensuring the lower limit, various lithography properties such as sensitivity, resolution and LWR are improved. On the other hand, when the amount of the structural unit (a1) is no more than the upper limit of the above-mentioned range, a good balance can be achieved with the other structural units.

(Structural Unit (a2))

The structural unit (a2) is a structural unit containing a lactone-containing cyclic group, an —SO$_2$— containing cyclic group or a carbonate-containing cyclic group.

When the component (A1) is used for forming a resist film, the lactone-containing cyclic group, the —SO$_2$— containing cyclic group or the carbonate-containing cyclic group within the structural unit (a2) is effective in improving the adhesion between the resist film and the substrate. The aforementioned structural unit (a1) which contains a lactone-containing cyclic group, —SO$_2$— containing cyclic group or a carbonate-containing cyclic group falls under the definition of the structural unit (a2); however, such a structural unit is regarded as a structural unit (a1), and does not fall under the definition of the structural unit (a2).

The term "lactone-containing cyclic group" refers to a cyclic group including a ring containing a —O—C(=O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

As the lactone-containing cyclic group, there is no particular limitation, and an arbitrary group may be used.

Specific examples include groups represented by general formulae (a2-r-1) to (a2-r-7) shown below.

[Chemical Formula 19]

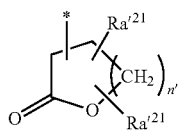
(a2-r-1)

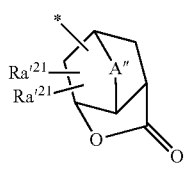
(a2-r-2)

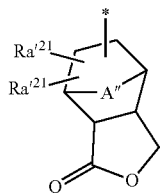
(a2-r-3)

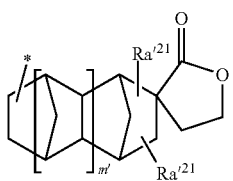
(a2-r-4)

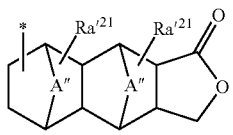
(a2-r-5)

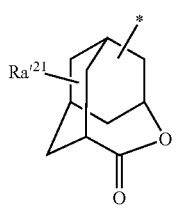
(a2-r-6)

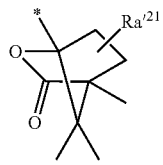
(a2-r-7)

In the formulae, each $Ra'^{21}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom, a sulfur atom or an alkylene group of 1 to 5 carbon atoms which may contain an oxygen atom or a sulfur atom; n' represents an integer of 0 to 2; and m' represents 0 or 1.

In general formulae (a2-r-1) to (a2-r-7) above, A" represents an oxygen atom (—O—), a sulfur atom (—S—) or an alkylene group of 1 to 5 carbon atoms which may contain an oxygen atom or a sulfur atom. As the alkylene group of 1 to 5 carbon atoms for A", a linear or branched alkylene group is preferable, and examples thereof include a methylene group, an ethylene group, an n-propylene group and an isopropylene group. Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—CH$_2$—, —CH$_2$—O—CH$_2$—, —S—CH$_2$— and —CH$_2$—S—CH$_2$—. As A", an alkylene group of 1 to 5 carbon atoms or —O— is preferable, more preferably an alkylene group of 1 to 5 carbon atoms, and most preferably a methylene group.

In formulae (a2-r-1) to (a2-r-7), the alkyl group for $Ra'^{21}$ is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is particularly desirable.

The alkoxy group for $Ra'^{21}$ is preferably an alkoxy group of 1 to 6 carbon atoms.

Further, the alkoxy group is preferably a linear or branched alkoxy group. Specific examples of the alkoxy groups include the aforementioned alkyl groups for $Ra'^{21}$ having an oxygen atom (—O—) bonded thereto.

As examples of the halogen atom for $Ra'^{21}$, a fluorine atom, chlorine atom, bromine atom and iodine atom can be given. Among these, a fluorine atom is preferable.

Examples of the halogenated alkyl group for $Ra'^{21}$ include groups in which part or all of the hydrogen atoms within the aforementioned alkyl group for $Ra'^{21}$ has been substituted with the aforementioned halogen atoms. As the halogenated alkyl group, a fluorinated alkyl group is preferable, and a perfluoroalkyl group is particularly desirable.

With respect to —COOR" and —OC(=O)R" for $Ra'^{21}$, R" represents a hydrogen atom, an alkyl group, a lactone-containing cyclic group, a carbonate-containing cyclic group or an —SO$_2$— containing cyclic group.

The alkyl group for R" may be linear, branched or cyclic, and preferably has 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and most preferably 5 to 10 carbon atoms. Specific examples include groups in which one or more hydrogen atoms have been removed from a monocycloalkane or a polycycloalkane such as a bicycloalkane, tricycloalkane or tetracycloalkane which may or may not be substituted with a fluorine atom or a fluorinated alkyl group. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

Examples of the lactone-containing cyclic group for R" include groups represented by the aforementioned general formulae (a2-r-1) to (a2-r-7).

The carbonate-containing cyclic group for R" is the same as defined for the carbonate-containing cyclic group described later. Specific examples of the carbonate-containing cyclic group include groups represented by general formulae (ax3-r-1) to (ax3-r-3).

The —$SO_2$— containing cyclic group for R" is the same as defined for the —$SO_2$— containing cyclic group described later. Specific examples of the —$SO_2$— containing cyclic group include groups represented by general formulae (a5-r-1) to (a5-r-4).

The hydroxyalkyl group for $Ra'^{21}$ preferably has 1 to 6 carbon atoms, and specific examples thereof include the alkyl groups for $Ra'^{21}$ in which at least one hydrogen atom has been substituted with a hydroxy group.

In formulae (a2-r-2), (a2-r-3) and (a2-r-5), as the alkylene group of 1 to 5 carbon atoms represented by A", a linear or branched alkylene group is preferable, and examples thereof include a methylene group, an ethylene group, an n-propylene group and an isopropylene group. Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—$CH_2$—, —$CH_2$—O—$CH_2$—, —S—$CH_2$— and —$CH_2$—S—$CH_2$—. As A", an alkylene group of 1 to 5 carbon atoms or —O— is preferable, more preferably an alkylene group of 1 to 5 carbon atoms, and most preferably a methylene group.

Specific examples of the groups represented by the aforementioned general formulae (a2-r-1) to (a2-r-7) are shown below.

[Chemical Formula 20]

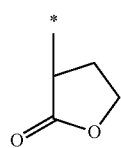

(r-Ic-1-1)

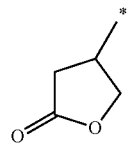

(r-Ic-1-2)

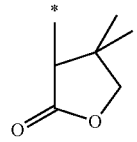

(r-Ic-1-3)

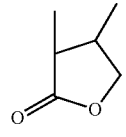

(r-Ic-1-4)

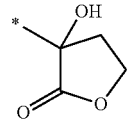

(r-Ic-1-5)

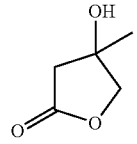

(r-Ic-1-6)

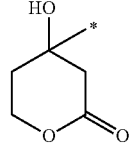

(r-Ic-1-7)

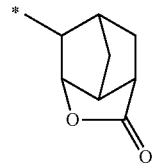

(r-Ic-2-1)

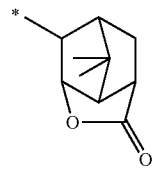

(r-Ic-2-2)

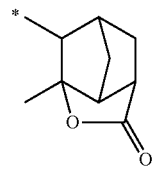

(r-Ic-2-3)

(r-Ic-2-4)
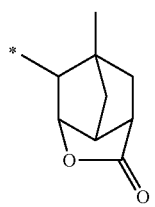
(r-Ic-2-5)
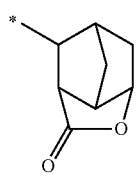
(r-Ic-2-6)
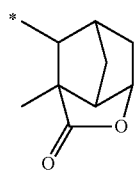
(r-Ic-2-7)
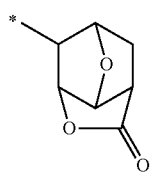
(r-Ic-2-8)
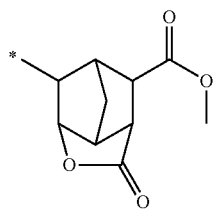
(r-Ic-2-9)
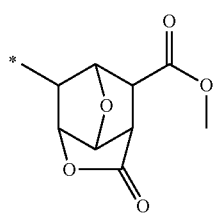
(r-Ic-2-10)
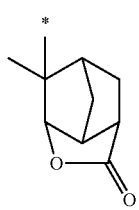
(r-Ic-2-11)
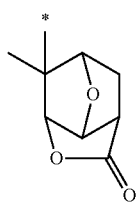
(r-Ic-2-12)
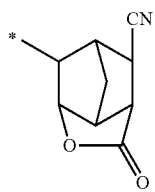
(r-Ic-2-13)
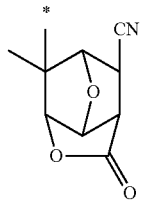
(r-Ic-3-1)
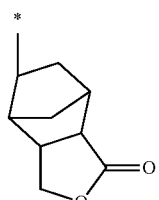
(r-Ic-3-2)
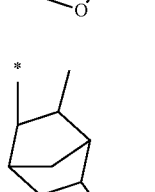
(r-Ic-3-3)
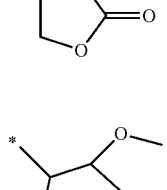
(r-Ic-3-4)
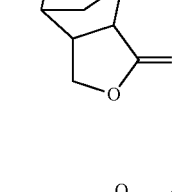
(r-Ic-3-5)
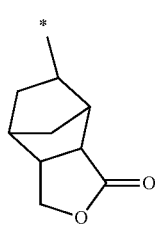

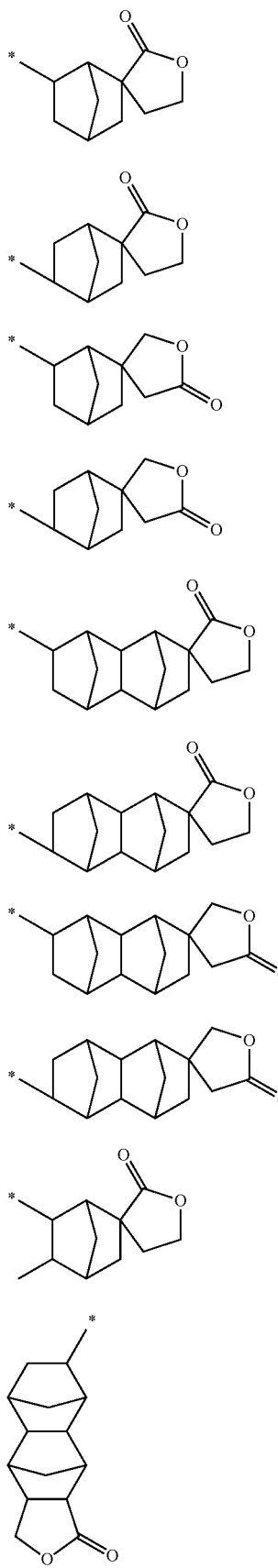
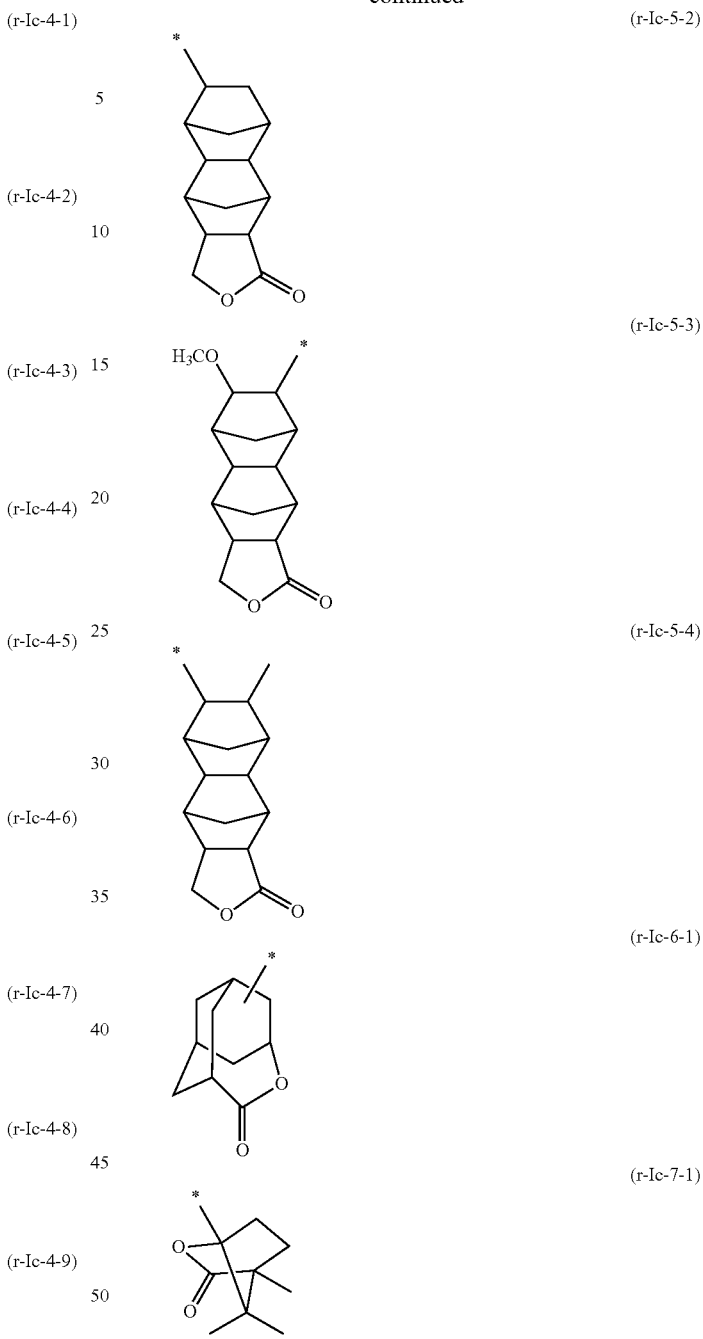

An "—$SO_2$— containing cyclic group" refers to a cyclic group having a ring containing —$SO_2$— within the ring structure thereof, i.e., a cyclic group in which the sulfur atom (S) within —$SO_2$— forms part of the ring skeleton of the cyclic group. The ring containing —$SO_2$— within the ring skeleton thereof is counted as the first ring. A cyclic group in which the only ring structure is the ring that contains —$SO_2$— in the ring skeleton thereof is referred to as a monocyclic group, and a group containing other ring structures is described as a polycyclic group regardless of the structure of the other rings. The —$SO_2$— containing cyclic group may be either a monocyclic group or a polycyclic group.

As the —$SO_2$— containing cyclic group, a cyclic group containing —O—$SO_2$— within the ring skeleton thereof, i.e., a cyclic group containing a sultone ring in which —O—S— within the —O—SO$_2$— group forms part of the ring skeleton thereof is particularly desirable. More specific examples of the —SO$_2$— containing cyclic group include groups represented by general formulae (a5-r-1) to (a5-r-4) shown below.

[Chemical Formula 21]

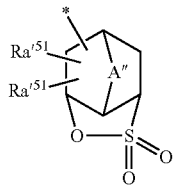
(a5-r-1)

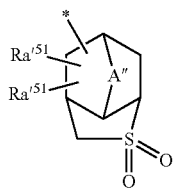
(a5-r-2)

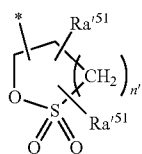
(a5-r-3)

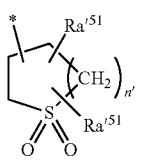
(a5-r-4)

In the formulae, each Ra'$^{51}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom, a sulfur atom or an alkylene group of 1 to 5 carbon atoms which may contain an oxygen atom or a sulfur atom; and n' represents an integer of 0 to 2.

In general formulae (a5-r-1) to (a5-r-4), A" is the same as defined for A" in general formulae (a2-r-1) to (a2-r-7). The alkyl group, alkoxy group, halogen atom, halogenated alkyl group, —COOR", —OC(=O)R" and hydroxyalkyl group for Ra'$^{51}$ are the same as defined for Ra'$^{21}$ in the aforementioned general formulae (a2-r-1) to (a2-r-7).

Specific examples of the groups represented by the aforementioned general formulae (a5-r-1) to (a5-r-4) are shown below. In the formulae shown below, "Ac" represents an acetyl group.

[Chemical Formula 22]

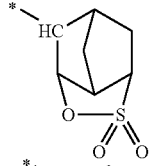
(r-sl-1-1)

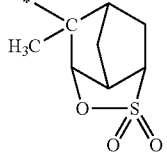
(r-sl-1-2)

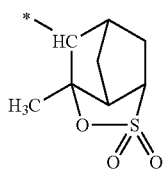
(r-sl-1-3)

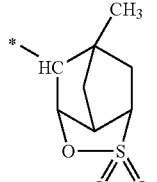
(r-sl-1-4)

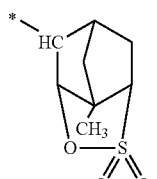
(r-sl-1-5)

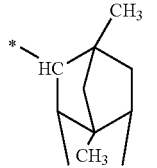
(r-sl-1-6)

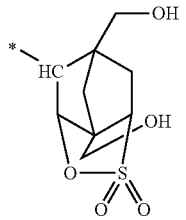
(r-sl-1-7)

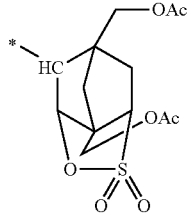
(r-sl-1-8)

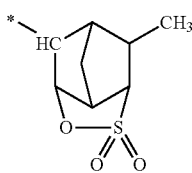

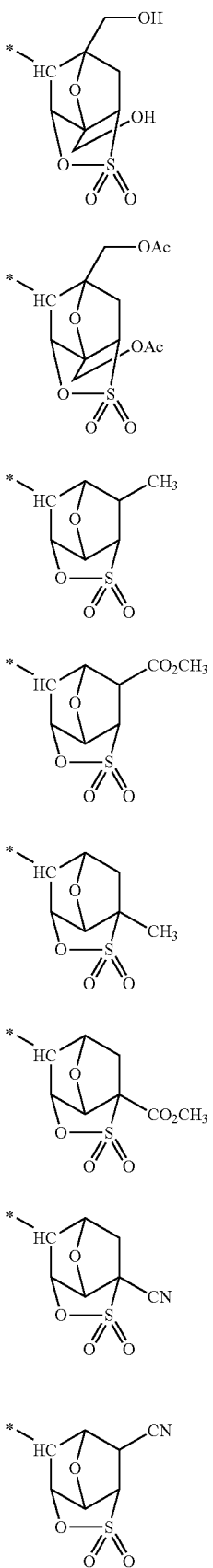
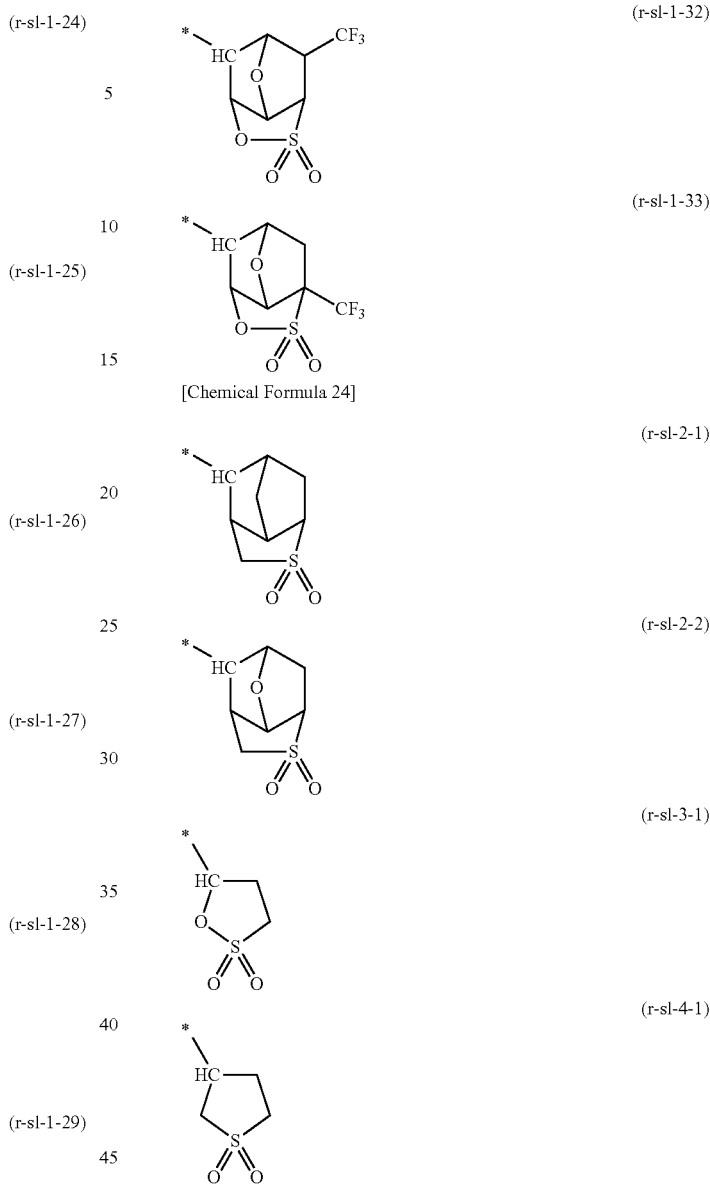

As the —SO$_2$— containing cyclic group, a group represented by the aforementioned general formula (a5-r-1) is preferable, at least one member selected from the group consisting of groups represented by the aforementioned chemical formulas (r-s1-1-1), (r-s1-1-18), (r-s1-3-1) and (r-s1-4-1) is more preferable, and a group represented by chemical formula (r-s1-1) is most preferable.

The term "carbonate-containing cyclic group" refers to a cyclic group including a ring containing a —O—C(=O)—O— structure (carbonate ring). The term "carbonate ring" refers to a single ring containing a —O—C(=O)—O— structure, and this ring is counted as the first ring. A carbonate-containing cyclic group in which the only ring structure is the carbonate ring is referred to as a monocyclic group, and groups containing other ring structures are described as polycyclic groups regardless of the structure of the other rings. The carbonate-containing cyclic group may be either a monocyclic group or a polycyclic group.

The carbonate-containing cyclic group is not particularly limited, and an arbitrary group may be used. Specific examples include groups represented by general formulae (ax3-r-1) to (ax3-r-3) shown below.

[Chemical Formula 25]

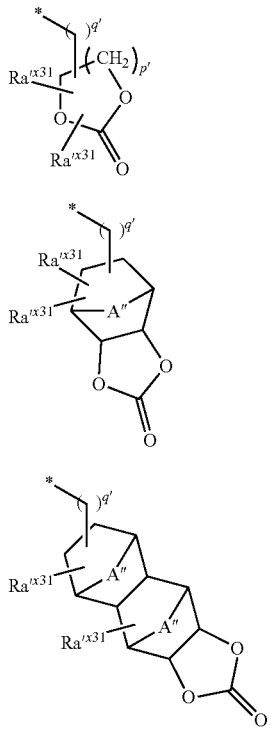

(ax3-r-1)

(ax3-r-2)

(ax3-r-3)

In the formulae, each Ra'$^{x31}$ independently represents a hydrogen atom, an alkyl group, an alkoxy group, a halogen atom, a halogenated alkyl group, a hydroxy group, —COOR'', —OC(=O)R'', a hydroxyalkyl group or a cyano group; R'' represents a hydrogen atom, an alkyl group, a lactone-containing cyclic group, a carbonate-containing cyclic group or an —SO$_2$— containing cyclic group; A'' represents an oxygen atom, a sulfur atom or an alkylene group of 1 to 5 carbon atoms which may contain an oxygen atom or a sulfur atom; p' represents an integer of 0 to 3; and q' represents 0 or 1.

In general formulae (ax3-r-1) to (ax3-r-3), A'' is the same as defined for A'' in general formula (a2-r-1).

Examples of the alkyl group, alkoxy group, halogen atom, halogenated alkyl group, —COOR'', —OC(=O)R'' and hydroxyalkyl group for Ra'$^{31}$ include the same groups as those described above in the explanation of Ra'$^{21}$ in the general formulas (a2-r-1) to (a2-r-7).

Specific examples of the groups represented by the aforementioned general formulae (ax3-r-1) to (ax3-r-3) are shown below.

[Chemical Formula 26]

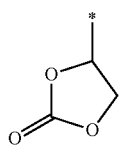

(r-cr-1-1)

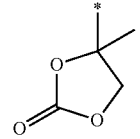

(r-cr-1-2)

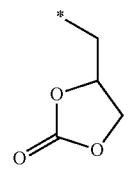

(r-cr-1-3)

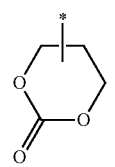

(r-cr-1-4)

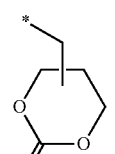

(r-cr-1-5)

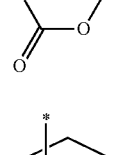

(r-cr-1-6)

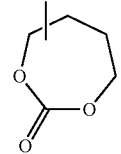

(r-cr-1-6)

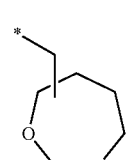

(r-cr-2-1)

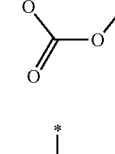

(r-cr-2-2)

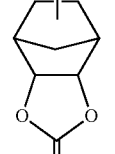

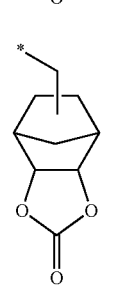

(r-cr-2-3)
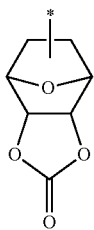

(r-cr-2-4)
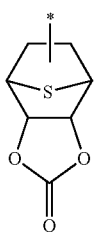

(r-cr-3-1)
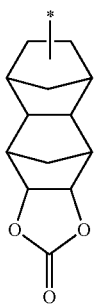

(r-cr-3-2)
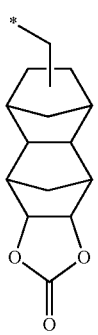

(r-cr-3-3)

(r-cr-3-4)
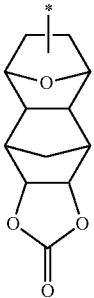

(r-cr-3-5)
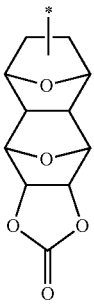

Among the above examples, a lactone-containing cyclic group or an —SO$_2$— containing cyclic group is preferable, a group represented by the general formula (a2-r-1), (a2-r-2) or (a5-r-1) is more preferable, and a group represented by any one of the chemical formulae (r-1c-1-1) to (r-1c-1-7), (r-1c-2-1) to (r-1c-2-13), (r-s1-1-1) and (r-s1-1-18) is still more preferable.

As the structural unit (a2), a structural unit derived from an acrylate ester which may have the hydrogen atom bonded to the carbon atom on the α-position substituted with a substituent is preferable.

The structural unit (a2) is preferably a structural unit represented by general formula (a2-1) shown below.

[Chemical Formula 27]

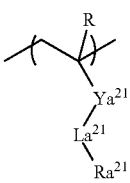

(a2-1)

In the formula, R represents a hydrogen atom, an alkyl group of 1 to 5 carbon atoms, a halogenated alkyl group of 1 to 5 carbon atoms, a hydroxyalkyl group, an alkoxy group; Ya$^{21}$ represents a single bond or a divalent linking group; La$^{21}$ represents —O—, —COO— or —OCO—; and R' represents a hydrogen atom or a methyl group, provided that, when La$^{21}$ represents —O—, Ya$^{21}$ does not represents —CO—; and Ra$^{21}$ represents a lactone-containing cyclic group, a carbonate-containing cyclic group or an —SO$_2$— containing cyclic group.

The divalent linking group for Ya$^{21}$ is not particularly limited, and preferable examples thereof include a divalent hydrocarbon group which may have a substituent and a divalent linking group containing a hetero atom.

Divalent Hydrocarbon Group which May have a Substituent

The hydrocarbon group as a divalent linking group may be either an aliphatic hydrocarbon group or an aromatic hydrocarbon group.

An "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof. Specifically, groups exemplified above for $Va^1$ in the aforementioned formula (a1-1) ca be mentioned.

The linear or branched aliphatic hydrocarbon group may or may not have a substituent. Examples of the substituent include a fluorine atom, a fluorinated alkyl group of 1 to 5 carbon atoms, and a carbonyl group.

In the aliphatic hydrocarbon group containing a ring, the cyclic aliphatic hydrocarbon group may or may not have a substituent. Examples of the substituent include an alkyl group, an alkoxy group, a halogen atom, a halogenated alkyl group, a hydroxyl group and a carbonyl group.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

The cyclic aliphatic hydrocarbon group may have part of the carbon atoms constituting the ring structure thereof substituted with a substituent containing a hetero atom. As the substituent containing a hetero atom, —O—, —C(=O)—O—, —S—, —S(=O)$_2$— or —S(=O)$_2$—O— is preferable.

Specific examples of the aromatic hydrocarbon group as a divalent hydrocarbon group include the same group as exemplified above for $Va^1$ in the aforementioned formula (a1-1).

With respect to the aromatic hydrocarbon group, the hydrogen atom within the aromatic hydrocarbon group may be substituted with a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group of 1 to 5 carbon atoms, and a methyl group, an ethyl group, a propyl group, an n-butyl group or a tert-butyl group is particularly desirable.

As the alkoxy group, the halogen atom and the halogenated alkyl group for the substituent, the same groups as the aforementioned substituent groups for substituting a hydrogen atom within the cyclic aliphatic hydrocarbon group can be used.

Divalent Linking Group Containing a Hetero Atom

With respect to a divalent linking group containing a hetero atom, a hetero atom is an atom other than carbon and hydrogen, and examples thereof include an oxygen atom, a nitrogen atom, a sulfur atom and a halogen atom.

In the case where $Ya^{21}$ represents a divalent linking group containing a hetero atom, preferable examples of the linking group include —O—, —C(=O)—O—, —C(=O)—, —O—C(=O)—O—, —C(=O)—NH—, —NH—, —NH—C(=NH)— (wherein H may be substituted with a substituent such as an alkyl group or an acyl group), —S—, —S(=O)$_2$—, —S(=O)$_2$—O—, a group represented by general formula —$Y^{21}$—O—$Y^{22}$—, —$Y^{21}$—O—, —$Y^{21}$—C(=O)—O—, —C(=O)—O—$Y^{21}$, —[$Y^{21}$—C(=O)—O]$_{m'}$—$Y^{22}$— or —$Y^{21}$—O—C(=O)—$Y^{22}$— [in the formulae, $Y^{21}$ and $Y^{22}$ each independently represents a divalent hydrocarbon group which may have a substituent, and O represents an oxygen atom; and m' represents an integer of 0 to 3.

The divalent linking group containing a hetero atom represents —C(=O)—NH—, —NH—, or —NH—C(=NH)—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In formulae —$Y^{21}$—O—$Y^{22}$—, —$Y^{21}$—O—, $Y^{21}$—C(=O)—O—, —C(=O)—O—$Y^{21}$, —[$Y^{21}$—C(=O)—O]$_{m'}$—$Y^{22}$— and —$Y^{21}$—O—C(=O)—$Y^{22}$—, $Y^{21}$ and $Y^{22}$ each independently represents a divalent hydrocarbon group which may have a substituent. Examples of the divalent hydrocarbon group include the same groups as those described above as the "divalent hydrocarbon group which may have a substituent" in the explanation of the aforementioned divalent linking group.

As $Y^{21}$, a linear aliphatic hydrocarbon group is preferable, more preferably a linear alkylene group, still more preferably a linear alkylene group of 1 to 5 carbon atoms, and a methylene group or an ethylene group is particularly desirable.

As $Y^{22}$, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula —[$Y^{21}$—C(=O)—O]$_{m'}$—$Y^{22}$—, m' represents an integer of 0 to 3, preferably an integer of 0 to 2, more preferably 0 or 1, and most preferably 1. Namely, it is particularly desirable that the group represented by the formula —[$Y^{21}$—C(=O)—O]$_{m'}$—$Y^{22}$— is a group represented by the formula —$Y^{21}$—C(=O)—O—$Y^{22}$—. Among these, a group represented by the formula —(CH$_2$)$_{a'}$—C(=O)—O—(CH$_2$)$_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

$Ya^{21}$ preferably represents an ester bond [—C(=O)—O—], an ether bond (—O—), a linear or branched alkylene group, a combination of these, or a single bond.

In the formula (a2-1), $Ra^{21}$ represents the aforementioned lactone-containing cyclic group, —SO$_2$— containing cyclic group or carbonate-containing cyclic group.

As the structural unit (a2) contained in the component (A1), 1 type of structural unit may be used, or 2 or more types may be used.

When the component (A1) contains the structural unit (a2), the amount of the structural unit (a2) based on the combined total of all structural units constituting the component (A1) is preferably 1 to 80 mol %, more preferably 5 to 70 mol %, still more preferably 10 to 65 mol %, and most preferably 10 to 60 mol %. When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units, and various lithography properties and pattern shape can be improved.

(Structural Unit (a3))

The structural unit (a3) is a structural unit containing a polar group-containing aliphatic hydrocarbon group (provided that the structural units that fall under the definition of structural units (a1) and (a2) are excluded).

When the component (A1) includes the structural unit (a3), it is presumed that the hydrophilicity of the component (A1) is enhanced, thereby contributing to improvement in resolution.

Examples of the polar group include a hydroxyl group, cyano group, carboxyl group, or hydroxyalkyl group in which part of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and cyclic aliphatic hydrocarbon groups (cyclic groups). These cyclic groups can be selected appropriately from the multitude of groups that have been proposed for the resins of resist compositions designed for use with ArF excimer lasers. The cyclic group is preferably a polycyclic group, more preferably a polycyclic group of 7 to 30 carbon atoms.

Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

As the structural unit (a3), there is no particular limitation as long as it is a structural unit containing a polar group-containing aliphatic hydrocarbon group, and an arbitrary structural unit may be used.

The structural unit (a3) is preferably a structural unit derived from an acrylate ester which may have the hydrogen atom bonded to the carbon atom on the α-position substituted with a substituent and contains a polar group-containing aliphatic hydrocarbon group.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 28]

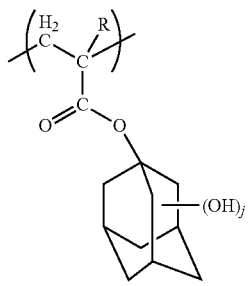
(a3-1)

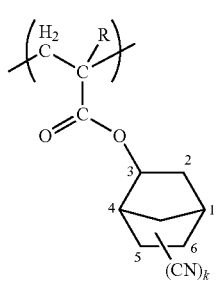
(a3-2)

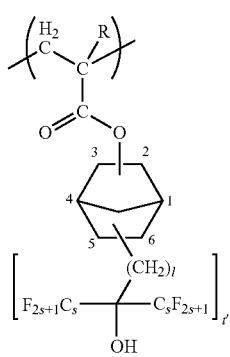
(a3-3)

In the formulas, R is the same as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

As the structural unit (a3) contained in the component (A1), 1 type of structural unit may be used, or 2 or more types may be used.

When the component (A1) includes the structural unit (a3), the amount of the structural unit (a3) based on the combined total of all structural units constituting the component (A1) is preferably 5 to 50 mol %, more preferably 5 to 40 mol %, and still more preferably 5 to 25 mol %.

When the amount of the structural unit (a3) is at least as large as the lower limit of the above-mentioned range, the effect of using the structural unit (a3) can be satisfactorily achieved. On the other hand, when the amount of the structural unit (a3) is no more than the upper limit of the above-mentioned range, a good balance can be achieved with the other structural units.

(Other Structural Units)

The component (A1) may be further include a structural unit other than the structural units (a1) to (a3), as well as the structural units (a1) to (a3).

As the other structural unit, any other structural unit which cannot be classified as the aforementioned structural units can be used without any particular limitation, and any of the multitude of conventional structural units used within resist resins for ArF excimer lasers or KrF excimer lasers (and particularly for ArF excimer lasers) can be used. For example, a structural unit (a4) shown below or a structural unit (a6) described later can be used.

Structural Unit (a4):

The structural unit (a4) is a structural unit containing an acid non-dissociable cyclic group. When the component (A1) includes the structural unit (a4), dry etching resistance of the resist pattern to be formed is improved. Further, the hydrophobicity of the component (A1) is further improved. Increase in the hydrophobicity contributes to improvement in terms of resolution, shape of the resist pattern and the like, particularly in the case of applying an organic solvent developing process.

An "acid non-dissociable, aliphatic cyclic group" in the structural unit (a4) refers to a cyclic group which is not dissociated by the action of acid generated from the component (B) described later upon exposure, and remains in the structural unit.

As the structural unit (a4), a structural unit which contains a non-acid-dissociable aliphatic cyclic group, and is also derived from an acrylate ester is preferable. Examples of this cyclic group include the same groups as those described above in relation to the aforementioned structural unit (a1), and any of the multitude of conventional groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecyl group, adamantyl group, tetracyclododecyl group, isobornyl group, and norbornyl group is particularly desirable. These polycyclic groups may be substituted with a linear or branched alkyl group of 1 to 5 carbon atoms.

Specific examples of the structural unit (a4) include structural units represented by general formulae (a4-1) to (a4-7) shown below.

[Chemical Formula 29]

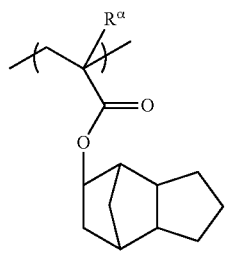
(a4-1)

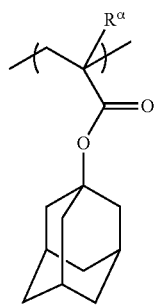
(a4-2)

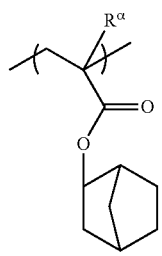
(a4-3)

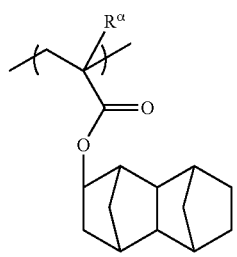
(a4-4)

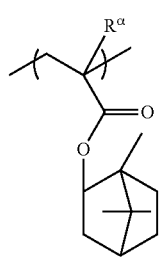
(a4-5)

(a4-6)

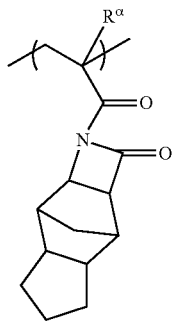

(A4-7)

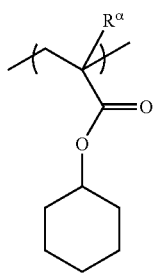

In the formulae, $R^\alpha$ represents a hydrogen atom, a methyl group or a trifluoromethyl group.

As the structural unit (a4) contained in the component (A1), 1 type of structural unit may be used, or 2 or more types may be used.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

The component (A1) is preferably a copolymer containing the structural unit (a1). The copolymer containing the structural unit (a1) is preferably a copolymer further containing at least one of a structural unit (a2) and a structural unit (a3), and still more preferably a copolymer containing the structural units (a1), (a2) and (a3).

The weight average molecular weight (Mw) (the polystyrene equivalent value determined by gel permeation chromatography) of the component (A1) is not particularly limited, but is preferably 1,000 to 50,000, more preferably 1,500 to 30,000, and most preferably 2,000 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the polydispersity (Mw/Mn) of the component (A1) is not particularly limited, but is preferably 1.0 to 5.0, more preferably 1.0 to 3.0, and most preferably 1.2 to 2.5. Here, Mn is the number average molecular weight.

As the component (A), one type may be used alone, or two or more types may be used in combination.

In the component (A), the amount of the component (A1) based on the total weight of the component (A) is preferably 25% by weight or more, more preferably 50% by weight or more, still more preferably 75% by weight or more, and may be even 100% by weight. When the amount of the component (A1) is 25% by weight or more, various lithography properties are improved, such as improvement in mask reproducibility and exposure dose, and reduction of roughness.

In the first resist composition, as the component (A), one type may be used, or two or more types of compounds may be used in combination.

In the first resist composition, the amount of the component (A) can be appropriately adjusted depending on the thickness of the resist film to be formed, and the like.

[Component (B)]

In the first resist composition, the component (B) is an acid generator component which generates acid upon exposure, and includes a compound represented by general formula (b0) shown below (hereafter, sometimes referred to as "compound (b0)").

[Chemical Formula 30]

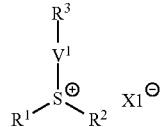

(b0)

In formula (b0), $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group; and $X1^-$ represents a monovalent organic anion capable of generating a strong acid.

(Compound (b0))

In formula (b0), $R^1$, $R^2$, $R^3$ and $V^1$ are the same as defined for $R^1$, $R^2$, $R^3$ and $V^1$ in the aforementioned formula (m0).

In formula (b0), $X1^-$ represents an organic anion capable of generating a strong acid.

A "strong acid" refers to an acid having an acid dissociation constant (pKa) of 0 or less, and preferably −1 or less. The lower limit of the pKa of the strong acid is not particularly limited, but is practically about −15.

Examples of the organic anion capable of generating a strong acid include the anion moieties of compounds represented by general formulae (b-1) to (b-3) described later, and the anion moiety of a compound represented by general formula (b-1) is preferable.

In the present invention, the "acid dissociation constant (pKa)" is a value calculated from the following formula, assuming that the acid strength is stronger (pKa value is smaller) in a compound in which the structure of the acid in an anion state exhibits a lower molecular orbital energy.

Calculation Method:

(1) The structure of the acid in an anion state is optimized by CAChe PM3 method.

(2) From the calculation of the molecular orbital, the HOMO (highest occupied molecular orbital) energy (eV) is determined.

(3) Derive a linear equation between a substance having a known pKa (measured value) in an aqueous solution and the HOMO energy of the substance determined by the above (1) and (2).

(4) The HOMO energy of the objective acid is determined by the above (1) and (2), and the determined HOMO energy is assigned to the linear equation derived in the above (3), thereby calculating pKa (calculated value).

According to the above (1) to (4), even for novel acid, pKa (calculated value) can be calculated by determining the HOMO energy.

The reason for determining the HOMO energy of the acid in an anion state is that the acid strength mainly depends on the structure of the acid in an anion state (and does not depend on the cation structure).

In the calculation method (3) above, the linear equation can be derived by the following steps (i) to (iii).

(i) The acid dissociation constant (pKa) as measured at 25° C. is actually determined with respect to the 8 compounds below.

The acid dissociation constant (pKa) can be measured, for example, in dimethyl sulfoxide (DMSO), using a pKa measuring apparatus (product name: pKa Analyzer Pro; manufactured by Advanced Analytical Technologies, Inc.).

Compounds (Measured Value of pKa):

Chloroacetic acid (pKa2.68), acetic acid (pKa4.56), trichloroacetic acid (pKa0.66), phenol (pKa9.82), dichloroacetic acid (pKa1.3), fluoroacetic acid (pKa2.59), hexanoic acid (pKa4.63) and o-fluorophenol (pKa8.49).

(ii) With respect to each of the above compounds, the HOMO energy is determined from the calculation methods (1) and (2).

Chloroacetic acid (−4.395), acetic acid (−3.925), trichloroacetic acid (−5.073), phenol (−2.691), dichloroacetic acid (−4.763), fluoroacetic acid (−4.31), hexanoic acid (−4.076) and o-fluorophenol (−2.929).

(iii) With respect to each of the above compounds, a graph is plotted with the pKa value measured in (i) on the vertical axis, and the HOMO energy (eV) determined in (ii) on the vertical axis. A linear regression is drawn, so as to derive the linear equation ($R^2=0.9868$).

(HOMO energy)=0.2511×(pKa value)−5.1103

As the compound (b0), one kind of compound may be used alone, or two or more compounds may be used in combination.

In the first resist composition, the amount of the compound (b0) relative to 100 parts by weight of the component (A) is preferably 0.5 to 60 parts by weight, more preferably 1 to 50 parts by weight, and still more preferably 1 to 40 parts by weight.

When the amount of the compound (b0) is at least as large as the lower limit of the above-mentioned range, various lithography properties and the pattern shape can be further improved in the formation of a resist pattern. On the other hand, when the amount of the compound (b0) is no more than the upper limit of the above-mentioned range, a homogeneous solution can be reliably obtained, and the storage stability is improved.

In the component (B), the amount of the compound (b0) based on the total weight of the component (B) is preferably 20% by weight or more, more preferably 40% by weight or more, still more preferably 50% by weight or more, and may be even 100% by weight. The amount of the component (B1) is most preferably 100% by weight. When the amount of the compound (b0) within the component (B) is at least as large the lower limit of the above preferable range, the resist composition can reliably achieve both reduction of roughness and mask reproducibility, and a resist pattern with further improved lithography properties can be formed.

(Component (B1))

In the first resist composition, an acid generator other than the compound (b0) (hereafter, referred to as "component (B1)") may be used in combination as the component (B).

The component (B1) is not particularly limited as long it does not fall under the definition of the compound (b0), and any of the known acid generators used in conventional chemically amplified resist compositions can be used.

Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators. Among these, it is preferable to use an onium salt acid generator.

As the onium salt acid generator, a compound represented by general formula (b-1) below (hereafter, sometimes referred to as "component (b-1)"), a compound represented by general formula (b-2) below (hereafter, sometimes referred to as "component (b-2)") or a compound represented by general formula (b-3) below (hereafter, sometimes referred to as "component (b-3)") may be used.

[Chemical Formula 31]

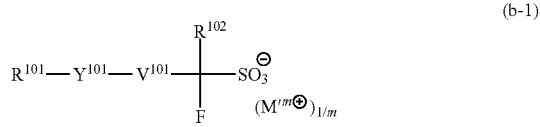

(b-1)

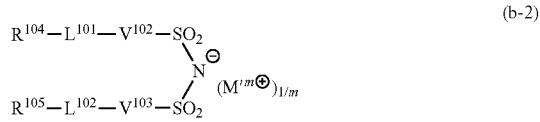

(b-2)

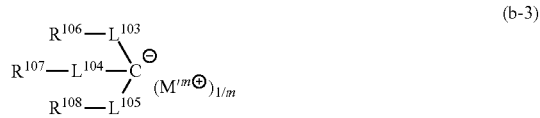

(b-3)

In the formulae, $R^{101}$ and $R^{104}$ to $R^{108}$ each independently represents a cyclic group which may have a substituent, a chain-like alkyl group which may have a substituent or a chain-like alkenyl group which may have a substituent, provided that $R^{104}$ and $R^{105}$ may be mutually bonded to form a ring; $R^{106}$ to $R^{108}$ may be mutually bonded to form a ring; $R^{102}$ represents a fluorine atom or a fluorinated alkyl group of 1 to 5 carbon atoms; $Y^{101}$ represents a single bond or a divalent linking group containing an oxygen atom; $V^{101}$ to $V^{103}$ each independently represents a single bond, an alkylene group, a fluorinated alkylene group, an arylene group or a fluorinated arylene group; $L^{101}$ and $L^{102}$ each independently represents a single bond or an oxygen atom; $L^{103}$ to $L^{105}$ each independently represents a single bond, —CO— or —SO$_2$—; and m represents an integer of 1 or more; $M^{m+}$ represents an organic cation having a valency of m (provided that the cation moiety of the compound (b0) is excluded).

{Anion Moiety}

Anion Moiety of Component (b-1)

In the formula (b-1), $R^{101}$ represents a cyclic group which may have a substituent, a chain-like alkyl group which may have a substituent or a chain-like alkenyl group which may have a substituent.

Cyclic Group which May have a Substituent

The cyclic group is preferably a cyclic hydrocarbon group, and the cyclic hydrocarbon group may be either an aromatic hydrocarbon group or an aliphatic hydrocarbon group.

As the aromatic hydrocarbon group for $R^{101}$, groups in which one hydrogen atom has been removed from an aromatic hydrocarbon ring (benzene, biphenyl, fluorene, naphthalene, anthracene, phenanthrene or the like) described above in relation to the divalent aromatic hydrocarbon group for $Va^1$ in the formula (a1-1) can be mentioned, and a phenyl group or a naphthyl group is preferable.

As the cyclic aliphatic hydrocarbon group for $R^{101}$, groups in which one hydrogen atom has been removed from a monocycloalkane or a polycycloalkane exemplified above in the explanation of the divalent aliphatic hydrocarbon group (alicyclic hydrocarbon group) for $Va^1$ in the formula (a1-1) can be mentioned. Among polycycloalkanes, a polycycloalkane having a bridged ring polycyclic skeleton, such as an adamantyl group or a norbornyl group, and a polycycloalkane having a condensed ring polycyclic skeleton, such as a cyclic group having a steroid skeleton are preferable. In the present specification, a steroid skeleton refers to a skeleton (st) represented by the chemical formula shown below which has three 6-membered rings and one 5-membered ring bonded.

[Chemical Formula 32]

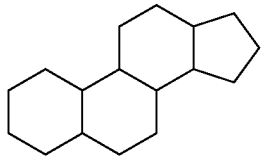

(st)

Further, the cyclic hydrocarbon group for $R^{101}$ may contain a hetero atom like as a heterocycle, and specific examples thereof include lactone-containing cyclic groups represented by the aforementioned general formulas (a2-r-1) to (a2-r-7), —$SO_2$— containing cyclic groups represented by the aforementioned formulas (a5-r-1) to (a5-r-4) and heterocycles shown below.

[Chemical Formula 33]

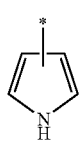
(r-hr-1)

(r-hr-2)

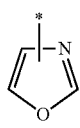
(r-hr-3)

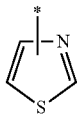
(r-hr-4)

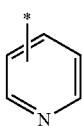
(r-hr-5)

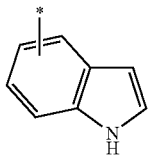
(r-hr-6)

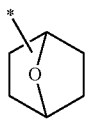
(r-hr-7)

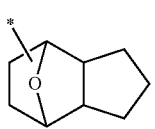
(r-hr-8)

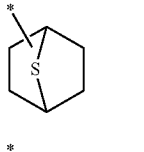
(r-hr-9)

(r-hr-10)

(r-hr-11)

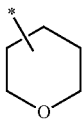
(r-hr-12)

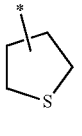
(r-hr-13)

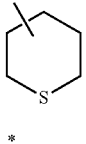
(r-hr-14)

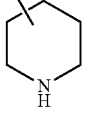
(r-hr-15)

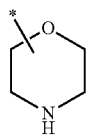
(r-hr-16)

As the substituent for the cyclic hydrocarbon group for $R^{101}$, an alkyl group, an alkoxy group, a halogen atom, a halogenated alkyl group, a hydroxyl group, a carbonyl group, a nitro group or the like can be used.

The alkyl group as the substituent is preferably an alkyl group of 1 to 5 carbon atoms, and more preferably a methyl group, an ethyl group, a propyl group, an n-butyl group or a tert-butyl group.

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Example of the aforementioned halogenated alkyl group includes a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

Chain-Like Alkyl Group which May have a Substituent

The chain-like alkyl group for $R^{101}$ may be linear or branched.

The linear alkyl group preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched alkyl group preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

Chain-Like Alkenyl Group which May have a Substituent

The chain-like alkenyl group for $R^{101}$ may be linear or branched, and preferably has 2 to 10 carbon atoms, more preferably 2 to 5 carbon atoms, still more preferably 2 to 4 carbon atoms, and most preferably 3 carbon atoms. Examples of linear alkenyl groups include a vinyl group, a propenyl group (an allyl group) and a butynyl group. Examples of branched alkenyl groups include a 1-methylpropenyl group and a 2-methylpropenyl group.

Among the above-mentioned examples, as the chain-like alkenyl group, a propenyl group is particularly desirable.

As the substituent for the chain-like alkyl group or alkenyl group for $R^{101}$, an alkoxy group, a halogen atom, a halogenated alkyl group, a hydroxyl group, a carbonyl group, a nitro group, an amino group, a cyclic group for $R^{101}$ or the like can be used.

Among these examples, as $R^{101}$, a cyclic group which may have a substituent is preferable, and a cyclic hydrocarbon group which may have a substituent is more preferable. Specifically, a phenyl group, a naphthyl group, a group in which one or more hydrogen atoms have been removed from a polycycloalkane, a lactone-containing cyclic group represented by any one of the aforementioned formula (a2-r-1) to (a2-r-7), and an —$SO_2$— containing cyclic group represented by any one of the aforementioned formula (a5-r-1) to (a5-r-4).

In formula (b-1), $Y^{101}$ represents a single bond or a divalent linking group containing an oxygen atom.

In the case where $Y^{101}$ is a divalent linking group containing an oxygen atom, $Y^{101}$ may contain an atom other than an oxygen atom. Examples of atoms other than an oxygen atom include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an oxycarbonyl group (—O—C(=O)—), an amido bond (—C(=O)—NH—), a carbonyl group (—C(=O)—) and a carbonate bond (—O—C(=O)—O—); and combinations of the aforementioned non-hydrocarbon, hetero atom-containing linking groups with an alkylene group. Furthermore, the combinations may have a sulfonyl group (—$SO_2$—) bonded thereto. As the combination, the linking group represented by formulas (y-a1-1) to (y-a1-7) shown below can be mentioned.

[Chemical Formula 34]

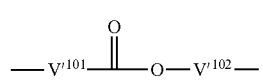
(y-a1-1)

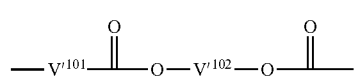
(y-a1-2)

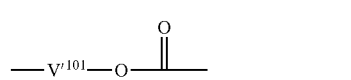
(y-a1-3)

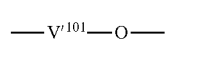
(y-a1-4)

(y-a1-5)

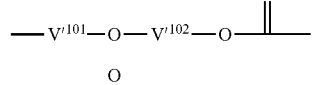
(y-a1-6)

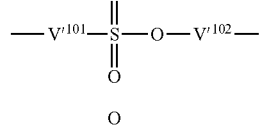
(y-a1-7)

In the formulae, $V'^{101}$ represents a single bond or an alkylene group of 1 to 5 carbon atoms; $V'^{102}$ represents a divalent saturated hydrocarbon group of 1 to 30 carbon atoms.

The divalent saturated hydrocarbon group for $V'^{102}$ is preferably an alkylene group of 1 to 30 carbon atoms.

The alkylene group for $V'^{101}$ and $V'^{102}$ may be a linear alkylene group or a branched alkylene group, and a linear alkylene group is preferable.

Specific examples of the alkylene group for $V'^{101}$ and $V'^{102}$ include a methylene group [—$CH_2$—]; an alkylmethylene group, such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$— and —$C(CH_2CH_3)_2$—; an ethylene group [—$CH_2CH_2$—]; an alkylethylene group, such as —$CH(CH_3)CH_2$—, —$CH(CH_3)CH(CH_3)$—, —$C(CH_3)_2CH_2$— and —$CH(CH_2CH_3)CH_2$—; a trimethylene group (n-propylene group) [—$CH_2CH_2CH_2$—]; an alkyltrimethylene group, such as —$CH(CH_3)CH_2CH_2$— and —$CH_2CH(CH_3)CH_2$—; a tetramethylene group [—$CH_2CH_2CH_2CH_2$—]; an alkyltetramethylene group, such as —$CH(CH_3)CH_2CH_2CH_2$—, —$CH_2CH(CH_3)CH_2CH_2$—; and a pentamethylene group [—$CH_2CH_2CH_2CH_2CH_2$—].

Further, part of methylene group within the alkylene group for $V'^{101}$ and $V'^{102}$ may be substituted with a divalent aliphatic cyclic group of 5 to 10 carbon atoms. The aliphatic cyclic group is preferably a divalent group in which one hydrogen atom has been removed from the cyclic aliphatic hydrocarbon group for $Ra^{t3}$ in the aforementioned formula (a1-r-1), and a cyclohexylene group, 1,5-adamantylene group or 2,6-adamantylene group is preferable.

Among the above examples, $Y'^{101}$ is preferably a divalent linking group containing an ether bond or an ester bond, and more preferably a group represented by any of the aforementioned formulae (y-a1-1) to (y-a1-5).

In formula (b-1), $V^{101}$ represents a single bond, an alkylene group, a fluorinated alkylene group, an arylene group or a fluorinated arylene group. The alkylene group and the fluorinated alkylene group for $V^{101}$ preferably has 1 to 4 carbon atoms. Examples of the fluorinated alkylene group for $V^{101}$ include a group in which part or all of the hydrogen atoms within the alkylene group for $V^{101}$ have been substituted with fluorine. Examples of the arylene group for $V^{101}$ include groups in which one hydrogen atom has been removed from an aryl group given as an example of the aromatic hydrocarbon group for $R^{101}$ in the aforementioned formula (b-1). Examples of the fluorinated arylene group for $V^{101}$ include a group in which part or all of the hydrogen atoms within the arylene group for $V^{101}$ have been substituted with fluorine.

Among these examples, as $V^{101}$, a single bond or a fluorinated alkylene group of 1 to 4 carbon atoms is preferable.

In formula (b-1), $R^{102}$ represents a fluorine atom or a fluorinated alkyl group of 1 to 5 carbon atoms. $R^{102}$ is preferably a fluorine atom or a perfluoroalkyl group of 1 to 5 carbon atoms, and more preferably a fluorine atom.

As specific examples of anion moieties of the formula (b-1), fluorinated alkylsulfonate anions such as a trifluoromethanesulfonate anion or a perfluorobutanesulfonate anion when $Y^{101}$ is a single bond, and anions represented by formulae (an-1) to (an-3) shown below when $Y^{101}$ is a divalent linking group containing an oxygen atom can be mentioned.

[Chemical Formula 35]

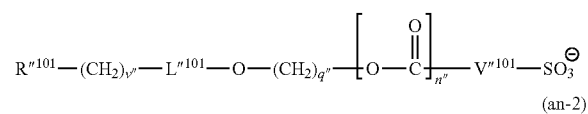

(an-1)

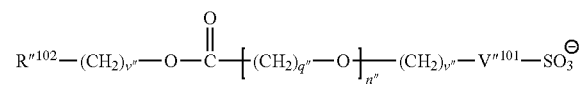

(an-2)

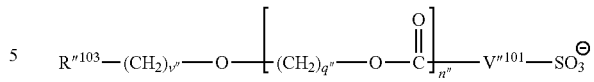

(an-3)

In the formulae, $R'''^{101}$ represents an aliphatic cyclic group which may have a substituent, a group represented by any one of the aforementioned formulae (r-hr-1) to (r-hr-6) or a chain-like alkyl group which may have a substituent; $R'''^{102}$ represents an aliphatic cyclic group which may have a substituent, a lactone-containing cyclic group represented by any one of the aforementioned general formulae (a2-r-1) to (a2-r-7) or an —$SO_2$— containing cyclic group represented by any one of the aforementioned general formulae (a5-r-1) to (a5-r-4); $R'''^{103}$ represents an aromatic cyclic group which may have a substituent, an aliphatic cyclic group which may have a substituent or a chain-like alkenyl group which may have a substituent; $V'''^{101}$ represents a fluorinated alkylene group; $L'''^{101}$ represents —$C(=O)$— or —$SO_2$—; $v''$ represents an integer of 0 to 3; $q''$ represents an integer of 1 to 20; and $n''$ represents 0 or 1.

As the aliphatic cyclic group for $R'''^{101}$, $R'''^{102}$ and $R'''^{103}$ which may have a substituent, the same groups as the cyclic aliphatic hydrocarbon group for $R^{101}$ described above are preferable. As the substituent, the same groups as those described above for substituting the cyclic aliphatic hydrocarbon group for $R^{101}$ can be mentioned.

As the aromatic cyclic group for $R'''^{103}$ which may have a substituent, the same groups as the aromatic hydrocarbon group for the cyclic hydrocarbon group represented by $R^{101}$ described above are preferable. The substituent is the same as defined for the substituent for the aromatic hydrocarbon group represented by $R^{101}$.

As the chain-like alkyl group for $R'''^{101}$ which may have a substituent, the same groups as those described above for $R^{101}$ are preferable. As the chain-like alkenyl group for $R'''^{103}$ which may have a substituent, the same groups as those described above for $R^{101}$ are preferable. $V'''^{101}$ is preferably a fluorinated alkylene group of 1 to 3 carbon atoms, and most preferably —$CF_2$—, —$CF_2CF_2$—, —$CHFCF_2$—, —$CF(CF_3)CF_2$— or —$CH(CF_3)CF_2$—.

Anion Moiety of Component (b-2)

In formula (b-2), $R^{104}$ and $R^{105}$ each independently represents a cyclic group which may have a substituent, a chain-like alkyl group which may have a substituent or a chain-like alkenyl group which may have a substituent, and is the same as defined for $R^{101}$ in formula (b-1). $R^{104}$ and $R^{105}$ may be mutually bonded to form a ring.

As $R^{104}$ and $R^{105}$, a chain-like alkyl group which may have a substituent is preferable, and a linear or branched alkyl group or a linear or branched fluorinated alkyl group is more preferable.

The chain-like alkyl group preferably has 1 to 10 carbon atoms, more preferably 1 to 7 carbon atoms, and still more preferably 1 to 3 carbon atoms. The smaller the number of carbon atoms of the chain-like alkyl group for $R^{104}$ and $R^{105}$, the more the solubility in a resist solvent is improved. Further, in the chain-like alkyl group for $R^{104}$ and $R^{105}$, it is preferable that the number of hydrogen atoms substituted with fluorine atoms is as large as possible because the acid strength increases and the transparency to high energy radiation of 200 nm or less or electron beam is improved. The fluorination ratio of the chain-like alkyl group is preferably from 70 to 100%, more preferably from 90 to 100%, and it is particularly desirable that the chain-like alkyl group be a perfluoroalkyl group in which all hydrogen atoms are substituted with fluorine atoms.

In formula (b-2), $V^{102}$ and $V^{103}$ each independently represents a single bond, an alkylene group or a fluorinated alkylene group, and is the same as defined for $V^{101}$ in formula (b-1).

In formula (b-2), $L^{101}$ and $L^{102}$ each independently represents a single bond or an oxygen atom.

Anion Moiety of Component (b-3)

In formula (b-3), $R^{106}$ to $R^{108}$ each independently represents a cyclic group which may have a substituent, a chain-like alkyl group which may have a substituent or a chain-like alkenyl group which may have a substituent, and is the same as defined for $R^{101}$ in formula (b-1).

$L^{103}$ to $L^{105}$ each independently represents a single bond, —CO— or —SO$_2$—.

{Cation Moiety}

In formulae (b-1), (b-2) and (b-3), $M^{m+}$ represents an organic cation having a valency of m other than the cation moiety of the compound (b0) (m represents an integer of 1 or more). Among these examples, a sulfonium cation or an iodonium cation is preferable, and a cation represented by any of general formulae (ca-1) to (ca-4) shown below is particularly desirable.

[Chemical Formula 36]

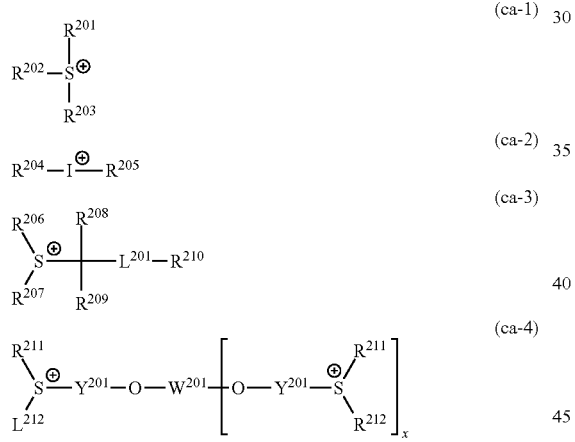

In the formulae, $R^{201}$ to $R^{207}$, $R^{211}$ and $R^{212}$ independently represents an aryl group which may have a substituent, an alkyl group which may have a substituent, or an alkenyl group which may have a substituent, provided that two of $R^{201}$ to $R^{203}$, $R^{206}$ and $R^{207}$, or $R^{211}$ and $R^{212}$ may be mutually bonded to form a ring with the sulfur atom; $R^{208}$ and $R^{209}$ each independently represents a hydrogen atom or an alkyl group of 1 to 5 carbon atoms; $R^{210}$ represents an aryl group which may have a substituent, an alkyl group which may have a substituent, an alkenyl group which may have a substituent, or an —SO$_2$— containing cyclic group which may have a substituent; $L^{201}$ represents —C(=O)— or —C(=O)—O—; $Y^{201}$ each independently represents an arylene group, an alkylene group or an alkenylene group; x represents 1 or 2; and $W^{201}$ represents a linking group having a valency of (x+1).

As the aryl group for $R^{201}$ to $R^{207}$, $R^{211}$ and $R^{212}$, an unsubstituted aryl group of 6 to 20 carbon atoms can be mentioned, and a phenyl group or a naphthyl group is preferable.

The alkyl group for $R^{201}$ to $R^{207}$, $R^{211}$ and $R^{212}$ is preferably a chain-like or cyclic alkyl group having 1 to 30 carbon atoms.

The alkenyl group for $R^{201}$ to $R^{207}$, $R^{211}$ and $R^{212}$ preferably has 2 to 10 carbon atoms.

Specific examples of the substituent which $R^{201}$ to $R^{207}$ and $R^{210}$ to $R^{212}$ may have include an alkyl group, a halogen atom, a halogenated alkyl group, a carbonyl group, a cyano group, an amino group, an aryl group, an arylthio group and groups represented by formulae (ca-r-1) to (ca-r-7) shown below.

The aryl group within the arylthio group as the substituent is the same as defined for $R^{101}$, and specific examples include a phenylthio group and a biphenylthio group.

[Chemical Formula 37]

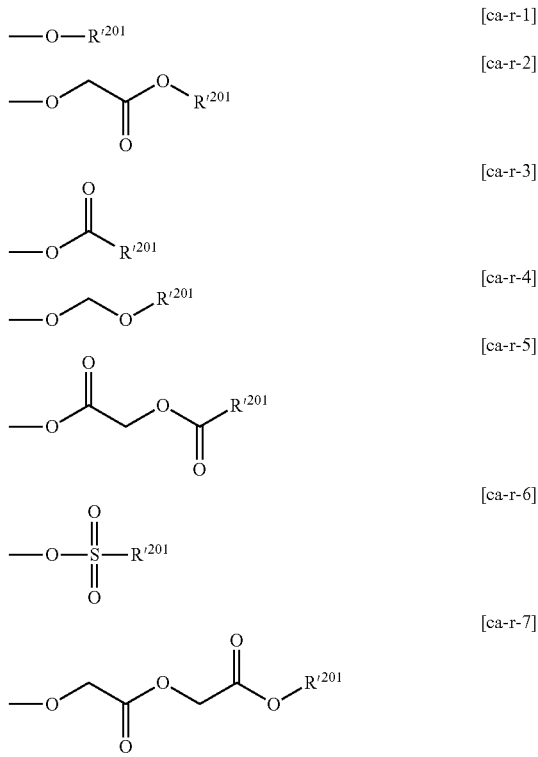

In the formulae, each $R'^{201}$ independently represents a hydrogen atom, a cyclic group which may have a substituent, a chain-like alkyl group which may have a substituent, or a chain-like alkenyl group which may have a substituent.

As the cyclic group which may have a substituent, the chain-like alkyl group which may have a substituent and the chain-like alkenyl group which may have a substituent for $R'^{201}$, the same groups as those described above for $R^{101}$ can be mentioned. As the cyclic group which may have a substituent and chain-like alkyl group which may have a substituent, the same groups as those described above for the acid dissociable group represented by the aforementioned formula (a1-r-2) can be also mentioned.

When $R^{201}$ to $R^{203}$, $R^{206}$, $R^{207}$, $R^{211}$ and $R^{212}$ are mutually bonded to form a ring with the sulfur atom, these groups may be mutually bonded via a hetero atom such as a sulfur atom, an oxygen atom or a nitrogen atom, or a functional group such as a carbonyl group, —SO—, —SO$_2$—, —SO$_3$—, —COO—, —CONH— or —N(R$_N$)— (wherein R$_N$ represents an alkyl group of 1 to 5 carbon atoms). The ring containing the sulfur atom in the skeleton thereof is preferably a 3 to 10-membered ring, and most preferably a 5 to 7-membered ring. Specific examples of the ring formed include a thiophene ring, a thiazole ring, a benzothiophene ring, a thianthrene ring, a benzothiophene ring, a dibenzothiophene ring, a 9H-thioxanthene ring, a thioxanthone ring, a phenoxathiin ring, a tetrahydrothiophenium ring, and a tetrahydrothiopyranium ring.

$R^{208}$ and $R^{209}$ each independently represents a hydrogen atom or an alkyl group of 1 to 5 carbon atoms, preferably a hydrogen atom or an alkyl group of 1 to 3 carbon atoms, and when $R^{208}$ and $R^{209}$ each represents an alkyl group, $R^{208}$ and $R^{209}$ may be mutually bonded to form a ring.

$R^{210}$ represents an aryl group which may have a substituent, an alkyl group which may have a substituent, an alkenyl group which may have a substituent, or an —$SO_2$— containing cyclic group which may have a substituent.

Examples of the aryl group for $R^{210}$ include an unsubstituted aryl group of 6 to 20 carbon atoms, and a phenyl group or a naphthyl group is preferable.

As the alkyl group for $R^{210}$, a chain-like or cyclic alkyl group having 1 to 30 carbon atoms is preferable.

The alkenyl group for $R^{210}$ preferably has 2 to 10 carbon atoms.

As the —$SO_2$— containing cyclic group for $R^{210}$ which may have a substituent, the same "—$SO_2$— containing cyclic groups" as those described above for $Ra^{21}$ in the aforementioned general formula (a2-1) can be mentioned, and the group represented by the aforementioned general formula (a5-r-1) is preferable.

Each $Y^{201}$ independently represents an arylene group, an alkylene group or an alkenylene group.

Examples of the arylene group for $Y^{201}$ include groups in which one hydrogen atom has been removed from an aryl group given as an example of the aromatic hydrocarbon group for $R^{101}$ in the aforementioned formula (b-1).

The alkylene group and the alkenylene group for $Y^{201}$ is the same as defined for the aliphatic hydrocarbon group (saturated or unsaturated) as the divalent linking group represented by $Va^1$ in the aforementioned general formula (a1-1).

In the formula (ca-4), x represents 1 or 2.

$W^{201}$ represents a linking group having a valency of (x+1), i.e., a divalent or trivalent linking group.

As the divalent linking group for $W^{201}$, a divalent hydrocarbon group which may have a substituent is preferable, and as examples thereof, the same hydrocarbon groups as those described above for $Ya^{21}$ in the general formula (a2-1) can be mentioned. The divalent linking group for $W^{201}$ may be linear, branched or cyclic, and cyclic is more preferable. Among these, an arylene group having two carbonyl groups, each bonded to the terminal thereof is preferable. Examples of the arylene group include a phenylene group and a naphthylene group, and a phenylene group is particularly desirable.

As the trivalent linking group for $W^{201}$, a group in which one hydrogen atom has been removed from the aforementioned divalent linking group for $W^{201}$ and a group in which the divalent linking group has been bonded to another divalent linking group can be mentioned. The trivalent linking group for $W^{201}$ is preferably a group in which 2 carbonyl groups are bonded to an arylene group.

Specific examples of preferable cations represented by formula (ca-1) include cations represented by formulae (ca-1-1) to (ca-1-63) shown below.

[Chemical Formula 38]

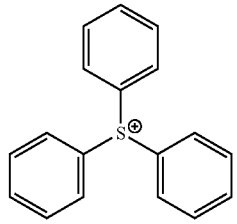
(ca-1-1)

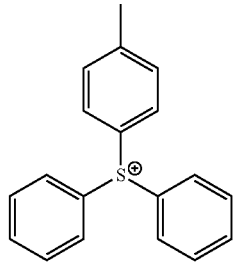
(ca-1-2)

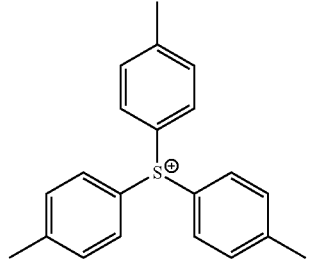
(ca-1-3)

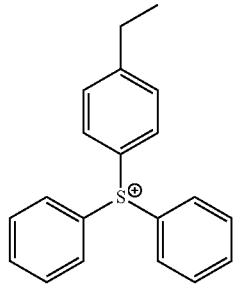
(ca-1-4)

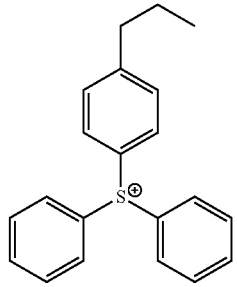
(ca-1-5)

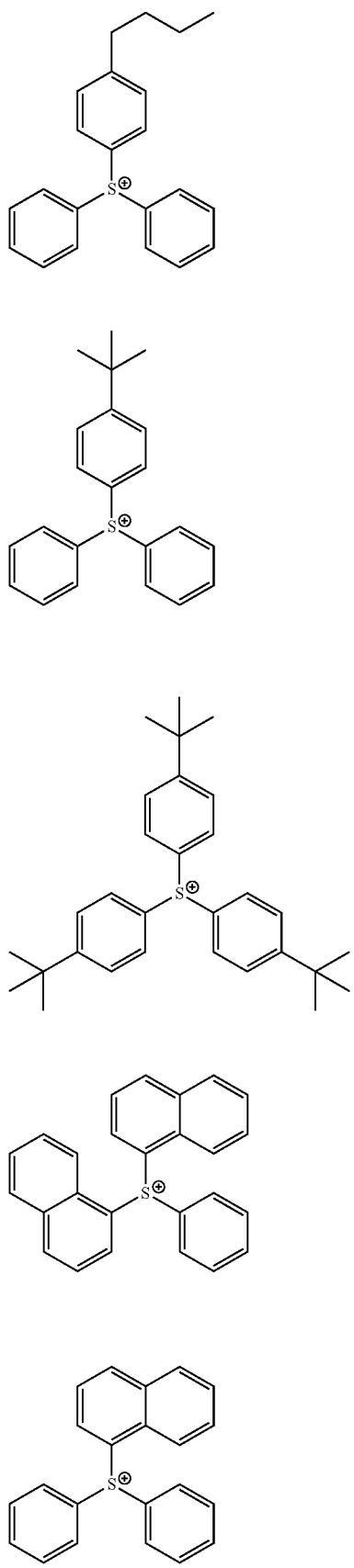
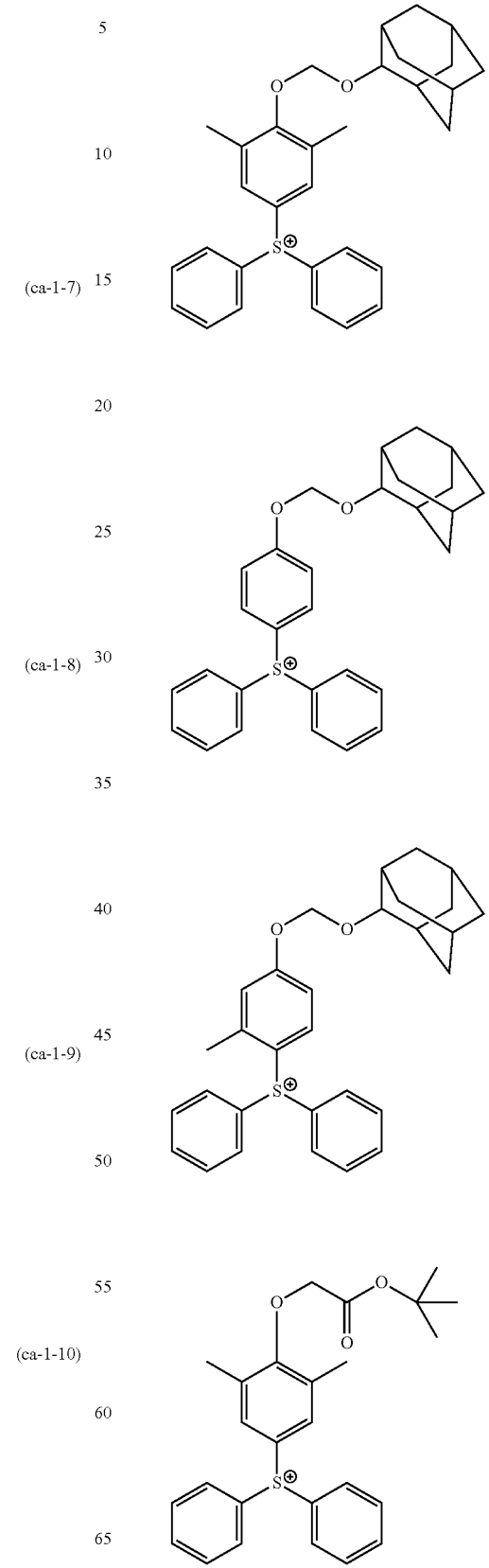

(ca-1-15)
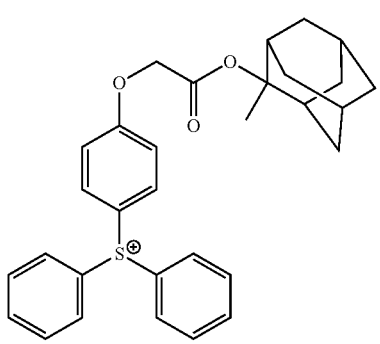
(ca-1-16)
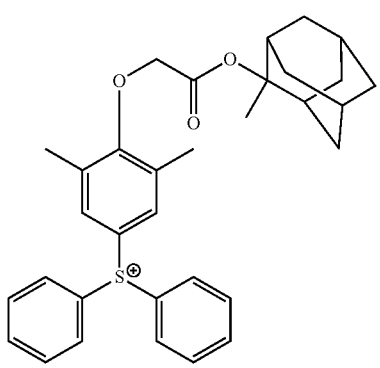
[Chemical Formula 39]
(ca-1-17)
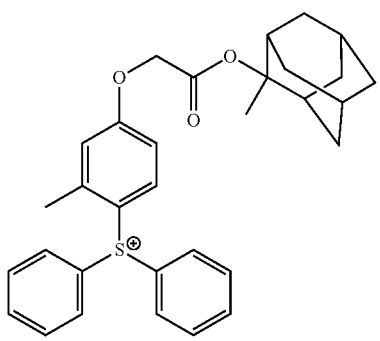
(ca-1-18)
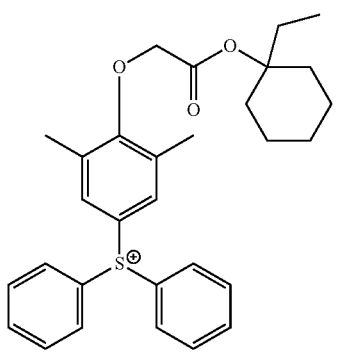
(ca-1-19)
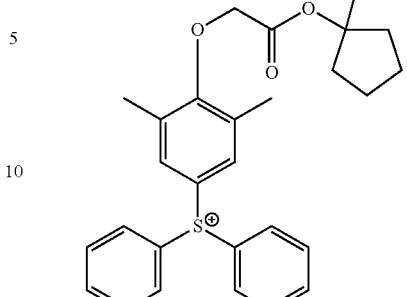
(ca-1-20)
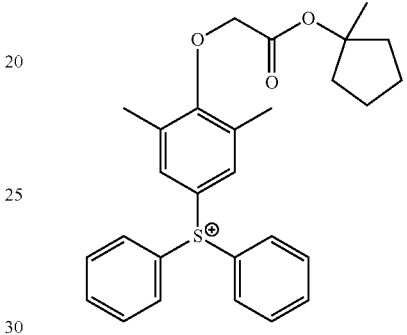
(ca-1-21)
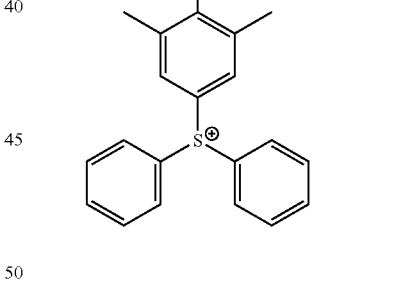
(ca-1-22)
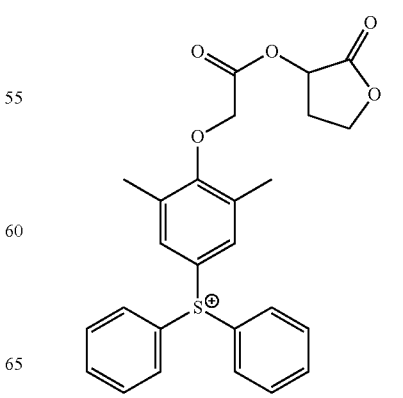

-continued
(ca-1-23)
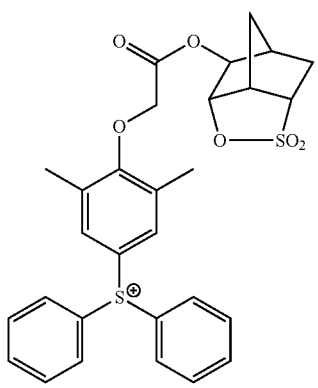
(ca-1-24)
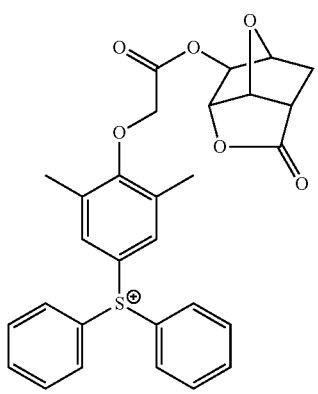
(ca-1-25)
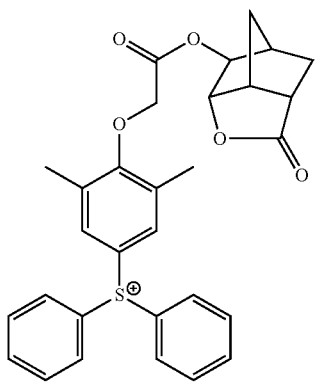
(ca-1-26)
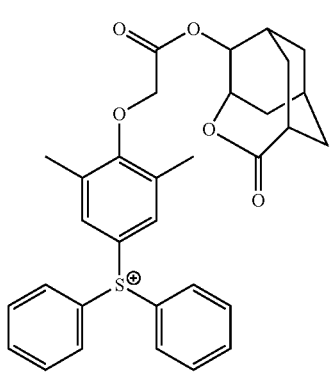
-continued
(ca-1-27)
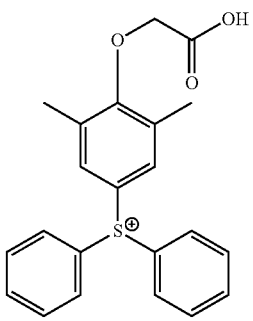
(ca-1-28)
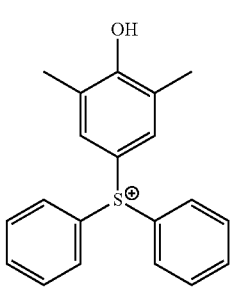
(ca-1-29)
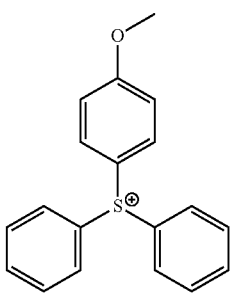
(ca-1-30)
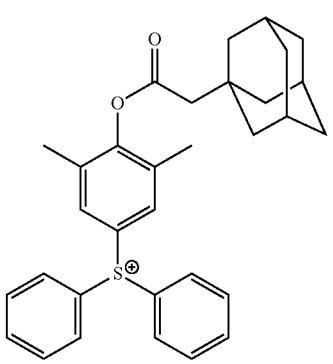
(ca-1-31)

(ca-1-32)
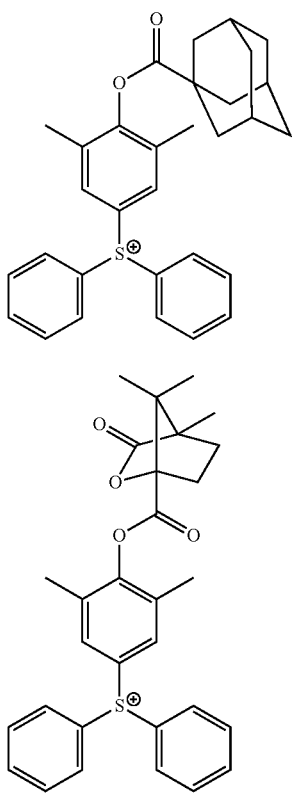
(ca-1-33)
[Chemical Formula 40]
(ca-1-34)
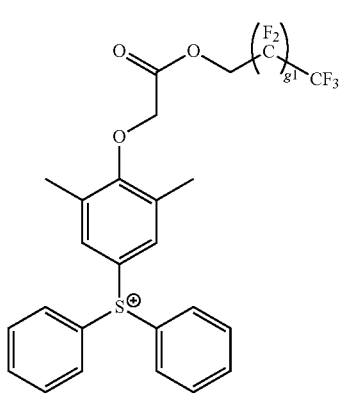
(ca-1-35)
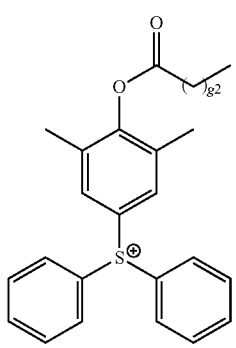
(ca-1-36)
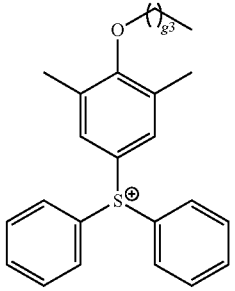
(ca-1-37)
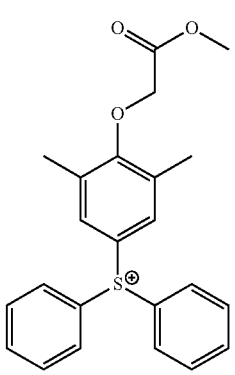
(ca-1-38)
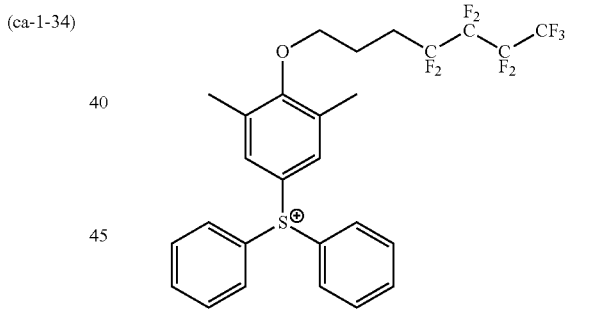
(ca-1-39)
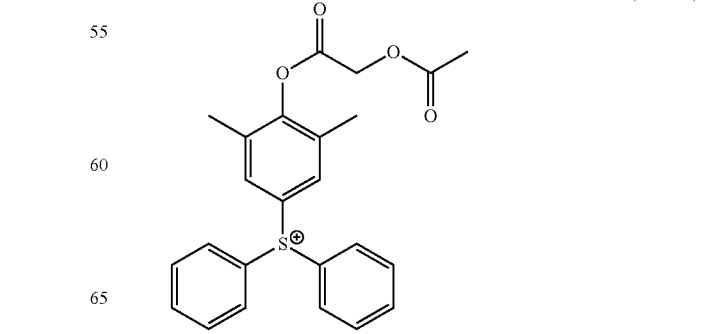

(ca-1-40)
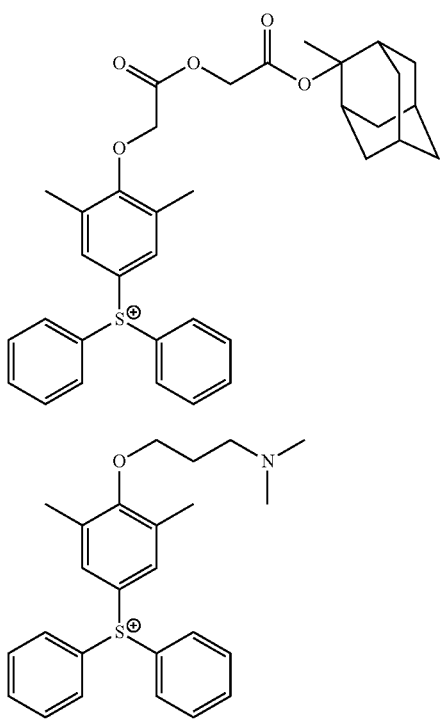
(ca-1-47)
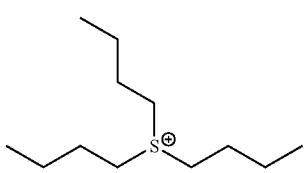
(ca-1-41)
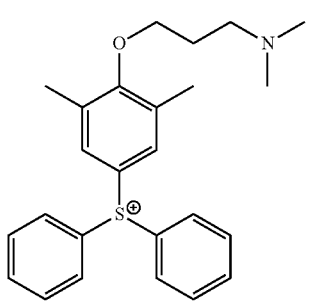
(ca-1-48)
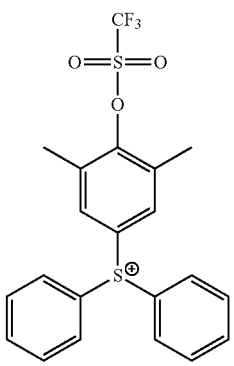
In the formulae, g1, g2 and g3 represent recurring numbers, wherein g1 is an integer of 1 to 5, g2 is an integer of 0 to 20, and g3 is an integer of 0 to 20.
[Chemical Formula 41]
(ca-1-42)
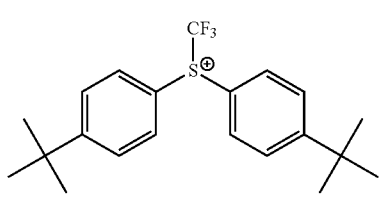
(ca-1-49)
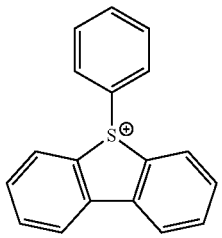
(ca-1-43)
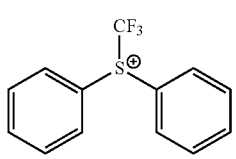
(ca-1-50)
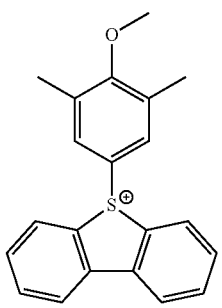
(ca-1-44)
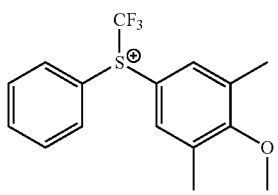
(ca-1-45)
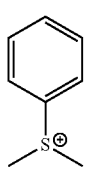
(ca-1-51)
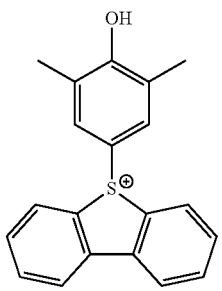
(ca-1-46)

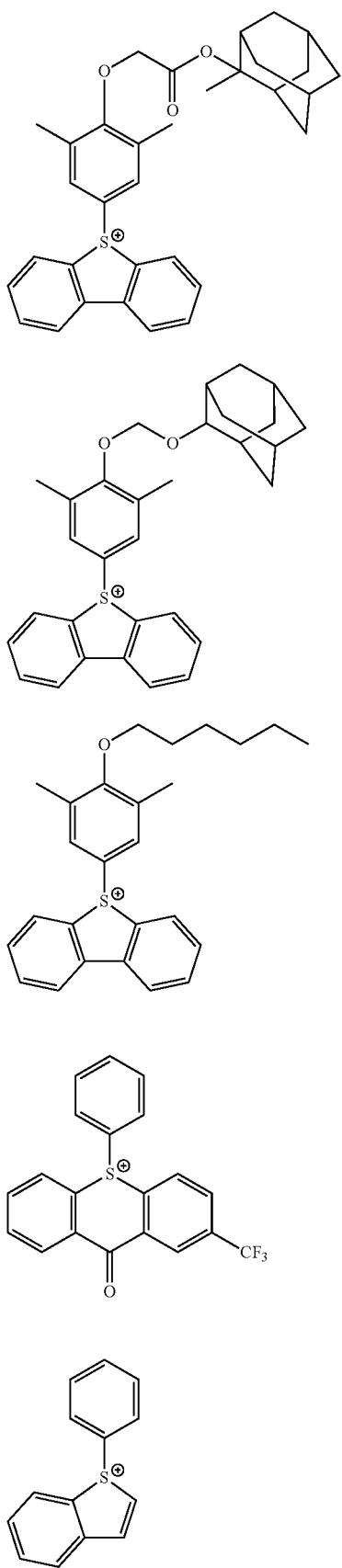
(ca-1-52)
(ca-1-53)
(ca-1-54)
(ca-1-55)
(ca-1-56)
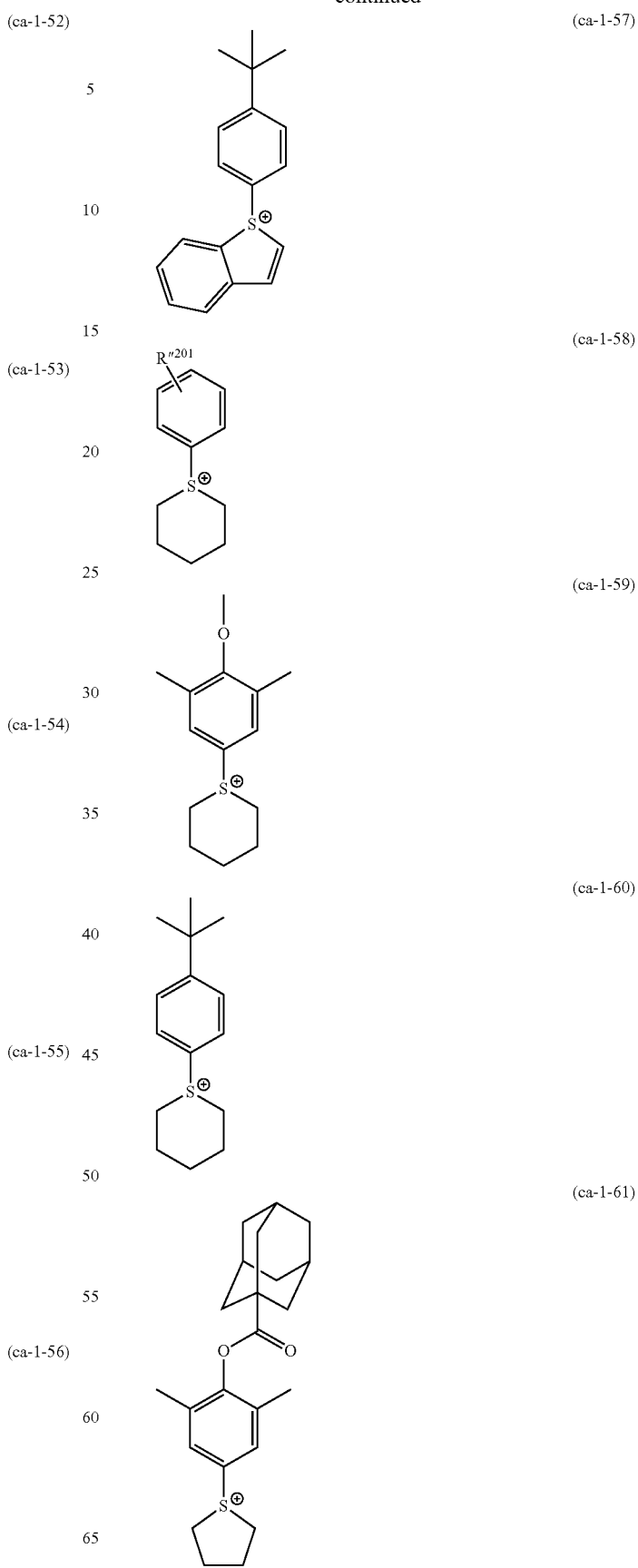
(ca-1-57)
(ca-1-58)
(ca-1-59)
(ca-1-60)
(ca-1-61)

-continued (ca-1-62)

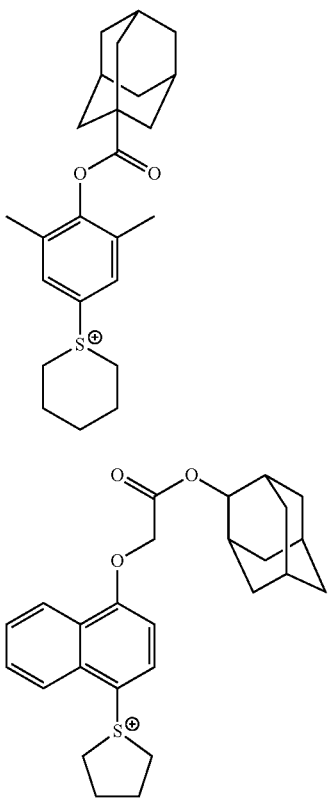

(ca-1-63)

In the formulae, R"²⁰¹ represents a hydrogen atom or a substituent, and as the substituent, the same groups as those described above for substituting R²⁰¹ to R²⁰⁷ and R²¹⁰ to R²¹² can be mentioned.

Specific examples of preferable cations represented by the formula (ca-2) include a dihphenyliodonium cation and a bis(4-tert-butylphenyl)iodonium cation.

Specific examples of preferable cations represented by formula (ca-3) include cations represented by formulae (ca-3-1) to (ca-3-6) shown below.

[Chemical Formula 42]

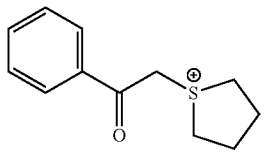
(ca-3-1)

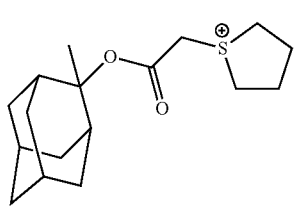
(ca-3-2)

-continued

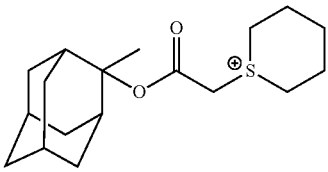
(ca-3-3)

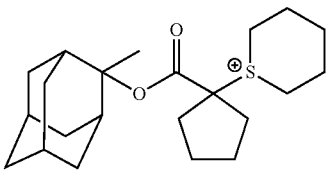
(ca-3-4)

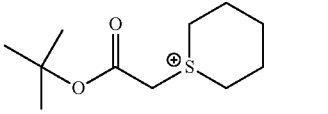
(ca-3-5)

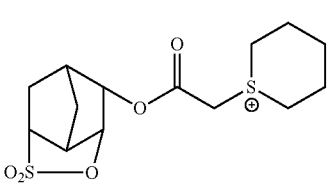
(ca-3-6)

Specific examples of preferable cations represented by formula (ca-4) include cations represented by formulae (ca-4-1) and (ca-4-2) shown below.

[Chemical Formula 43]

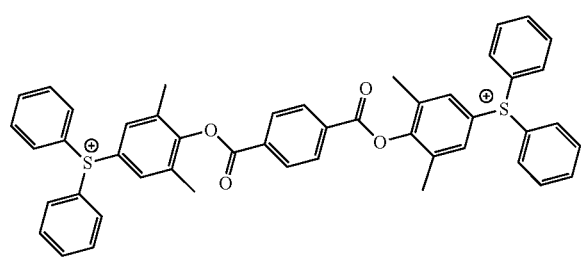
(ca-4-1)

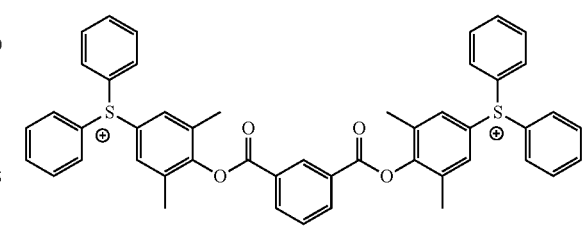
(ca-4-2)

As the component (B1), one type of compound may be used alone, or two or more types of compounds may be used in combination.

When the first resist composition contains the component (B1), the amount of the component (B1) relative to 100 parts by weight of the component (A) is preferably within a range from 0.5 to 60 parts by weight, more preferably from 1 to 50 parts by weight, and still more preferably from 1 to 40 parts by weight. When the amount of the component (B1) is within the above-mentioned range, formation of a resist pattern can be satisfactorily performed. Further, by virtue of the above-mentioned range, when each of the components are dissolved in an organic solvent, a uniform solution can be obtained and the storage stability becomes satisfactory.

[Optional Components]

The first resist composition may contain, in addition to the aforementioned component (A) and (B), any other components. Examples of the other components include the component (D), the component (E), the component (F) and the component (S) described below.

(Component (D): Acid Diffusion Control Agent)

The first resist composition preferably contains, in addition to the component (A) and the component (B), an acid diffusion control agent (D) (hereafter, referred to as "component (D)"). The component (D) functions as an acid diffusion control agent, i.e., a quencher which traps the acid generated in the resist composition upon exposure.

Furthermore, in the first resist composition, the component (D) preferably contains a compound represented by general formula (d0) shown below (hereafter, referred to as "compound (d0)").

[Chemical Formula 44]

(d0)

In formula (d0), $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group; and X2 represents a monovalent organic anion capable of generating a weak acid.

In formula (d0), $R^1$, $R^2$, $R^3$ and $V^1$ are the same as defined for $R^1$, $R^2$, $R^3$ and $V^1$ in the aforementioned formula (m0).

In formula (d0), X2⁻ represents an organic anion capable of generating a weak acid.

A "weak acid" refers to an acid having an acid dissociation constant (pKa) of more than 0, and preferably 0.2 or more. The upper limit of the pKa of the weak acid is not particularly limited, but is practically about 10.

Examples of the organic anion capable of generating a weak acid include the anion moieties of compounds represented by general formulae (d1-1) to (d1-3) described later, and the anion moiety of a compound represented by general formula (d1-2) is preferable.

As the compound (d0), one kind of compound may be used alone, or two or more compounds may be used in combination.

When the first resist composition contains the compound (d0), the amount of the compound (d0) relative to 100 parts by weight of the component (A) is preferably within a range from 0.1 to 30 parts by weight, more preferably from 0.3 to 20 parts by weight, and still more preferably from 0.5 to 15 parts by weight.

When the amount of the compound (d0) is at least as large as the lower limit of the above-mentioned range, excellent lithography properties and excellent resist pattern shape can be more reliably obtained. On the other hand, when the amount of the compound (d0) is no more than the upper limit of the above-mentioned range, sensitivity can be maintained at a satisfactory level, and through-put becomes excellent.

In the component (D), the amount of the compound (d0) based on the total weight of the component (D) is preferably 50% by weight or more, more preferably 75% by weight or more, and may be even 100% by weight. The amount of the component (d0) is most preferably 100% by weight. When the amount of the compound (d0) within the component (D) is at least as large the lower limit of the above preferable range, the resist composition can reliably achieve both reduction of roughness and mask reproducibility, and a resist pattern with further improved lithography properties can be formed. In addition, the solubility in a solvent and the sensitivity are also improved.

In the first resist composition, as the component (D), an acid diffusion control agent other than the compound (d0) may be used in combination with the compound (d0).

The acid diffusion control agent other than the compound (d0) is not particularly limited as long it does not fall under the definition of the compound (d0), and any of the known acid diffusion control agents used in conventional chemically amplified resist compositions can be used.

Examples of such acid diffusion control agents include a photodecomposable base (D1) (hereafter, referred to as "component (D1)") which is decomposed upon exposure and then loses the ability of controlling of acid diffusion, and a nitrogen-containing organic compound (D2) (hereafter, referred to as "component (D2)") which does not fall under the definition of component (D1). Among these examples, it is preferable to use a component (D1).

Component (D1)

When a resist pattern is formed using a resist composition containing the component (D1), the contrast between exposed portions and unexposed portions is further improved.

The component (D1) is not particularly limited, as long as it is decomposed upon exposure and then loses the ability of controlling of acid diffusion. As the component (D1), at least one compound selected from the group consisting of a compound represented by general formula (d1-1) shown below (hereafter, referred to as "component (d1-1)"), a compound represented by general formula (d1-2) shown below (hereafter, referred to as "component (d1-2)") and a compound represented by general formula (d1-3) shown below (hereafter, referred to as "component (d1-3)") is preferably used.

At exposed portions, the components (d1-1), (d1-2) and (d1-3) are decomposed and then lose the ability of controlling of acid diffusion (i.e., basicity), and therefore the components (d1-1), (d1-2) and (d1-3) cannot function as a quencher, whereas at unexposed portions, the components (d1-1) to (d1-3) functions as a quencher.

[Chemical Formula 45]

(d1-1)

(d1-2)

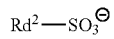

(d1-3)

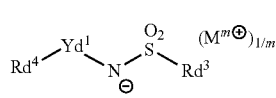

In the formulae, $Rd^1$ to $Rd^4$ represent a cyclic group which may have a substituent, a chain-like alkyl group which may have a substituent or a chain-like alkenyl group which may have a substituent, provided that, the carbon atom adjacent to the sulfur atom within the $Rd^2$ in the formula (d1-2) has no fluorine atom bonded thereto; $Yd^1$ represents a single bond or a divalent linking group; and m represents an integer of 1 or more; each $M^{m+}$ independently represents an organic cation having a valency of m (provided that the cation moiety of the compound (d0) is excluded).

{Component (d1-1)}
Anion Moiety:

In formula (d1-1), $Rd^1$ represents a cyclic group which may have a substituent, a chain-like alkyl group which may have a substituent or a chain-like alkenyl group which may have a substituent, and is the same groups as those defined above for $R^{101}$.

Among these, as the group for $Rd^1$, an aromatic hydrocarbon group which may have a substituent, an aliphatic cyclic group which may have a substituent and a chain-like alkyl group which may have a substituent are preferable. Examples of the substituent for these groups include a hydroxy group, an oxo group, an alkyl group, an aryl group, a fluorine atom, a fluorinated alkyl group, a lactone-containing cyclic group represented by any one of the aforementioned formulae (a2-r-1) to (a2-r-7), an ether bond, an ester bond, and a combination thereof. In the case where an ether bond or an ester bond is included as the substituent, the substituent may be bonded via an alkylene group, and a linking group represented by any one of the aforementioned formulae (y-a1-1) to (y-a1-5) is preferable.

The aromatic hydrocarbon group is preferably an aryl group such as a phenyl group or a naphthyl group.

Examples of the aliphatic cyclic group include groups in which one or more hydrogen atoms have been removed from a polycycloalkane such as adamantane, norbornane, isobornane, tricyclodecane or tetracyclododecane.

The chain-like alkyl group preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl or a decyl group, and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group or a 4-methylpentyl group.

In the case where the chain-like alkyl group is a fluorinated alkyl group having a fluorine atom or a fluorinated alkyl group, the fluorinated alkyl group preferably has 1 to 11 carbon atoms, more preferably 1 to 8 carbon atoms, and still more preferably 1 to 4 carbon atoms. The fluorinated alkyl group may contain an atom other than fluorine. Examples of the atom other than fluorine include an oxygen atom, a hydrogen atom, a sulfur atom and a nitrogen atom.

As $Rd^1$, a fluorinated alkyl group in which part or all of the hydrogen atoms constituting a linear alkyl group have been substituted with fluorine atom(s) is preferable, and a fluorinated alkyl group in which all of the hydrogen atoms constituting a linear alkyl group have been substituted with fluorine atoms (i.e., a linear perfluoroalkyl group) is particularly desirable.

Specific examples of preferable anion moieties for the component (d1-1) are shown below.

[Chemical Formula 46]

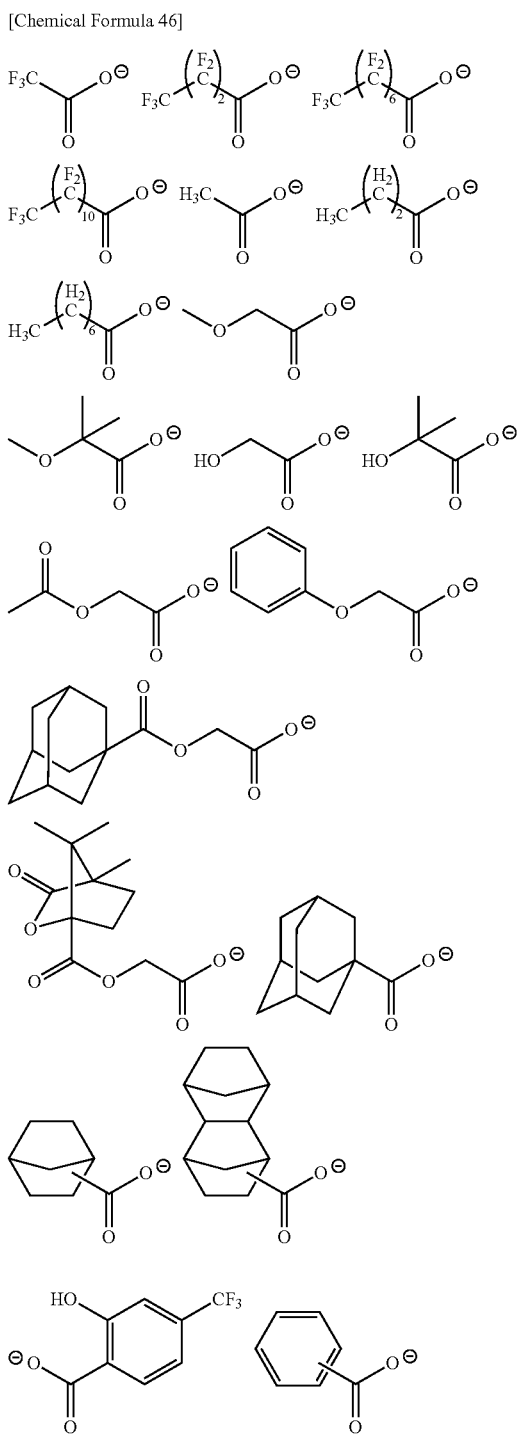

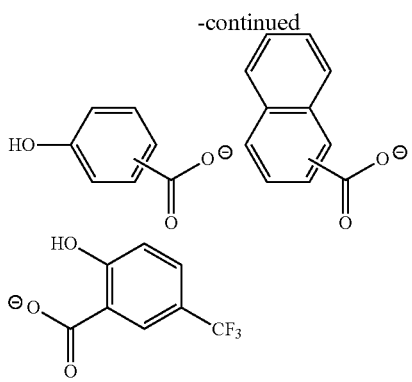

Cation Moiety:

In formula (d1-1), $M^{m+}$ represents an organic cation having a valency of m other than the cation moiety of the compound (d0) (m represents an integer of 1 or more).

Preferable examples of the organic cation for $M^{m+}$ include the same cation moieties as those represented by the aforementioned general formulae (ca-1) to (ca-4), and cation moieties represented by the aforementioned formulae (ca-1-1) to (ca-1-63).

As the component (d1-1), one type of compound may be used, or two or more types of compounds may be used in combination.

{Component (d1-2)}

Anion Moiety:

In formula (d1-2), $Rd^2$ represents a cyclic group which may have a substituent, a chain-like alkyl group which may have a substituent or a chain-like alkenyl group which may have a substituent, and is the same groups as those defined above for $R^{101}$, provided that, the carbon atom adjacent to the sulfur atom within $Rd^2$ group has no fluorine atom bonded thereto (i.e., the carbon atom adjacent to the sulfur atom within $Rd^2$ group does not substituted with a fluorine atom). As a result, the anion of the component (d1-2) becomes an appropriately weak acid anion, thereby improving the quenching ability of the component (D).

As $Rd^2$, an aliphatic cyclic group which may have a substituent is preferable, and a group in which one or more hydrogen atoms have been removed from adamantane, norbornane, isobornane, tricyclodecane, tetracyclododecane or camphor (which may have a substituent) is more preferable.

The hydrocarbon group for $Rd^2$ may have a substituent. As the substituent, the same groups as those described above for substituting the hydrocarbon group (e.g., aromatic hydrocarbon group, aliphatic cyclic group, alkyl group, alkenyl group) for $Rd^1$ in the formula (d1-1) can be mentioned.

Specific examples of preferable anion moieties for the component (d1-2) are shown below.

[Chemical Formula 47]

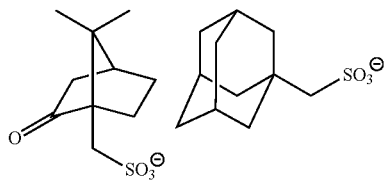

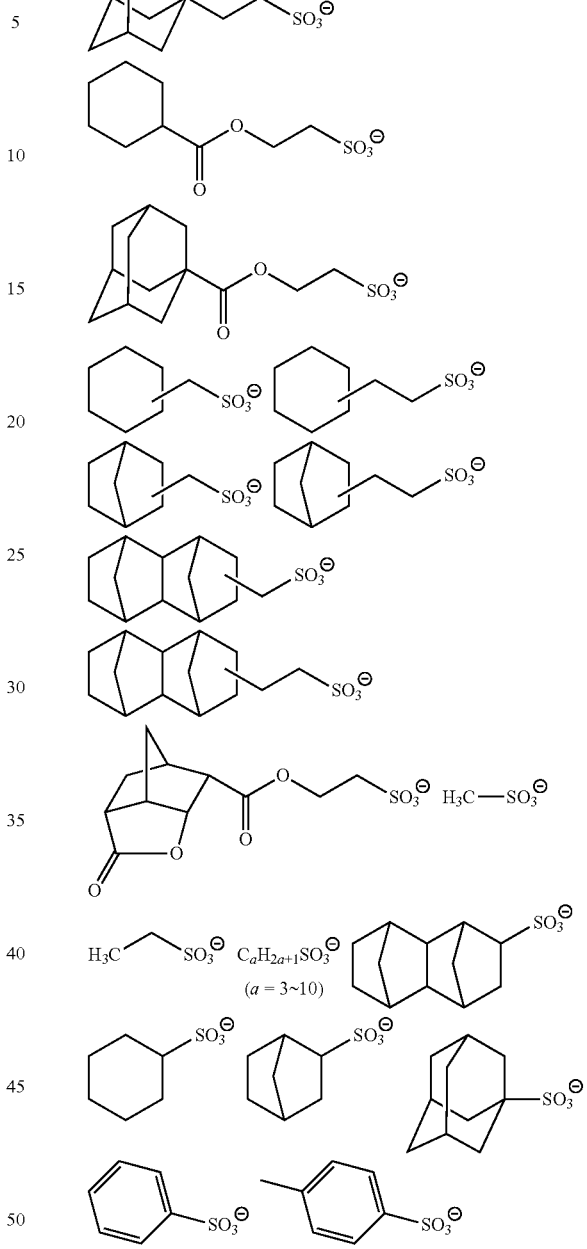

Cation Moiety:

In formula (d1-2), $M^{m+}$ represents an organic cation having a valency of m other than the cation moiety of the compound (d0) (m represents an integer of 1 or more), and is the same as defined for $M^{m+}$ in the aforementioned formula (d1-1).

As the component (d1-2), one type of compound may be used, or two or more types of compounds may be used in combination.

{Component (d1-3)}

Anion Moiety:

In formula (d1-3), $Rd^3$ represents a cyclic group which may have a substituent, a chain-like alkyl group which may have a substituent or a chain-like alkenyl group which may have a substituent, and is the same groups as those defined above for $R^{101}$, and a cyclic group containing a fluorine atom, a chain-like alkyl group or a chain-like alkenyl group is preferable. Among these, a fluorinated alkyl group is preferable, and more preferably the same fluorinated alkyl groups as those described above for $Rd^1$.

In formula (d1-3), $Rd^4$ represents a cyclic group which may have a substituent, a chain-like alkyl group which may have a substituent or a chain-like alkenyl group which may have a substituent, and is the same groups as those defined above for $R^{101}$.

Among these, an alkyl group which may have substituent, an alkoxy group which may have substituent, an alkenyl group which may have substituent or a cyclic group which may have substituent is preferable.

The alkyl group for $Rd^4$ is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neo-pentyl group. Part of the hydrogen atoms within the alkyl group for $Rd^4$ may be substituted with a hydroxy group, a cyano group or the like.

The alkoxy group for $Rd^4$ is preferably an alkoxy group of 1 to 5 carbon atoms, and specific examples thereof include a methoxy group, an ethoxy group, an n-propoxy group, an iso-propoxy group, an n-butoxy group and a tert-butoxy group. Among these, a methoxy group and an ethoxy group are preferable.

As the alkenyl group for $Rd^4$, the same groups as those described above for $R^{101}$ can be mentioned, and a vinyl group, a propenyl group (an allyl group), a 1-methylpropenyl group and a 2-methylpropenyl group are preferable.

These groups may have an alkyl group of 1 to 5 carbon atoms or a halogenated alkyl group of 1 to 5 carbon atoms as a substituent.

As the cyclic group for $Rd^4$, the same groups as those described above for $R^{101}$ can be mentioned. Among these, as the cyclic group, an alicyclic group (e.g., a group in which one or more hydrogen atoms have been removed from a cycloalkane such as cyclopentane, cyclohexane, adamantane, norbornane, isobornane, tricyclodecane or tetracyclododecane) or an aromatic group (e.g., a phenyl group or a naphthyl group) is preferable. When $Rd^4$ is an alicyclic group, the resist composition can be satisfactorily dissolved in an organic solvent, thereby improving the lithography properties. Alternatively, when $Rd^4$ is an aromatic group, the resist composition exhibits an excellent photoabsorption efficiency in a lithography process using EUV or the like as the exposure source, thereby resulting in the improvement of the sensitivity and the lithography properties.

In formula (d1-3), $Yd^1$ represents a single bond or a divalent linking group.

The divalent linking group for $Yd^1$ is not particularly limited, and examples thereof include a divalent hydrocarbon group (aliphatic hydrocarbon group, or aromatic hydrocarbon group) which may have a substituent and a divalent linking group containing a hetero atom. As such groups, the same divalent linking groups as those described above for $Ya^{21}$ in the formula (a2-1) can be mentioned.

As $Yd^1$, a carbonyl group, an ester bond, an amide bond, an alkylene group or a combination of these is preferable. As the alkylene group, a linear or branched alkylene group is more preferable, and a methylene group or an ethylene group is still more preferable.

Specific examples of preferable anion moieties for the component (d1-3) are shown below.

[Chemical Formula 48]

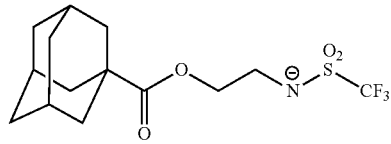

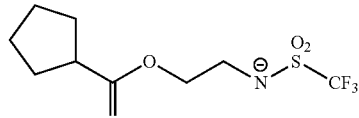

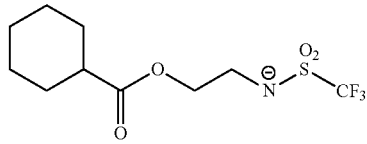

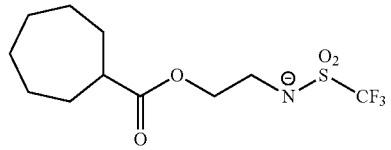

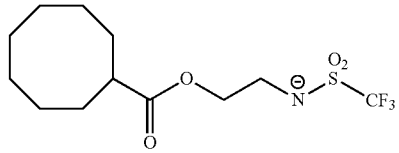

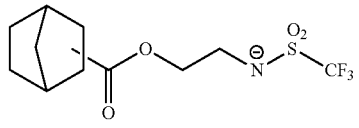

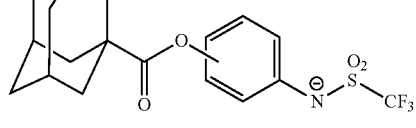

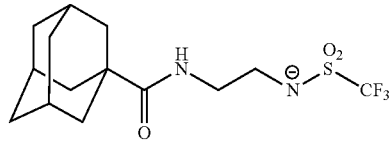

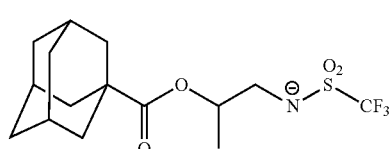

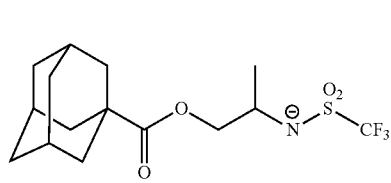

-continued

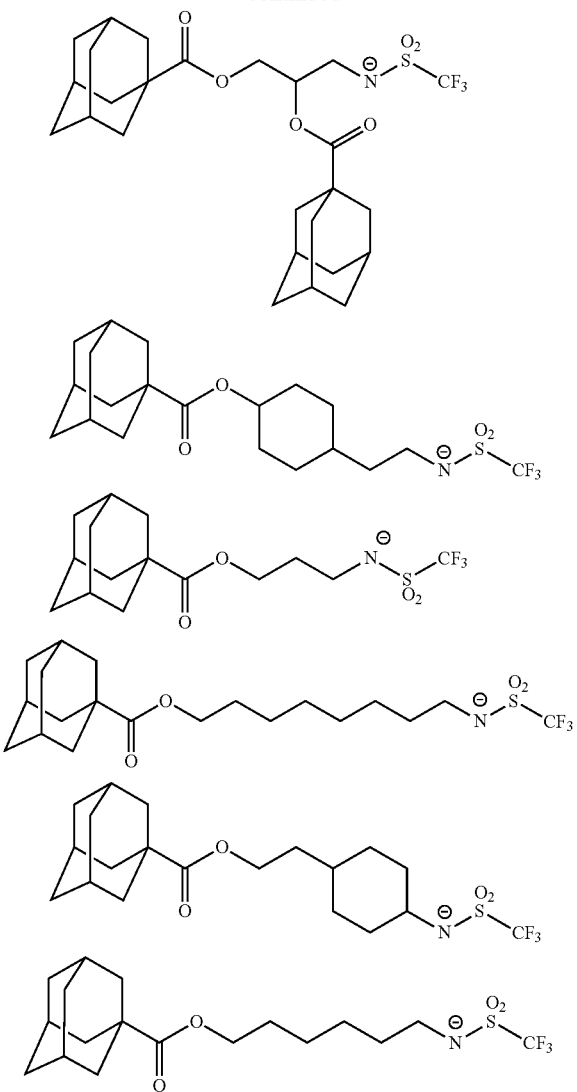

[Chemical Formula 49]

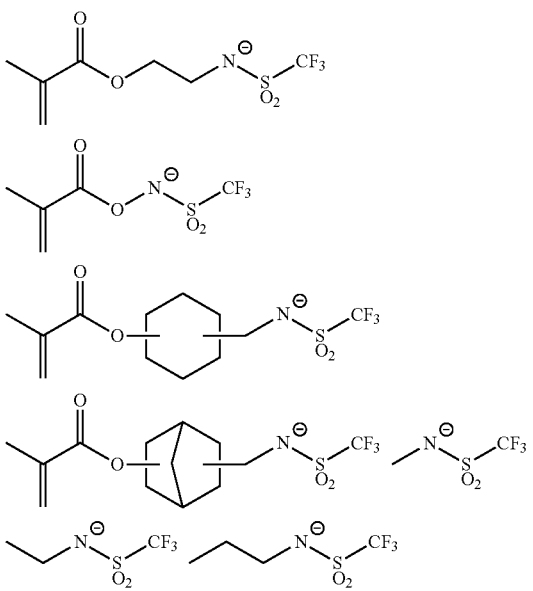

-continued

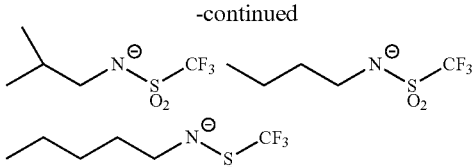

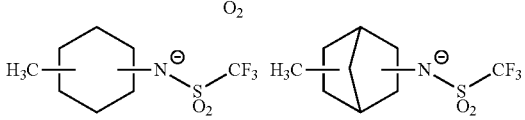

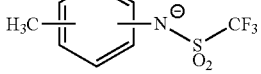

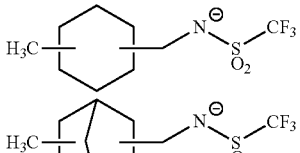

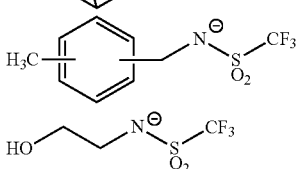

Cation Moiety:

In formula (d1-3), $M^{m+}$ represents an organic cation having a valency of m other than the cation moiety of the compound (d0) (m represents an integer of 1 or more), and is the same as defined for $M^{m+}$ in the aforementioned formula (d1-1).

As the component (d1-3), one type of compound may be used, or two or more types of compounds may be used in combination.

As the component (D1), one type of the aforementioned components (d1-1) to (d1-3), or at least two types of the aforementioned components (d1-1) to (d1-3) can be used in combination.

When the first resist composition contains the component (D1), the amount of the component (D1) relative to 100 parts by weight of the component (A) is preferably within a range from 0.5 to 10 parts by weight, more preferably from 0.5 to 8 parts by weight, and still more preferably from 1 to 8 parts by weight.

When the amount of the component (D1) is at least as large as the lower limit of the above-mentioned range, excellent lithography properties and excellent resist pattern shape can be more reliably obtained. On the other hand, when the amount of the component (D1) is no more than the upper limit of the above-mentioned range, sensitivity can be maintained at a satisfactory level, and through-put becomes excellent.

Component (D2)

The component (D) may contain a nitrogen-containing organic compound (D2) (hereafter, referred to as component (D2)) which does not fall under the definition of the compound (d0) and the component (D1).

The component (D2) is not particularly limited, as long as it functions as an acid diffusion control agent, and does not fall under the definition of the compound (d0) and the component (D1). As the component (D2), any of the conventionally known compounds may be selected for use. Among these, an aliphatic amine, particularly a secondary aliphatic amine or tertiary aliphatic amine is preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris {2-(2-methoxyethoxy)ethyl}amine, tris {2-(2-methoxyethoxymethoxy)ethyl}amine, tris {2-(1-methoxyethoxy)ethyl}amine, tris {2-(1-ethoxyethoxy)ethyl}amine, tris {2-(1-ethoxypropoxy)ethyl}amine, tris[2-{2-(2-hydroxyethoxy)ethoxy}ethyl]amine and triethanolamine triacetate, and triethanolamine triacetate is preferable.

Further, as the component (D2), an aromatic amine may be used.

Examples of aromatic amines include aniline, pyridine, 4-dimethylaminopyridine, pyrrole, indole, pyrazole, imidazole and derivatives thereof, as well as diphenylamine, triphenylamine, tribenzylamine, 2,6-diisopropylaniline and N-tert-butoxycarbonylpyrrolidine.

As the component (D2), one type of compound may be used alone, or two or more types may be used in combination.

The component (D2) is typically used in an amount within a range from 0.01 to 5.0 parts by weight, relative to 100 parts by weight of the component (A). When the amount of the component (D2) is within the above-mentioned range, the shape of the resist pattern and the post exposure stability of the latent image formed by the pattern-wise exposure of the resist layer are improved.

As the component (D), one type of compound may be used, or two or more types of compounds may be used in combination.

When the first resist composition contains the component (D), the total amount of the component (D) relative to 100 parts by weight of the component (A) is preferably within a range from 0.1 to 15 parts by weight, more preferably from 0.3 to 12 parts by weight, and still more preferably from 0.5 to 12 parts by weight. When the amount of the component (D) is at least as large as the lower limit of the above-mentioned range, various lithography properties (such as LWR) of the resist composition are improved. Further, a resist pattern having an excellent shape can be obtained. On the other hand, when the amount of the component (D) is no more than the upper limit of the above-mentioned range, sensitivity can be maintained at a satisfactory level, and through-put becomes excellent.

(Component (E): At Least One Compound Selected from the Group Consisting of Organic Carboxylic Acids, and Phosphorus Oxo Acids and Derivatives Thereof)

Furthermore, in the first resist composition, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters and phenylphosphinic acid.

As the component (E), one type may be used alone, or two or more types may be used in combination.

When the first resist composition contains the component (E), the component (E) is used in an amount within a range from 0.01 to 5 parts by weight, relative to 100 parts by weight of the component (A).

(Component (F): Fluorine Additive)

The first resist composition may contain a fluorine additive (hereafter, referred to as "component (F)") for imparting water repellency to the resist film.

As the component (F), for example, a fluorine-containing polymeric compound described in Japanese Unexamined Patent Application, First Publication No. 2010-002870, Japanese Unexamined Patent Application, First Publication No. 2010-032994, Japanese Unexamined Patent Application, First Publication No. 2010-277043, Japanese Unexamined Patent Application, First Publication No. 2011-13569, and Japanese Unexamined Patent Application, First Publication No. 2011-128226 can be used.

Specific examples of the component (F) include polymers having a structural unit (f1) represented by general formula (f1-1) shown below. As the polymer, a polymer (homopolymer) consisting of a structural unit (f1) represented by formula (f1-1) shown below; a copolymer of the structural unit (f1) and the aforementioned structural unit (a1); and a copolymer of the structural unit (f1), a structural unit derived from acrylic acid or methacrylic acid and the aforementioned structural unit (a1) are preferable. As the structural unit (a1) to be copolymerized with the structural unit (f1), a structural unit derived from 1-ethyl-1-cyclooctyl (meth)acrylate is preferable.

[Chemical Formula 50]

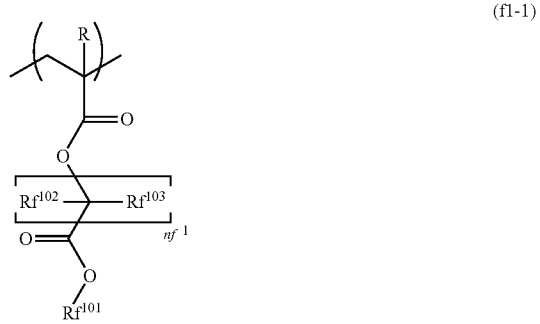

(f1-1)

In the formula, R is the same as defined above; $Rf^{102}$ and $Rf^{103}$ each independently represents a hydrogen atom, a halogen atom, an alkyl group of 1 to 5 carbon atoms, or a halogenated alkyl group of 1 to 5 carbon atoms, provided that $Rf^{102}$ and $Rf^{103}$ may be the same or different; $nf^1$ represents an integer of 1 to 5; and $Rf^{101}$ represents an organic group containing a fluorine atom.

In formula (f1-1), R bonded to the carbon atom on the α-position is the same as defined above. As R, a hydrogen atom or a methyl group is preferable.

In formula (f1-1), examples of the halogen atom for $Rf^{102}$ and $Rf^{103}$ include a fluorine atom, a chlorine atom, a bromine atom and an iodine atom, and a fluorine atom is particularly desirable. Examples of the alkyl group of 1 to 5 carbon atoms for $Rf^{102}$ and $R^{103}$ include the same alkyl group of 1 to 5 carbon atoms as those described above for R, and a methyl group or an ethyl group is preferable. Specific examples of the halogenated alkyl group of 1 to 5 carbon atoms represented by $Rf^{102}$ or $Rf^{103}$ include groups in which part or all of the hydrogen atoms of the aforementioned alkyl groups of 1 to 5 carbon atoms have been substituted with halogen atoms.

Examples of the halogen atom include a fluorine atom, a chlorine atom, a bromine atom and an iodine atom, and a fluorine atom is particularly desirable. Among these examples, as $Rf^{102}$ and $Rf^{103}$, a hydrogen atom, a fluorine atom or an alkyl group of 1 to 5 carbon atoms is preferable, and a hydrogen atom, a fluorine atom, a methyl group or an ethyl group is more preferable.

In formula (f1-1), $nf^1$ represents an integer of 1 to 5, preferably an integer of 1 to 3, and more preferably 1 or 2.

In formula (f1-1), $Rf^{101}$ represents an organic group containing a fluorine atom, and is preferably a hydrocarbon group containing a fluorine atom.

The hydrocarbon group containing a fluorine atom may be linear, branched or cyclic, and preferably has 1 to 20 carbon atoms, more preferably 1 to 15 carbon atoms, and most preferably 1 to 10 carbon atoms.

It is preferable that the hydrocarbon group having a fluorine atom has 25% or more of the hydrogen atoms within the hydrocarbon group fluorinated, more preferably 50% or more, and most preferably 60% or more, as the hydrophobicity of the resist film during immersion exposure is enhanced.

Among these, as $Rf^{101}$, a fluorinated hydrocarbon group of 1 to 5 carbon atoms is preferable, and a trifluoromethyl group, —$CH_2$—$CF_3$, —$CH_2$—$CF_2$—$CF_3$, —$CH(CF_3)_2$, —$CH_2$—$CH_2$—$CF_3$, and —$CH_2$—$CH_2$—$CF_2$—$CF_2$—$CF_2$—$CF_3$ are most preferable.

The weight average molecular weight (Mw) (the polystyrene equivalent value determined by gel permeation chromatography) of the component (F) is preferably 1,000 to 50,000, more preferably 5,000 to 40,000, and most preferably 10,000 to 30,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (F) is preferably 1.0 to 5.0, more preferably 1.0 to 3.0, and most preferably 1.2 to 2.5.

As the component (F), one type may be used alone, or two or more types may be used in combination.

When the first resist composition contains the component (F), the component (F) is used in an amount within a range from 0.5 to 10 parts by weight, relative to 100 parts by weight of the component (A).

If desired, other miscible additives can also be added to the first resist composition. Examples of such miscible additives include additive resins for improving the performance of the resist film, dissolution inhibitors, plasticizers, stabilizers, colorants, halation prevention agents, and dyes.

(Component (S): Organic Solvent)

The first resist composition can be prepared by dissolving the resist materials for the resist composition in an organic solvent (hereafter, frequently referred to as "component (S)").

The component (S) may be any organic solvent which can dissolve the respective components to give a homogeneous solution, and any organic solvent can be appropriately selected from those which have been conventionally known as solvents for a chemically amplified resist composition.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

The component (S) can be used individually, or in combination as a mixed solvent.

Among these, PGMEA, PGME, γ-butyrolactone, EL and cyclohexanone are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL or cyclohexanone is mixed as the polar solvent, the PGMEA:EL or cyclohexanone weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3. Furthermore, a mixed solvent of PGMEA, PGME and cyclohexanone is also preferable.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) is not particularly limited, and is appropriately adjusted to a concentration which enables coating of a coating solution to a substrate. In general, the component (S) is used in an amount such that the solid content of the resist composition becomes within the range from 1 to 20% by weight, and preferably from 2 to 15% by weight.

<Resist Composition of Second Embodiment>

The resist composition of second embodiment (hereafter, sometimes referred to as "second resist composition") is a resist composition which generates acid upon exposure and exhibits changed solubility in a developing solution under action of acid. In addition, the second resist composition contains the compound represented by the aforementioned general formula (d0) (compound (d0)) as an acid diffusion control agent (D) (component (D)).

The second resist composition exhibits an acid generating ability to generate acid upon exposure. Furthermore, the second resist composition preferably contains a base component (A) (component (A)) which exhibits changed solubility in a developing solution under action of acid, and the component (A) has the ability of generating acid upon exposure.

More specifically, the second resist composition may contain (1) a component (A) which generates acid upon exposure; or (2) a component (A) which generates acid upon exposure, and further containing an acid generator component (B).

[Component (A)]

In the case where the second resist composition is the aforementioned resist composition (1) or (2), preferable examples of the component (A) include a "base component which generates acid upon exposure and exhibits changed solubility in a developing solution under action of acid".

In the case where the component (A) is a base component which generates acid upon exposure and exhibits changed solubility in a developing solution under action of acid, the component (A1) which further includes a structural unit (a6) which generates acid upon exposure may be preferably used.

That is, in the second resist composition, the component (A) preferably contains a polymeric compound having the structural unit (a1) and a structural unit (a6) which generates acid upon exposure (hereafter, this polymeric compound is referred to as "polymeric compound (A11)").

(Structural Unit (a1))

The structural unit (a1) is the same as defined for the structural unit (a1) explained above in relation to the first resist composition (specific examples, amount, etc.).

(Structural Unit (a6))

The structural unit (a6) is a structural unit which generates acid upon exposure.

The structural unit (a6) is not particularly limited as long as it generates acid upon exposure. For example, a structural unit copolymerizable with the aforementioned structural unit (a1) and in which a structure proposed as an acid generator for a conventional chemically amplified resist has been introduced can be used.

Preferable examples of structural units copolymerizable with the structural unit (a1) include a structural unit derived from an acrylate ester which may have the hydrogen atom bonded to the carbon atom on the α-position substituted with a substituent, and a structural unit derived from hydroxystyrene or a hydroxystyrene derivative.

Preferable examples of a compound having a structure proposed as an acid generator for a conventional chemically amplified resist include the aforementioned component (B1).

Examples of the structural unit (a6) include a structural unit (a6c) having an anion group which generates an acid upon exposure on a side chain thereof, and a structural unit (a6c) which has a cation group that is decomposed upon exposure on a side chain thereof.

Structural Unit (a6a)

The structural unit (a6c) is a structural unit having an anion group which generates an acid upon exposure on a side chain thereof.

The anion group which generates acid upon exposure is not particularly limited, and a sulfonic acid anion, an amide anion or a methide anion is preferable.

Among these, as the anion group, a group represented by any one of general formulae (a6a-r-1), (a6a-r-2) or (a6a-r-3) shown below is preferable.

[Chemical Formula 51]

(a6a-r-1)

(a6a-r-2)

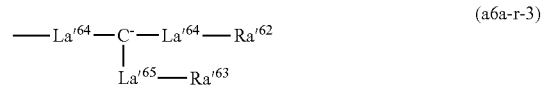

(a6a-r-3)

In the formulae, $Va'^{61}$ represents a divalent hydrocarbon group having a fluorine atom; $La'^{63}$ to $La'^{65}$ each independently represents —SO$_2$— or a single bond; $Ra'^{61}$ to $Ra'^{63}$ each independently represents a hydrocarbon group which may have a substituent.

In formula (a6a-r-1), $Va'^{61}$ represents a divalent hydrocarbon group having a fluorine atom. The divalent hydrocarbon group for $Va'^{61}$ may be either an aliphatic hydrocarbon group or an aromatic hydrocarbon group.

An "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof can be given.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—CH$_2$—], an ethylene group [—(CH$_2$)$_2$—], a trimethylene group [—(CH$_2$)$_3$—], a tetramethylene group [—(CH$_2$)$_4$—] and a pentamethylene group [—(CH$_2$)$_5$—].

As the branched aliphatic hydrocarbon group, branched alkylene groups are preferred, and specific examples include various alkylalkylene groups, including alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —C(CH$_2$CH$_3$)$_2$—CH$_2$—; alkyltrimethylene groups such as —CH(CH$_3$)CH$_2$CH$_2$—, and —CH$_2$CH(CH$_3$)CH$_2$—; and alkyltetramethylene groups such as —CH(CH$_3$)CH$_2$CH$_2$CH$_2$—, and —CH$_2$CH(CH$_3$)CH$_2$CH$_2$—. As the alkyl group within the alkylalkylene group, a linear alkyl group of 1 to 5 carbon atoms is preferable.

The linear or branched aliphatic hydrocarbon group has a fluorine atom, and all of the hydrogen atoms of the aliphatic hydrocarbon group may be substituted with fluorine. Further, in addition to fluorine, the aliphatic hydrocarbon group may be substituted with an oxo group (=O).

As examples of the hydrocarbon group containing a ring in the structure thereof, a cyclic aliphatic hydrocarbon group containing a hetero atom in the ring structure thereof and may have a substituent (a group in which two hydrogen atoms have been removed from an aliphatic hydrocarbon ring), a group in which the cyclic aliphatic hydrocarbon group is bonded to the terminal of the aforementioned chain-like aliphatic hydrocarbon group, and a group in which the cyclic aliphatic group is interposed within the aforementioned linear or branched aliphatic hydrocarbon group, can be given. As the linear or branched aliphatic hydrocarbon group, the same groups as those described above can be used.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The cyclic aliphatic hydrocarbon group has a fluorine atom, and all of the hydrogen atoms of the cyclic aliphatic hydrocarbon group may be substituted with fluorine. Further, in addition to fluorine, the cyclic aliphatic hydrocarbon group may be substituted with an alkyl group, an alkoxy group, a hydroxy group, an oxo group (=O) or the like.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

The aromatic hydrocarbon group for the divalent hydrocarbon group represented by Va'$^{61}$ is a hydrocarbon group having at least one aromatic ring.

The aromatic ring is not particularly limited, as long as it is a cyclic conjugated compound having (4n+2)π electrons, and may be either monocyclic or polycyclic. The aromatic ring preferably has 5 to 30 carbon atoms, more preferably 5 to 20, still more preferably 6 to 15, and most preferably 6 to 12. Here, the number of carbon atoms within a substituent(s) is not included in the number of carbon atoms of the aromatic hydrocarbon group.

Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group include a group in which two hydrogen atoms have been removed from the aforementioned aromatic hydrocarbon ring or aromatic hetero ring (arylene group or heteroarylene group); a group in which two hydrogen atoms have been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (a group in which one hydrogen atom has been removed from the aryl group within the aforementioned arylalkyl group such as a benzyl group, a phenethyl group, a 1-naphthylmethyl group, a 2-naphthylmethyl group, a 1-naphthylethyl group, or a 2-naphthylethyl group, or a heteroarylalkyl group). The alkylene group which is bonded to the aforementioned aryl group or heteroaryl group preferably has 1 to 4 carbon atoms, more preferably 1 or 2 carbon atoms, and most preferably 1 carbon atom.

The aromatic hydrocarbon group has a fluorine atom, and all of the hydrogen atoms of the aromatic hydrocarbon group may be substituted with fluorine. Further, in addition to fluorine, the cyclic aliphatic hydrocarbon group may be substituted with an alkyl group, an alkoxy group, a hydroxy group, an oxo group (=O) or the like. The alkyl group and the alkoxy group as the substituent are the same as defined for the alkyl group and the alkoxy group as the substituent for the cyclic aliphatic hydrocarbon group.

Among the anion groups represented by formula (a6a-r-1), a group represented by general formula (a6a-r-11) shown below is preferable.

[Chemical Formula 52]

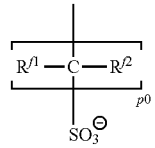

(a6a-r-11)

In the formula, R$^{f1}$ and R$^{f2}$ each independently represents a hydrogen atom, an alkyl group, a fluorine atom or a fluorinated alkyl group, provided that at least one of R$^{f1}$ and R$^{f2}$ represents a fluorine atom or a fluorinated alkyl group; and p0 represents an integer of 1 to 8.

In formula (a6a-r-11), each of $R^{f1}$ and $R^{f2}$ independently represents a hydrogen atom, an alkyl group, a fluorine atom or a fluorinated alkyl group, provided that at least one of $R^{f1}$ and $R^{f2}$ represents a fluorine atom or a fluorinated alkyl group.

The alkyl group for $R^{f1}$ and $R^{f2}$ is preferably an alkyl group of 1 to 5 carbon atoms, and specific examples thereof include a methyl group, an ethyl group, a propyl group, an isopropyl group, an n-butyl group, an isobutyl group, a tert-butyl group, a pentyl group, an isopentyl group and a neopentyl group.

The fluorinated alkyl group for $R^{f1}$ and $R^{f2}$ is preferably a group in which part or all of the hydrogen atoms within the aforementioned alkyl group for $R^{f1}$ and $R^{f2}$ have been substituted with a fluorine atom.

As $R^{f1}$ and $R^{f2}$, a fluorine atom or a fluorinated alkyl group is preferable.

In formula (a6a-r-11), p0 represents an integer of 1 to 8, preferably an integer of 1 to 4, and more preferably 1 or 2.

In formula (a6a-r-2), as the hydrocarbon group for $Ra'^{61}$, an alkyl group, a monovalent alicyclic hydrocarbon group, an aryl group and an aralkyl group can be mentioned.

The alkyl group for $Ra'^{61}$ preferably has 1 to 8 carbon atoms, more preferably 1 to 6 carbon atoms, and still more preferably 1 to 4 carbon atoms. The alkyl group may be linear or branched. Specific examples of preferable alkyl groups include a methyl group, an ethyl group, a propyl group, a butyl group, a hexyl group and an octyl group.

The monovalent alicyclic hydrocarbon group for $Ra'^{61}$ preferably has 3 to 20 carbon atoms, and more preferably 3 to 12 carbon atoms. The monovalent alicyclic hydrocarbon group may be polycyclic or monocyclic. As the monocyclic alicyclic hydrocarbon group, a group in which one or more hydrogen atoms have been removed from a monocycloalkane is preferable. The monocycloalkane preferably has 3 to 6 carbon atoms, and specific examples thereof include cyclobutane, cyclopentane and cyclohexane. As the polycyclic alicyclic hydrocarbon group, a group in which one or more hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The aryl group for $Ra'^{61}$ preferably has 6 to 18 carbon atoms, and more preferably 6 to 10 carbon atoms. Specifically, a phenyl group is particularly desirable.

As a preferable examples of the aralkyl group for $Ra'^{61}$, a group in which an alkylene group of 1 to 8 carbon atoms has been bonded to the aforementioned "aryl group for $Ra'^{61}$" can be mentioned. An aralkyl group in which an alkylene group of 1 to 6 carbon atoms has been bonded to the aforementioned "aryl group for $Ra'^{61}$" is more preferable, and an aralkyl group in which an alkylene group of 1 to 4 carbon atoms has been bonded to the aforementioned "aryl group for $Ra'^{61}$" is most preferable.

The hydrocarbon group for $Ra'^{61}$ may have a substituent, preferably has part or all of the hydrogen atoms within the hydrocarbon group substituted with fluorine, and the hydrocarbon group more preferably has 30 to 100% of the hydrogen atoms substituted with fluorine. Among these, a perfluoroalkyl group in which all of the hydrogen atoms within the alkyl group have been substituted with fluorine atoms is particularly desirable. In addition, the hydrocarbon group for $Ra'^{61}$ may have a methylene group ($-CH_2-$) substituted with a divalent group such as $-CO-$ or $-SO_2-$.

In formula (a6a-r-3), $La'^{63}$ to $La'^{65}$ each independently represents $-SO_2-$ or a single bond, and $Ra'^{62}$ and $Ra'^{63}$ each independently represents a hydrocarbon group which may have a substituent. The hydrocarbon group for $Ra'^{62}$ and $Ra'^{63}$ is the same as defined for the hydrocarbon group for $Ra'^{61}$ which may have a substituent.

Preferable examples of the structural unit (a6a) include structural units represented by general formulae (a6a-1) to (a6a-8) shown below.

[Chemical Formula 53]

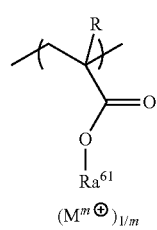
(a6a-1)

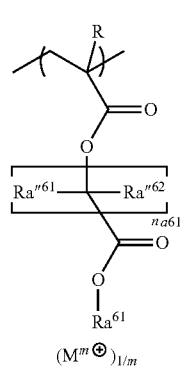
(a6a-2)

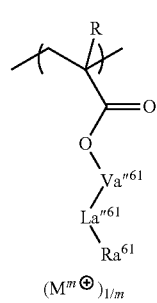
(a6a-3)

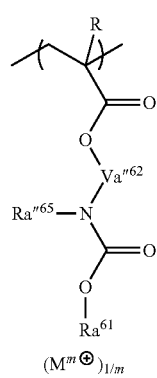
(a6a-4)

-continued (a6a-5)
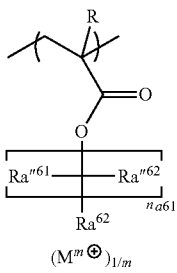

(a6a-6)
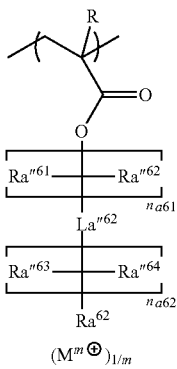

(a6a-7)
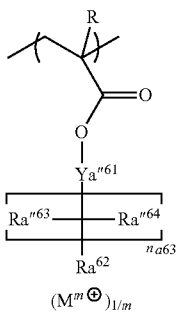

(a6a-8)
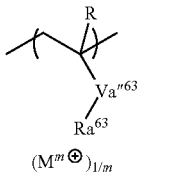

In the formula, R represents a hydrogen atom, an alkyl group of 1 to 5 carbon atoms or a halogenated alkyl group of 1 to 5 carbon atoms; $Ra^{61}$ is a group represented by the aforementioned formula (a6a-r-1); $Ra^{62}$ is a group represented by the aforementioned formula (a6a-r-2) or (a6a-r-3); $Ra^{63}$ is a group represented by the aforementioned formula (a6a-r-3); $Ra''^{61}$ to $Ra''^{64}$ each independently represents a hydrogen atom, a fluorine atom, an alkyl group of 1 to 5 carbon atoms or a fluorinated alkyl group; $n_{a61}$ and $n_{a62}$ each independently represents an integer of 1 to 10; $n_{a63}$ represents an integer of 0 to 10;

$Va''^{61}$ represents a divalent cyclic hydrocarbon group; $La''^{61}$ represents —C(=O)—O—, —O—C(=O)—O— or —O—CH$_2$—C(=O)—O—; $Va''^{62}$ represents a divalent hydrocarbon group; $Ra''^{65}$ represents a hydrogen atom or an alkyl group of 1 to 5 carbon atoms; $La''^{62}$ represents —C(=O)—O—, —O—C(=O)—O—, or —NH—C(=O)—O—; $Ya''^{61}$ represents a divalent linking group containing a cyclic hydrocarbon group; $Va''^{63}$ represents a divalent cyclic hydrocarbon group or a single bond; m represents an integer of 1 or more; and each $M^{m+}$ independently represents an organic cation having a valency of m.

In formulae (a6a-1) to (a6a-8), R is the same as defined for R in the aforementioned formula (a1-1).

In formulae (a6a-1) to (a6a-4), each $Ra^{61}$ independently represents a group represented by the aforementioned formula (a6a-r-1). In formulae (a6a-5) to (a6a-7), each $Ra^{62}$ independently represents a group represented by the aforementioned formula (a6a-r-2) or (a6a-r-3). In formula (a6a-8), $Ra^{63}$ represents a group represented by the aforementioned formula (a6a-r-3).

In formulae (a6a-2) and (a6a-5) to (a6a-7), $Ra''^{61}$ to $Ra''^{64}$ each independently represents a hydrogen atom, a fluorine atom, an alkyl group of 1 to 5 carbon atoms or a fluorinated alkyl group. Examples of the fluorinated alkyl group for $Ra''^{61}$ to $Ra''^{64}$ include groups in which part or all of the hydrogen atoms within the alkyl group of 1 to 5 carbon atoms have been substituted with a fluorine atom.

In formulae (a6a-2), (a6a-5) and (a6a-6), each $n_{a61}$ independently represents an integer of 1 to 10, preferably an integer of 1 to 8, more preferably an integer of 1 to 4, and still more preferably 1 or 2.

In formula (a6a-6), $n_{a62}$ represents an integer of 1 to 10, preferably an integer of 1 to 8, more preferably an integer of 1 to 4, and still more preferably 1 or 2.

In formula (a6a-7), $n_{a63}$ represents an integer of 0 to 10, preferably an integer of 0 to 5, more preferably an integer of 0 to 3, and still more preferably 0.

In formula (a6a-3), $Va''^{61}$ represents a divalent cyclic hydrocarbon group, and is the same as defined for the "aliphatic hydrocarbon group containing a ring in the structure thereof" and "aromatic hydrocarbon group" explained above in relation to $Va'^{61}$ in the aforementioned formula (a6a-r-1).

$La''^{61}$ represents —C(=O)—O—, —O—C(=O)—O— or —O—CH$_2$—C(=O)—O—.

In formula (a6a-4), $Va''^{62}$ represents a divalent hydrocarbon group, and is the same as defined for the divalent hydrocarbon group explained above in relation to $Va'^{61}$ in the aforementioned formula (a6a-r-1).

$Ra''^{65}$ represents a hydrogen atom or an alkyl group of 1 to 5 carbon atoms.

In formula (a6a-6), $La''^{62}$ represents —C(=O)—O—, —O—C(=O)—O— or —NH—C(=O)—O—.

In formula (a6a-7), $Ya''^{61}$ represents a divalent cyclic hydrocarbon group, and is the same as defined for the "aliphatic hydrocarbon group containing a ring in the structure thereof", the "aromatic hydrocarbon group" and the "divalent linking group containing a hetero atom" (having an "aliphatic hydrocarbon group containing a ring in the structure thereof" or an "aromatic hydrocarbon group") described later in relation to the divalent linking group for $Ya^{21}$ in the aforementioned general formula (a2-1).

In formula (a6a-8), $Va''^{63}$ represents a divalent cyclic hydrocarbon group or a single bond. The divalent cyclic hydrocarbon group for $Va''^{63}$ is the same as defined for the "aliphatic hydrocarbon group containing a ring in the structure thereof" and "aromatic hydrocarbon group" explained above in relation to $Va'^{61}$ in the aforementioned formula (a6a-r-1).

In formula (a6a-1) to (a6a-8), m represents an integer of 1 or more, and each $M^{m+}$ independently represents an organic cation having a valency of m (provided that the cation moiety of the compound (b0) is excluded).

The organic cation for $M^{m+}$ is not particularly limited. As the organic cation, an onium cation having a valency of m is preferable, more preferably a sulfonium cation or an iodonium cation, most preferably an organic cation represented by any one of the aforementioned formulae (ca-1) to (ca-4).
Specific examples of structural unit represented by formula (a6a-1) are shown below. $(M^{m+})_{1/m}$ is the same as defined above.
[Chemical Formula 54]
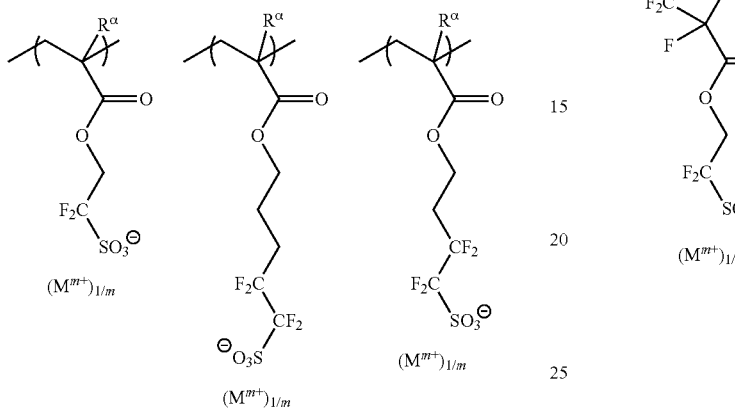
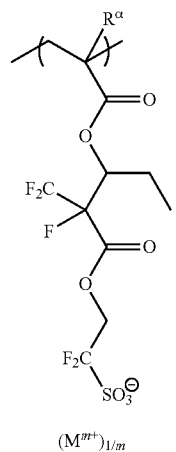
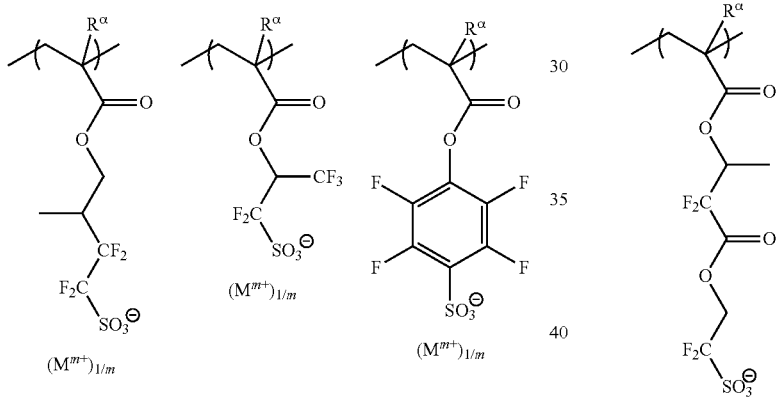
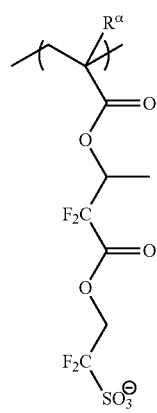
Specific examples of structural unit represented by formula (a6a-2) are shown below.
[Chemical Formula 55]
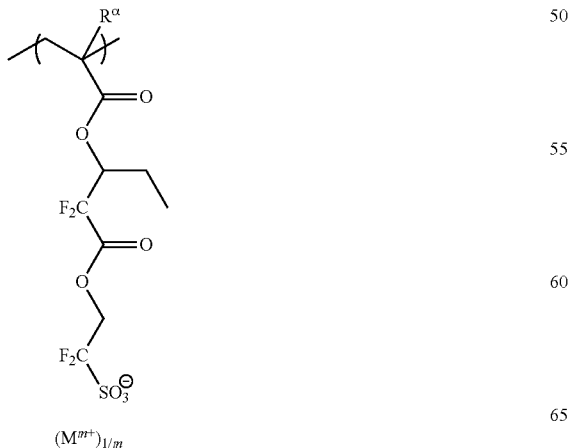
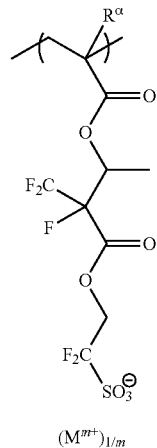

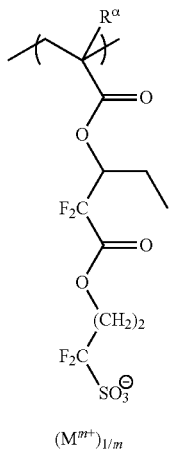
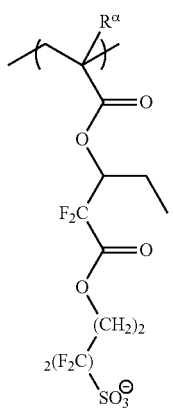
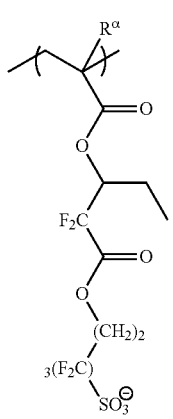
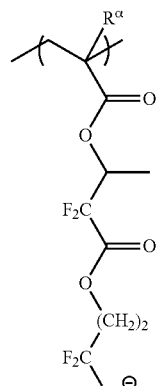
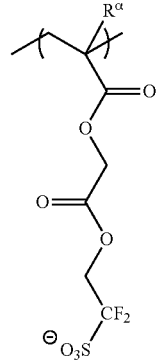
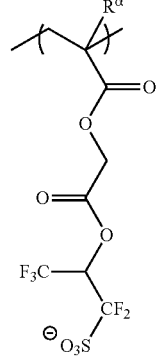
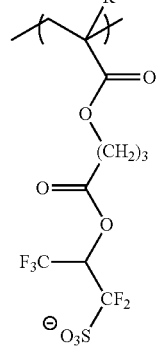

Specific examples of structural unit represented by formula (a6a-3) are shown below.
[Chemical Formula 56]
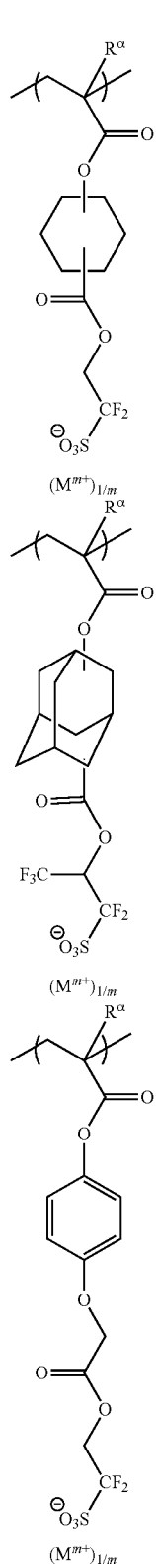
Specific examples of structural unit represented by formula (a6a-4) are shown below.
[Chemical Formula 57]
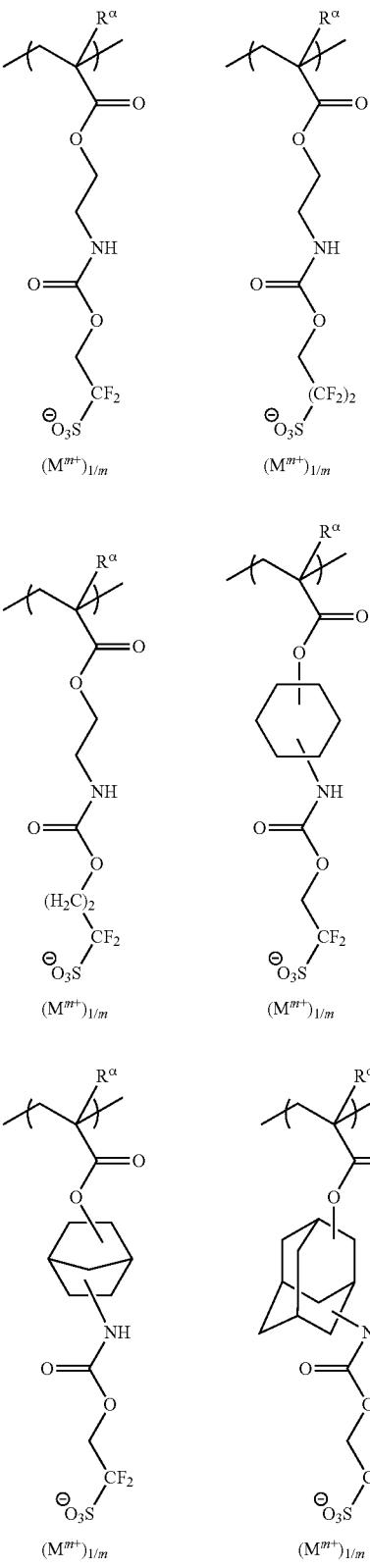

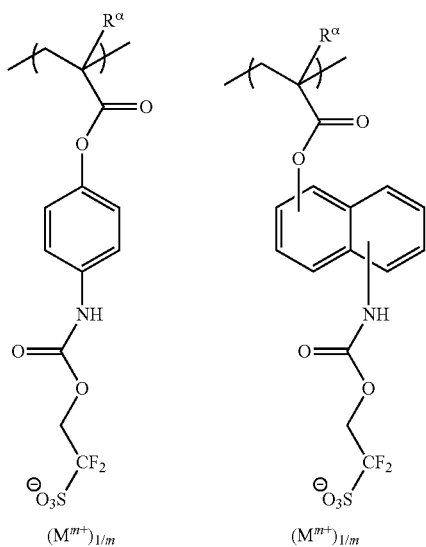
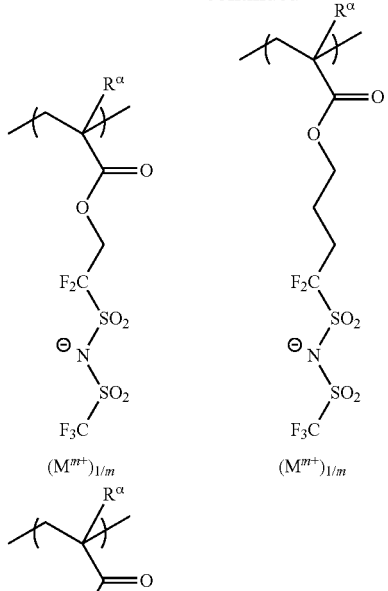
Specific examples of structural unit represented by formula (a6a-5) are shown below.
[Chemical Formula 58]
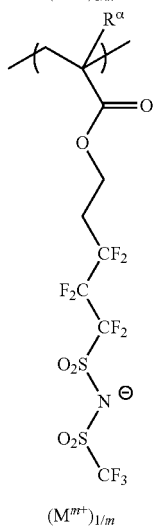
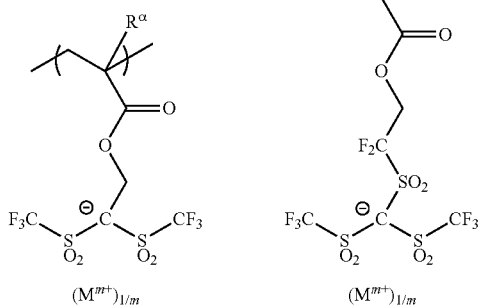
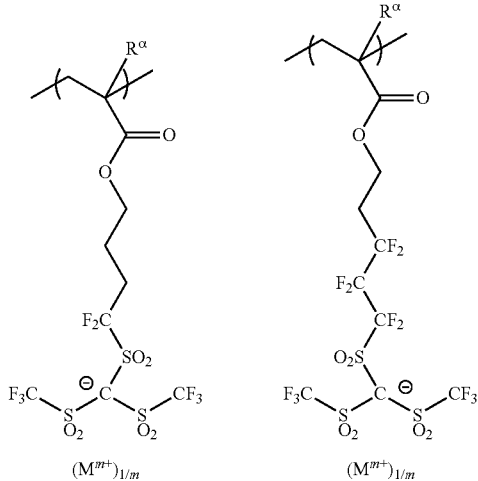
Specific examples of structural unit represented by formula (a6a-6) are shown below.
[Chemical Formula 59]
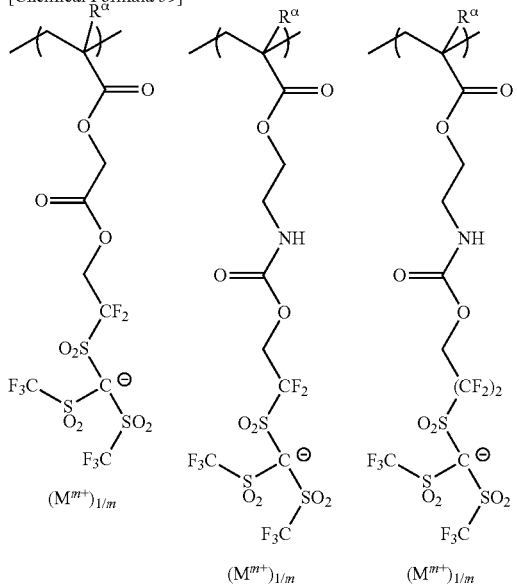

115
-continued
116
Specific examples of structural unit represented by formula (a6a-7) are shown below.
[Chemical Formula 60]
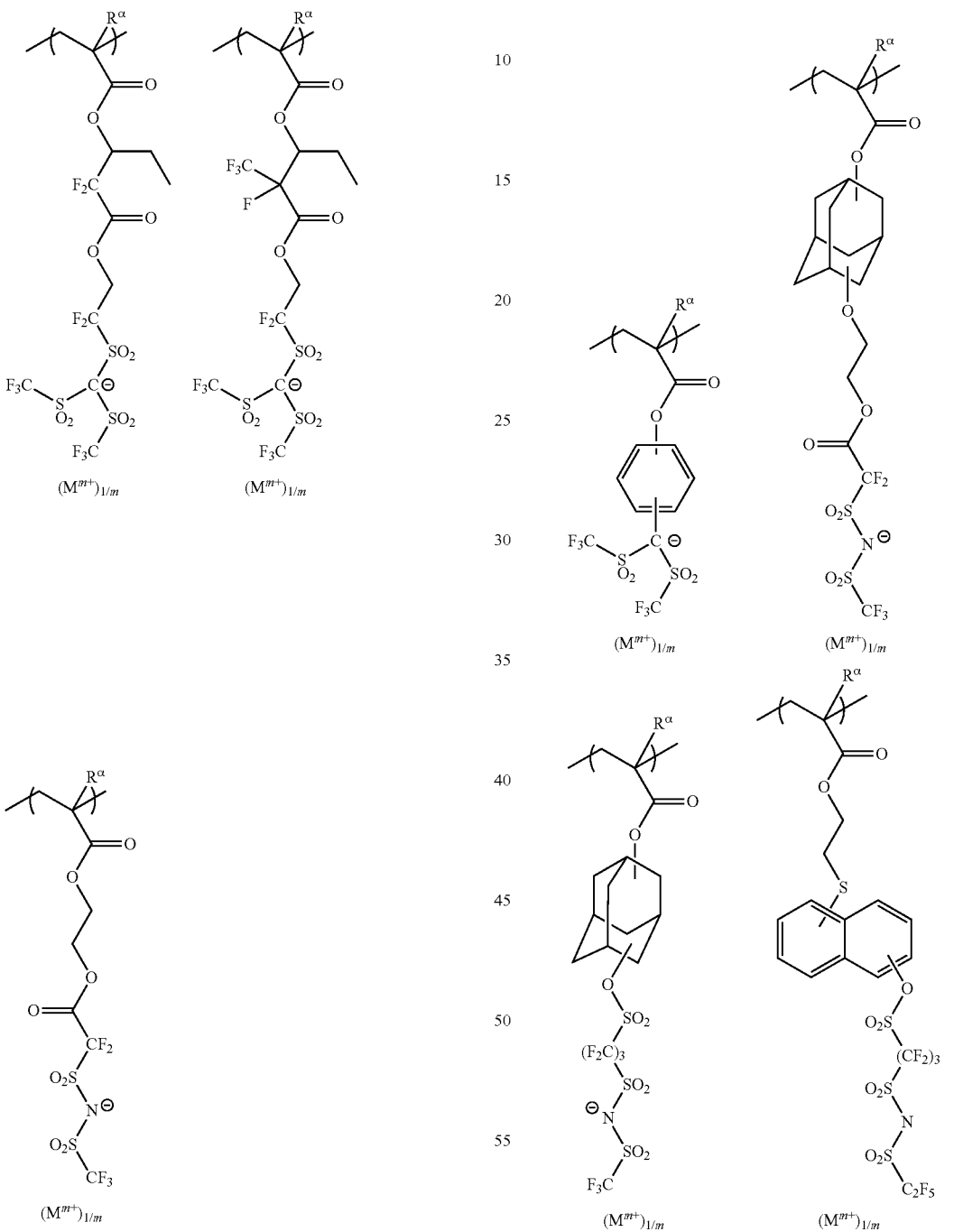

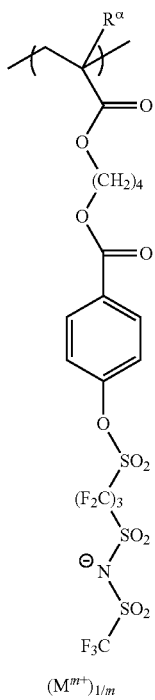

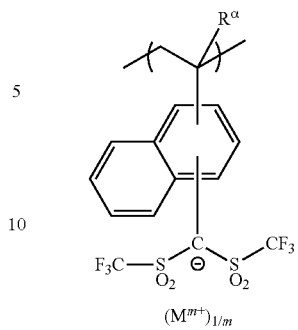

Specific examples of structural unit represented by formula (a6a-8) are shown below.

[Chemical Formula 61]

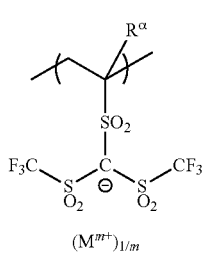 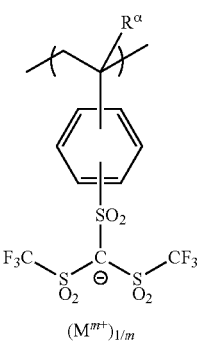

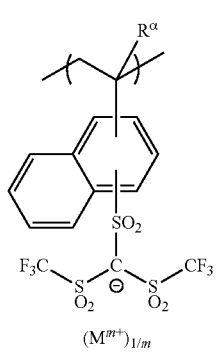 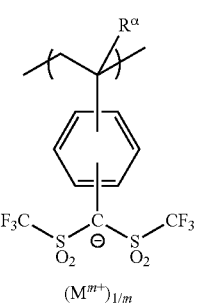

Structural Unit (a6c)

The structural unit (a6a) is a structural unit having a cation group which is decomposed upon exposure on a side chain thereof.

The cation group decomposed upon exposure is not particularly limited, and a group represented by general formula (a6c-r-1) shown below is preferable.

[Chemical Formula 62]

In the formula, $Ra'^{61c}$ and $Ra'^{62c}$ each independently represents an aryl group which may have a substituent, an alkyl group which may have a substituent or an alkenyl group which may have a substituent; $Va'^{61c}$ represents an arylene group, an alkylene group or an alkenylene group; provided that $Ra'^{61c}$ $Ra'^{62c}$ and $Va'^{61c}$ may be mutually bonded to form a ring with the sulfur atom.

In formula (a6c-r-1), $Ra'^{61c}$ and $Ra'^{62c}$ each independently represents an aryl group which may have a substituent, an alkyl group which may have a substituent or an alkenyl group which may have a substituent; $Ra'^{61c}$ and $Ra'^{62c}$ are the same as defined for the "aryl group which may have a substituent", the "alkyl group which may have a substituent" and the "alkenyl group which may have a substituent" for $R^{201}$ to $R^{203}$ in the aforementioned formula (ca-1).

$Va'^{61c}$ represents an arylene group, an alkylene group or an alkenylene group, and examples thereof include a group in which one hydrogen atom has been removed from an aryl group, an alkyl group or an alkenyl group for $Ra'^{61c}$ and $Ra'^{62c}$.

$Ra'^{61c}$, $Ra'^{62c}$ and $Va'^{61c}$ may be mutually bonded to form a ring with the sulfur atom. Examples of the formed ring structure include a group in which one hydrogen atom has been removed from the ring formed by $R^{201}$ to $R^{203}$ mutually bonded with the sulfur atom.

Preferable examples of the structural unit (a6c) include structural units represented by general formulae (a6c-1) to (a6c-3) shown below.

[Chemical Formula 63]

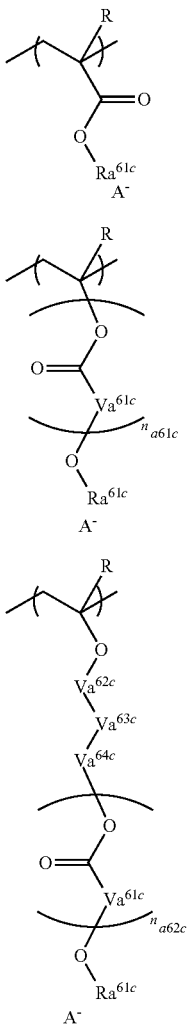

(a6c-1)

(a6c-2)

(a6c-3)

In the formula, R represents a hydrogen atom, an alkyl group of 1 to 5 carbon atoms or a halogenated alkyl group of 1 to 5 carbon atoms; each $Va^{61c}$ independently represents an alkylene group of 1 to 5 carbon atoms; $Va^{62c}$ and $Va^{64c}$ each independently represents an alkylene group of 1 to 10 carbon atoms; $Va^{63c}$ represents an aliphatic cyclic group or a single bond; $na^{61c}$ represents an integer of 0 to 2; $na^{62c}$ represents 0 or 1; $Ra^{61c}$ is a group represented by the aforementioned formula (a6c-r-1); and $A^-$ represents a counteranion.

In formulae (a6c-1) to (a6c-3), R is the same as defined for R in the aforementioned formula (a1-1). Each $Ra^{61c}$ independently represents a group represented by the aforementioned formula (a6c-r-1).

In formulae (a6c-2) and (a6c-3), each $Va^{61c}$ independently represents an alkylene group of 1 to 5 carbon atoms, preferably an alkylene group of 1 to 3 carbon atoms, and more preferably a methylene group.

In formula (a6c-3), $Va^{62c}$ and $Va^{64c}$ independently represents an alkylene group of 1 to 10 carbon atoms, preferably an alkylene group of 1 to 8 carbon atoms, more preferably an alkylene group of 1 to 5 carbon atoms, and still more preferably an alkylene group of 1 to 3 carbon atoms.

In formula (a6c-3), $Va^{63c}$ represents an aliphatic cyclic group or a single bond. The aliphatic cyclic group for $Va^{63c}$ is the same as defined for the aliphatic cyclic group explained above in relation to $Va'^{61}$ in the aforementioned formula (a6a-r-1).

$na^{61c}$ represents an integer of 0 to 2, preferably 1 or 2.

$na^{62c}$ represents 0 or 1.

In formulae (a6c-1) to (a6c-3), $A^-$ represents a counteranion.

The counteranion for $A^-$ is not particularly limited, and examples thereof include the anion moiety of an onium salt acid generator represented by general formula (b-1), (b-2) or (b-3) described above in relation to the component (B). The counteranion is preferably the anion moiety of an onium salt acid generator represented by general formula (b-1), more preferably a fluorinated alkylsulfonate ion of 1 to 8 carbon atoms (preferably 1 to 4 carbon atoms) or at least one member selected from anions represented by the aforementioned general formulae (an-1) to (an-3).

Specific examples of the structural unit represented by formula (a6c-1), (a6c-2) or (a6c-3) are shown below. $A^-$ is the same as defined above.

[Chemical Formula 64]

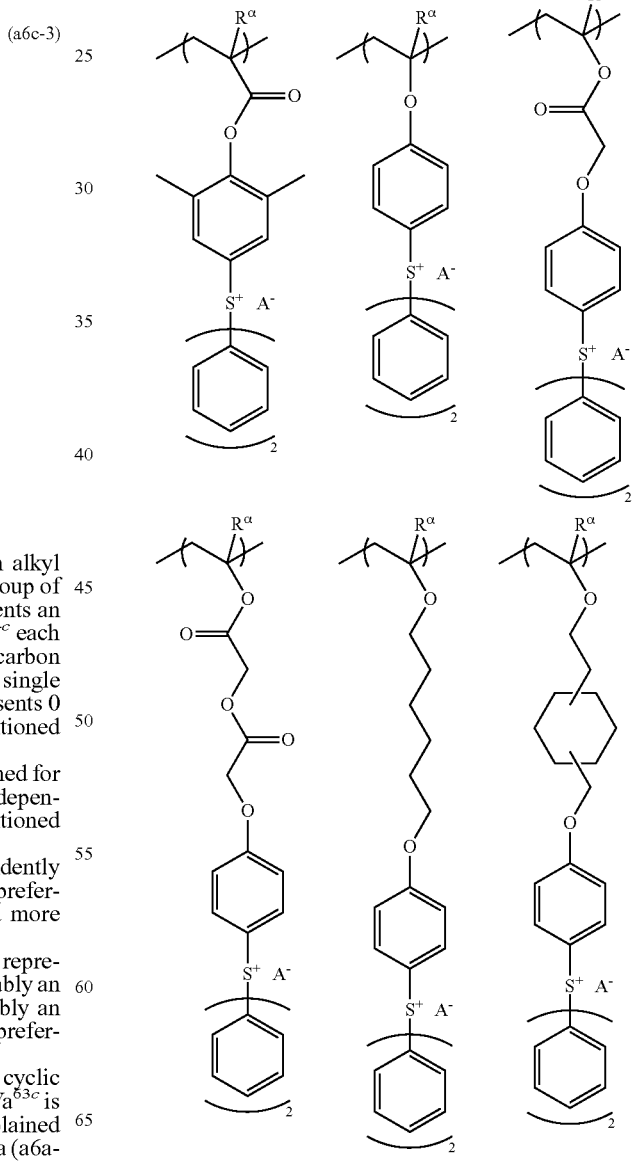

-continued

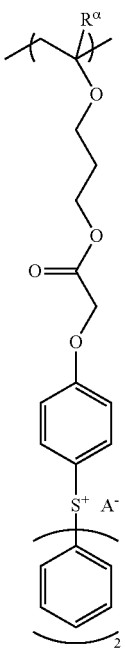

As the structural unit (a6) contained in the component (A11), 1 kind of structural unit may be used, or 2 or more kinds may be used.

As the structural unit (a6a), a structural unit represented by general formula (a6a-1) or (a6a-2) is preferable. As the structural unit (a6c), a structural unit represented by general formula (a6c-1) shown below is preferable.

Among these, as the structural unit (a6), the structural unit (a6a) is preferable.

The amount of the structural unit (a6) within the component (A11) based on the combined total of all structural units constituting the component (A11) is preferably 0.5 to 30 mol %, more preferably 1 to 20 mol %, and still more preferably 1.5 to 15 mol %.

When the amount of the structural unit (a6) is at least as large as the lower limit of the above-mentioned range, roughness can be reduced, and an excellent resist pattern can be reliably obtained. On the other hand, when the amount of the structural unit (a6) is no more than the upper limit of the above-mentioned range, a good balance can be achieved with the other structural units, and the lithography properties can be improved.

The component (A11) may contain, in addition to the structural unit (a1) and the structural unit (a6), the structural unit (a2), the structural unit (a3) or other structural unit (such as the structural unit (a4)).

The structural unit (a2), the structural unit (a3) and the other structural units (such as the structural unit (a4)) is the same as defined for the structural unit (a2), the structural unit (a3) and the other structural units (such as the structural unit (a-4)) explained above in relation to the first resist composition (specific examples, amount, etc.).

The component (A11) is a copolymer containing the structural unit (a1) and the structural unit (a6). The copolymer preferably contains, in addition to the structural unit (a1) and the structural unit (a6), at least one of a structural unit (a2) and a structural unit (a3), and still more preferably a copolymer containing the structural units (a1), (a6), (a2) and (a3).

The weight average molecular weight (Mw) (the polystyrene equivalent value determined by gel permeation chromatography) of the component (A11) is not particularly limited, but is preferably 1,000 to 50,000, more preferably 1,500 to 30,000, and most preferably 2,000 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the polydispersity (Mw/Mn) of the component (A11) is not particularly limited, but is preferably 1.0 to 5.0, more preferably 1.0 to 3.0, and most preferably 1.2 to 2.5.

In the second resist composition, as the component (A11), one type may be used, or two or more types of compounds may be used in combination.

In the component (A), the amount of the component (A11) based on the total weight of the component (A) is preferably 25% by weight or more, more preferably 50% by weight or more, still more preferably 75% by weight or more, and may be even 100% by weight. When the amount of the component (A11) is 25% by weight or more, various lithography properties are improved, such as improvement in mask reproducibility and exposure dose, and reduction of roughness.

In the second resist composition, as the component (A), one type may be used, or two or more types of compounds may be used in combination.

In the second resist composition, the amount of the component (A) can be appropriately adjusted depending on the thickness of the resist film to be formed, and the like.

[Component (D)]

The second resist composition contains the compound represented by general formula (d0) shown below (compound (d0)) as an acid diffusion control agent (D) (component (D)).

[Chemical Formula 65]

(d0)

In formula (d0), $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group; and $X2^-$ represents a monovalent organic anion capable of generating a weak acid.

The compound (d0) is the same as defined for the compound (d0) described above in relation to the first resist composition.

Furthermore, in the second resist composition, as the component (D), an acid diffusion control agent other than the compound (d0) may be used in combination with the compound (d0). The acid diffusion control agent other than the compound (d0) is not particularly limited as long it does not fall under the definition of the compound (d0), and any of the known acid diffusion control agents used in conventional chemically amplified resist compositions can be used. Examples of the acid diffusion control agent include the aforementioned components (D1) and (D2).

The compound (d0), the component (D1) and the component (D2) are the same as defined for the compound (d0), the component (D1) and the component (D2) explained above in relation to the first resist composition (specific examples, amount, etc.).

[Optional Components]

The second resist composition may contain, in addition to the aforementioned component (A) and (D), any other components.

The second resist composition may preferably include a component (B) (i.e., an acid generator component which generates acid upon exposure), in addition to the component (A) and the component (D). As the component (B), a compound represented by general formula (b0) shown below (compound (b0)) is preferable.

[Chemical Formula 66]

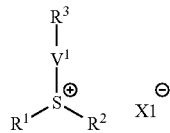

(b0)

In formula (b0), $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group; and $X1^-$ represents a monovalent organic anion capable of generating a strong acid.

The compound (b0) is the same as defined for the compound (b0) described above in relation to the first resist composition.

Furthermore, in the second resist composition, as the component (B), an acid generator other than the compound (b0) may be used in combination with the compound (b0). The acid generator other than the compound (b0) is not particularly limited as long it does not fall under the definition of the compound (b0), and any of the known acid generators used in conventional chemically amplified resist compositions can be used. Examples of the acid generator include the aforementioned component (B1).

The compound (b0) and the component (B1) are the same as defined for the compound (b0) and the component (B1) explained above in relation to the first resist composition (specific examples, amount, etc.).

The second resist composition may contain, apart from the aforementioned components (A), (D) and (B), the aforementioned components (E), (F) and (S) described above in relation to the first resist composition. If desired, other miscible additives can also be added to the second resist composition. Examples of such miscible additives include additive resins for improving the performance of the resist film, dissolution inhibitors, plasticizers, stabilizers, colorants, halation prevention agents, and dyes.

<Resist Composition of Third Embodiment>

The resist composition of the third embodiment (hereafter, sometimes referred to as "third resist composition") includes a base component which exhibits changed solubility in a developing solution under action of acid, and generated acid upon exposure. Further, the base component contains a polymeric compound having an anion group which generated acid upon exposure, and a cation moiety containing a cation represented by general formula (m1) shown below (hereafter, this polymeric compound is referred to as "component (A12)").

[Chemical Formula 67]

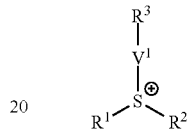

(m1)

In formula (m1), $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group.

Component (A12):

In the third resist composition, the component (A12) is a polymeric compound having an anion group which generated acid upon exposure, and a cation moiety containing a cation represented by general formula (m1).

Cation Moiety Containing Cation Represented by General Formula (m1)

In formula (m1), $R^1$, $R^2$, $R^3$ and $V^1$ are the same as defined for $R^1$, $R^2$, $R^3$ and $V^1$ in the aforementioned formula (m0).

Anion Group which Generates Acid Upon Exposure

The anion group which generates acid upon exposure is not particularly limited, and examples thereof include a sulfonic acid anion, a carboxylic acid anion, an amide anion and a methide anion.

Specific examples of the anion group include groups represented by general formula (a6a-r-1), (a6a-r-2) and (a6a-r-3) described above in relation to the aforementioned structural unit (a6).

Further, an anion represented by the formula —C(=O)—O$^-$, an anion represented by the formula —SO$_3^-$, and an anion represented by the formula —Yd$^1$—N$^-$—SO$_2$—Rd$^3$ may be given as preferable examples. In the above formula, Yd$^1$ and Rd$^3$ are the same as defined for Yd$^1$ and Rd$^3$ in the aforementioned general formula (d1-3).

Examples of the component (A12) includes polymeric compound containing a structural unit (am0) having an anion group which generates acid upon exposure on a side chain, and a cation moiety containing a cation represented by general formula (m1) (hereafter, sometimes referred to as "component (A12-1)"); and a polymeric compound having an anion group which generates acid upon exposure on a main chain, and a cation moiety containing a cation represented by general formula (m1) (hereafter, sometimes referred to as "component (A12-2)").

Among these examples, a component (A12-1) having an anion group on a side chain is preferable.

{Component (A12-1)}

The component (A12-1) is a polymeric compound including an anion group which generates acid upon exposure on a side chain of the polymeric compound, and a structural unit (am0) having a cation moiety containing a cation represented by general formula (m1).

(Structural Unit (am0))

The structural unit (am0) is a structural unit having an anion group which generates acid upon exposure on a side chain, and a cation moiety containing a cation represented by general formula (m1).

Examples of the structural unit (am0) include a structural unit derived from a compound represented by general formula (am0-1) shown below (hereafter, sometimes referred to as "compound (am0-1)"), and a structural unit derived from a compound represented by general formula (am0-2) (hereafter, sometimes referred to as "compound (am0-2)").

[Chemical Formula 68]

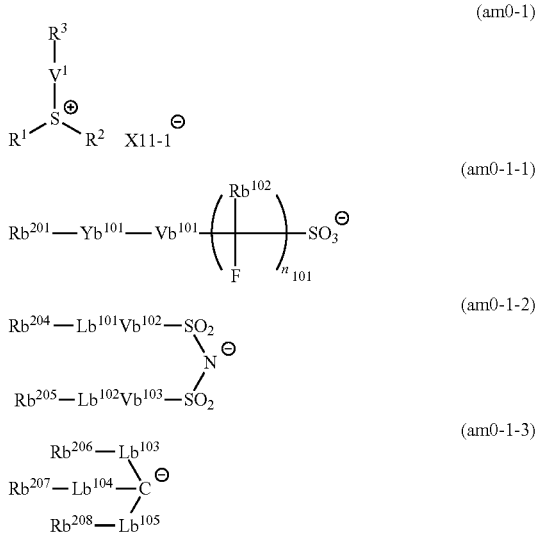

In formula (am0-1), $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group; and $X11-1^-$ is an organic anion represented by any one of the aforementioned general formulae (am0-1-1) to (am0-1-3). In formulae (am0-1-1) to (am0-1-3), $Rb^{201}$ represents a chain-like alkenyl group which may have a substituent; $Rb^{204}$ and $Rb^{205}$ each independently represents a cyclic group which may have a substituent, a chain-like alkyl group which may have a substituent or a chain-like alkenyl group which may have a substituent (provided that at least one of $Rb^{204}$ and $Rb^{205}$ represents a chain-like alkenyl group which may have a substituent; $Rb^{206}$ to $Rb^{208}$ each independently represents a cyclic group which may have a substituent, a chain-like alkyl group which may have a substituent or a chain-like alkenyl group which may have a substituent (provided that at least one of $Rb^{206}$ to $Rb^{208}$ represents a chain-like alkenyl group which may have a substituent; $Rb^{102}$ represents a fluorine atom or a fluorinated alkyl group of 1 to 5 carbon atoms; $Yb^{101}$ represents a single bond or a divalent linking group containing an oxygen atom; $Vb^{101}$ to $Vb^{103}$ each independently represents a single bond, an alkylene group, a fluorinated alkylene group, an arylene group or a fluorinated arylene group; $L^{101}$ and $L^{102}$ each independently represents a single bond or an oxygen atom; $Lb^{103}$ to $Lb^{105}$ each independently represents a single bond, —CO— or —$SO_2$—; and $n_{101}$ represents 0 or 1.

Structural Unit Derived from Compound (am0-1)

In formula (am0-1), $R^1$, $R^2$, $R^3$ and $V^1$ are the same as defined for $R^1$, $R^2$, $R^3$ and $V^1$ in the aforementioned formula (m1).

In formula (am0-1-1), $Rb^{201}$ is the same as defined for the chain-like alkenyl group represented by $R^{101}$ in the aforementioned formula (b-1).

In formula (am0-1-2), $Rb^{204}$ and $Rb^{205}$ are the same as defined for the cyclic group which may have a substituent, the chain-like alkyl group which may have a substituent or the chain-like alkenyl group which may have a substituent represented by $R^{104}$ and $R^{105}$ in the aforementioned formula (b-2). However, at least one of $Rb^{204}$ and $Rb^{205}$ represents a chain-like alkenyl group which may have a substituent.

In formula (am0-1-3), $Rb^{206}$ to $Rb^{208}$ are the same as defined for the cyclic group which may have a substituent, the chain-like alkyl group which may have a substituent or the chain-like alkenyl group which may have a substituent represented by $R^{106}$ to $R^{108}$ in the aforementioned formula (b-3). However, at least one of $Rb^{206}$ to $Rb^{208}$ represents a chain-like alkenyl group which may have a substituent.

$Rb^{102}$, $Yb^{101}$, $Vb^{101}$ to $Vb^{103}$, $Lb^{101}$ to $Lb^{102}$ and $Lb^{103}$ to $Lb^{105}$ are the same as defined for $R^{102}$, $Y^{101}$, $V^{101}$ to $V^{103}$, $L^{101}$ to $L^{102}$ and $L^{103}$ to $L^{105}$ in the aforementioned formulae (b-1), (b-2) and (b-3), respectively.

In formulae (am0-1-1) to (am0-1-3), in the case where at least one of $Rb^{201}$, $Rb^{204}$ and $Rb^{205}$, and at least one of $Rb^{206}$ to $Rb^{208}$ is a chain-like alkenyl group which may have a substituent, $(CH_3)C=CH$— (a propenyl group) or $H_2C=CH$— (a vinyl group) is preferable. In the case of a chain-like alkenyl group which may have a substituent, the vinyl group or the propenyl group preferably has a divalent group bonded thereto. Examples of the divalent group include an ester bond, an ether bond, an amide bond, a urethane bond, an alkylene group, a (poly)cycloalkylene group, a fluorinated alkylene group, an arylene group, —$SO_2$—O—, —$SO_2$—, or a combination thereof Specific examples of preferable anions represented by formula (am0-1-1) are shown below. In the formulae shown below, $R^\alpha$ represents a hydrogen atom, a methyl group or a trifluoromethyl group.

[Chemical Formula 69]
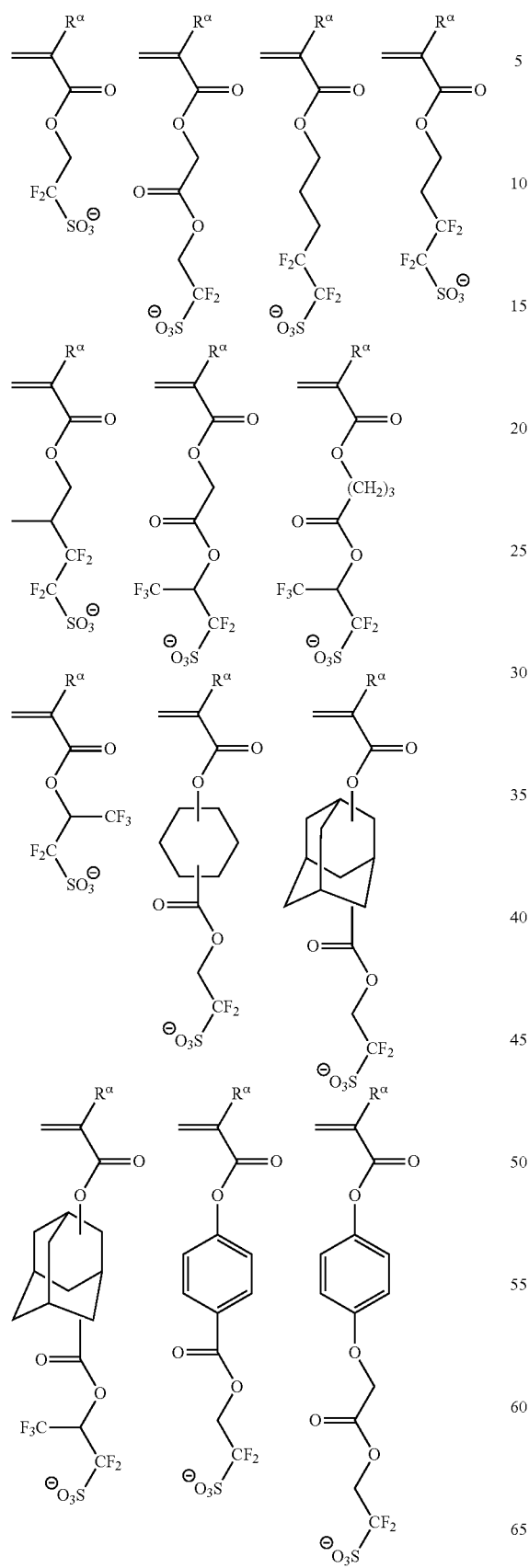
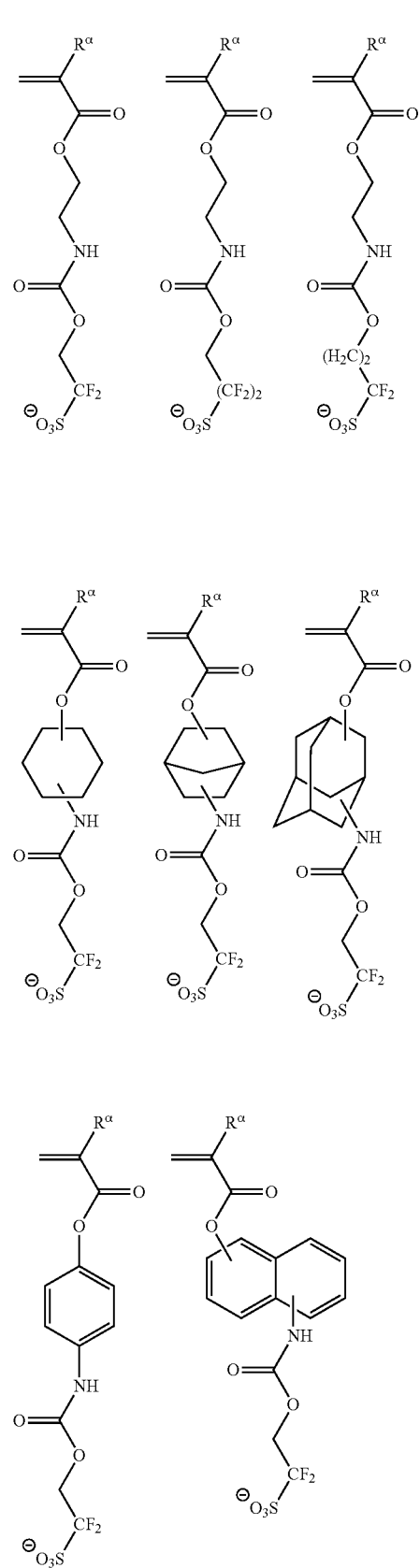

-continued
[Chemical Formula 70]
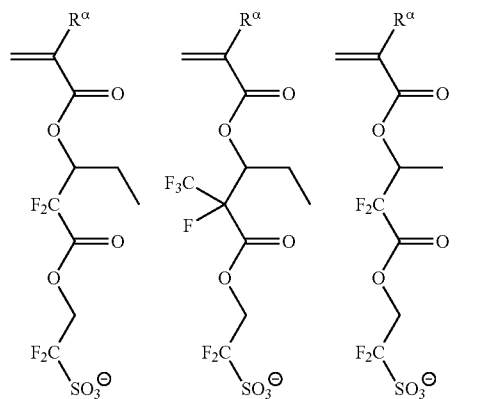
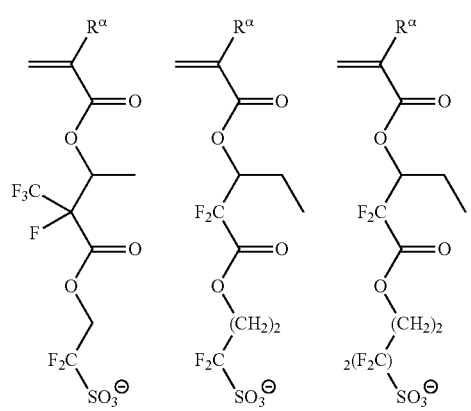
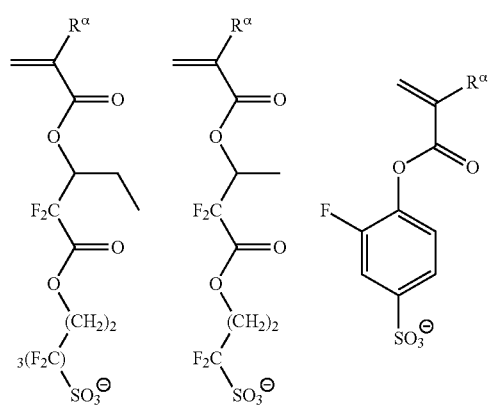
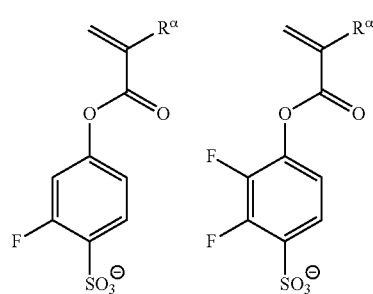
-continued
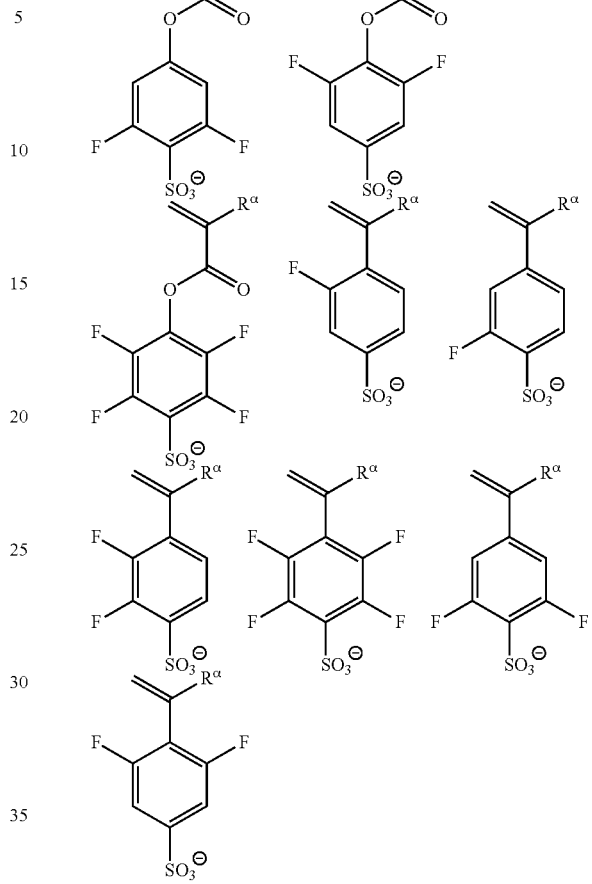
Specific examples of preferable anions represented by formula (am0-1-2) are shown below. In the formulae shown below, $R^\alpha$ represents a hydrogen atom, a methyl group or a trifluoromethyl group.
[Chemical Formula 71]
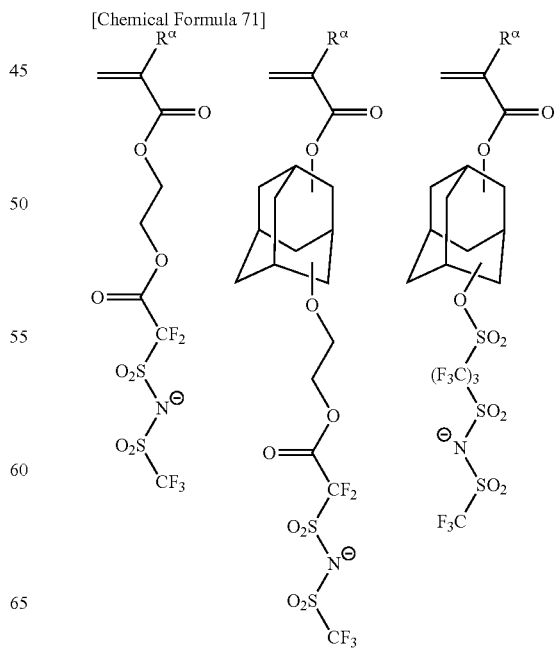

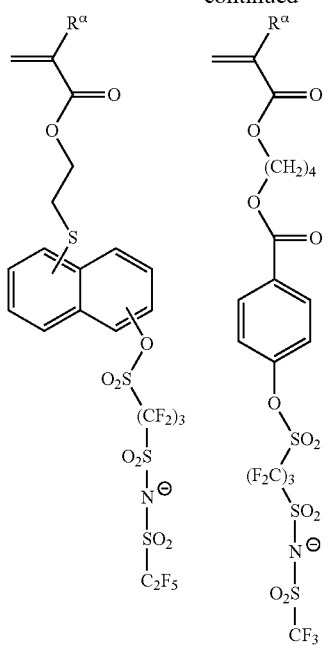
Specific examples of preferable anions represented by formula (am0-1-3) are shown below. In the formulae shown below, $R^\alpha$ represents a hydrogen atom, a methyl group or a trifluoromethyl group.
[Chemical Formula 72]
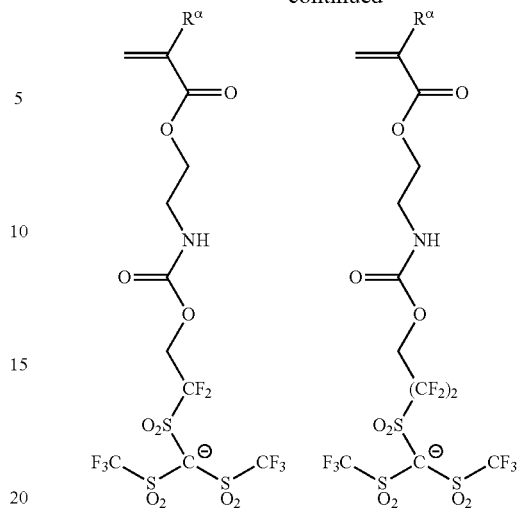
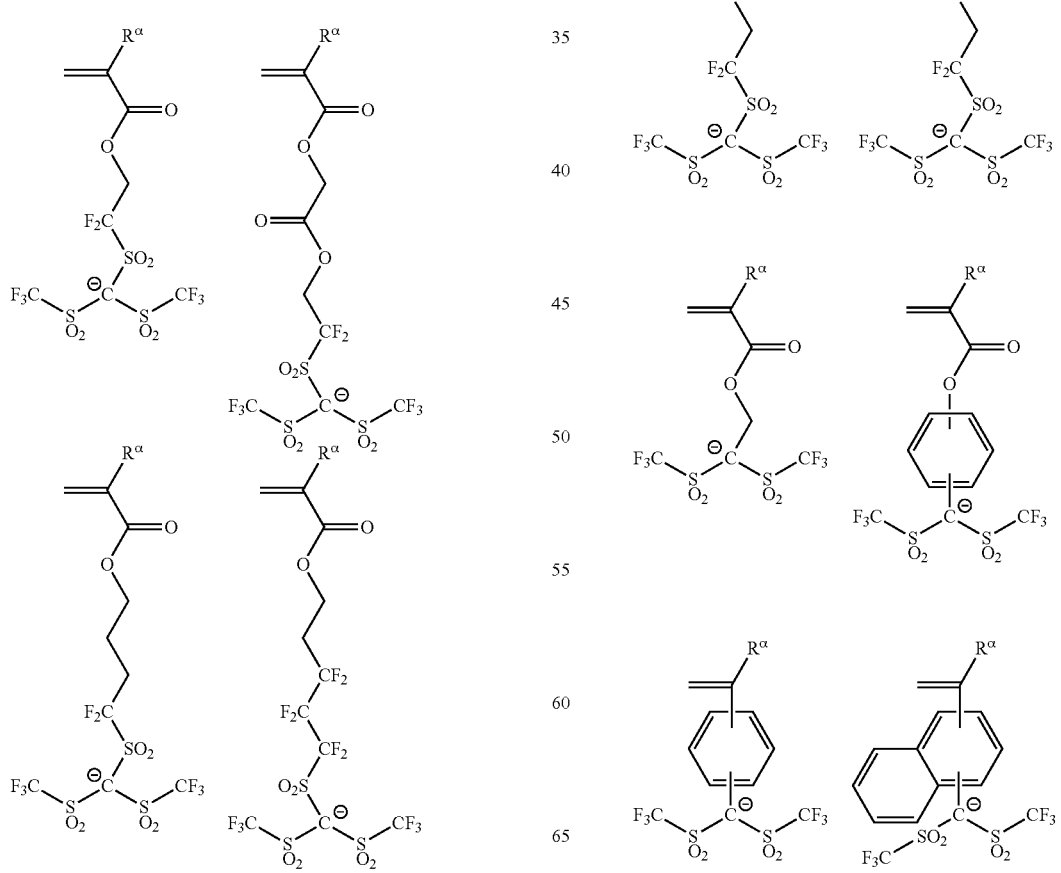

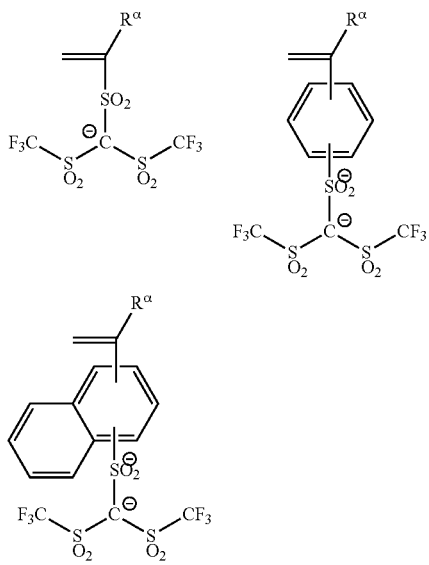

Preferable examples of the structural unit derived from compound (am0-1) include structural units represented by general formulae (am0-11) to (am0-13) shown below.

[Chemical Formula 73]

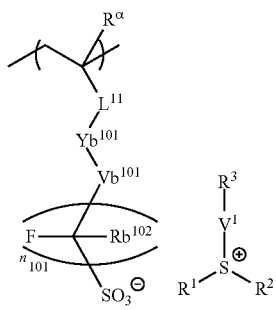
(am0-11)

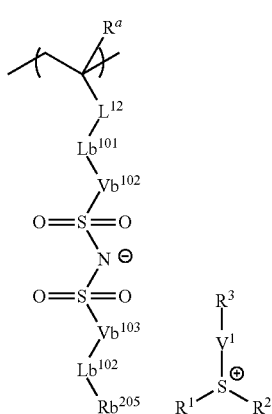
(am0-12)

(am0-13)

In the formulae, $R^\alpha$, $R^1$, $R^2$, $R^3$, $V^1$, $Rb^{102}$, $Rb^{205}$, $Rb^{206}$, $Rb^{208}$, $Yb^{101}$, $Vb^{101}$ to $Vb^{103}$, $Lb^{101}$ and $Lb^{102}$, $Lb^{103}$ to $Lb^{105}$ and $n_{101}$ are the same as defined above; $L^{11}$ to $L^{13}$ each independently represents a single bond or a divalent linking group.

In formulae (am0-11) to (am0-13), examples of the divalent linking group for $L^{11}$ to $L^{13}$ include an ester bond, an alkylene group of 1 to 10 carbon atoms, a cycloalkylene group of 5 to 30 carbon atoms, a polycycloalkylene group of 5 to 30 carbon atoms, an arylene group of 6 to 10 carbon atoms, and a combination of any of these groups.

Specific examples of the structural unit derived from compound (am0-1) include the specific examples of the aforementioned structural unit (a6a) (i.e., specific examples of structural units represented by general formulae (a6a-1) to (a6a-8)) in which the cation moiety has been replaced by a cation represented by the aforementioned general formula (m1).

In the component (A12-1), as the structural unit derived from compound (am0-1), one type of structural unit may be used, or two or more structural units may be used.

The amount of the structural unit derived from compound (am0-1) within the component (A12-1) based on the combined total of all structural units constituting the component (A12-1) is preferably 0.5 to 30 mol %, more preferably 1 to 20 mol %, and still more preferably 1.5 to 15 mol %.

When the amount of the structural unit derived from compound (am0-1) is at least as large as the lower limit of the above-mentioned range, roughness can be reduced, and an excellent resist pattern can be reliably obtained. In addition, the solubility in a solvent and the sensitivity are also improved. On the other hand, when the amount of the structural unit derived from compound (am0-1) is no more than the upper limit of the above-mentioned range, a good balance can be achieved with the other structural units, and the lithography properties can be improved.

[Chemical Formula 74]

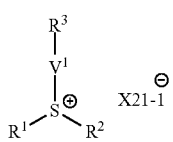
(am0-2)

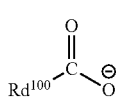
(am0-2-1)

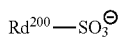
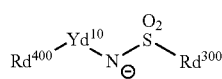

In formula (am0-2), $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group; and X21-1⁻ is an organic anion represented by any one of the aforementioned general formulae (am0-2-1) to (am0-2-3). In formula (am0-2-1), $Rd^{100}$ represents a chain-like alkenyl group which may have a substituent. In formula (am0-2-2), $Rd^{200}$ represents a chain-like alkenyl group which may have a substituent. However, in $Rd^{200}$, the carbon atom adjacent to the sulfur atom has no fluorine atom bonded thereto. In formula (am0-2-3), $Rd^{300}$ and $R^{400}$ each independently represents a cyclic group which may have a substituent, a chain-like alkyl group which may have a substituent or a chain-like alkenyl group which may have a substituent (provided that at least one of $Rd^{300}$ and $Rd^{400}$ represents a chain-like alkenyl group which may have a substituent. $Yd^{10}$ represents a single bond or a divalent linking group.

Structural Unit Derived from Compound (am0-2)

In formula (am0-2), $R^1$, $R^2$, $R^3$ and $V^1$ are the same as defined for $R^1$, $R^2$, $R^3$ and $V^1$ in the aforementioned formula (m1).

In formula (am0-2-1), $Rd^{100}$ is the same as defined for the chain-like alkenyl group represented by $Rd^1$ in the aforementioned formula (d1-1).

In formula (am0-2-2), $Rd^{200}$ is the same as defined for the chain-like alkenyl group represented by $Rd^2$ in the aforementioned formula (d1-2).

In formula (am0-2-3), $Rd^{300}$ and $R^{400}$ are the same as defined for the cyclic group which may have a substituent, the chain-like alkyl group which may have a substituent or the chain-like alkenyl group which may have a substituent represented by $Rd^3$ and $Rd^4$ in the aforementioned formula (d1-3). However, at least one of $Rd^{300}$ and $R^{400}$ represents a chain-like alkenyl group which may have a substituent. In formula (am0-2-3), $Yd^{10}$ is the same as defined for single bond or divalent linking group represented by $Yd^1$ in the aforementioned formula (d1-3).

In formulae (am0-2-1) to (am0-2-3), in the case where at least one of $Rd^{100}$, $Rd^{200}$, $Rd^{300}$ and $Rd^{400}$ is a chain-like alkenyl group which may have a substituent, $(CH_3)C=CH$— (a propenyl group) or $H_2C=CH$—(a vinyl group) is preferable. In the case of a chain-like alkenyl group which may have a substituent, the vinyl group or the propenyl group preferably has a divalent group bonded thereto. Examples of the divalent group include an ester bond, an ether bond, an amide bond, a urethane bond, an alkylene group, a (poly)cycloalkylene group, an arylene group, or a combination thereof.

Specific examples of preferable anions represented by formula (am0-2-1) are shown below. In the formulae shown below, $R^\alpha$ represents a hydrogen atom, a methyl group or a trifluoromethyl group. m represents an integer of 0 to 3.

[Chemical Formula 75]

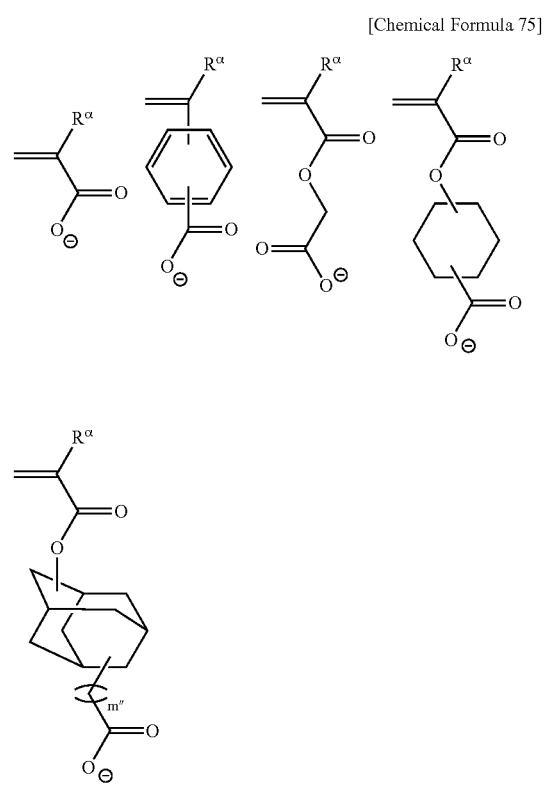

Specific examples of preferable anions represented by formula (am0-2-2) are shown below. In the formulae shown below, $R^\alpha$ represents a hydrogen atom, a methyl group or a trifluoromethyl group.

[Chemical Formula 76]

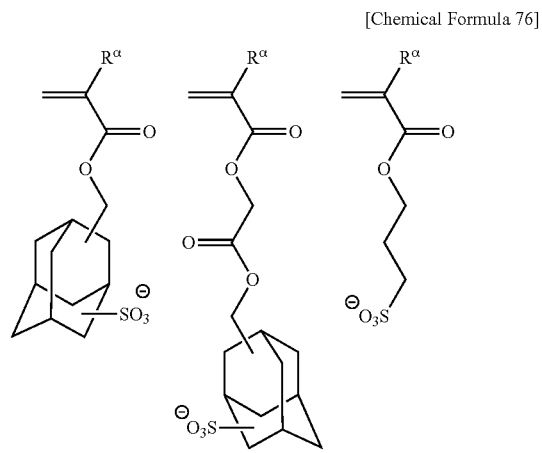

-continued

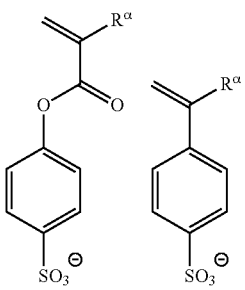

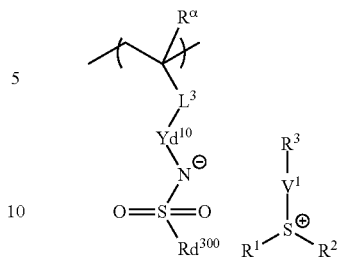

Specific examples of preferable anions represented by formula (am0-2-3) are shown below. In the formulae shown below, $R^\alpha$ represents a hydrogen atom, a methyl group or a trifluoromethyl group.

[Chemical Formula 77]

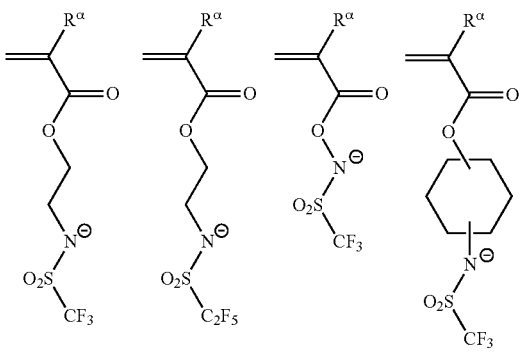

Preferable examples of the structural unit derived from compound (am0-2) include structural units represented by general formulae (am0-21) to (am0-23) shown below.

[Chemical Formula 78]

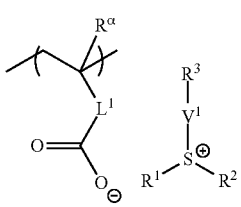
(am0-21)

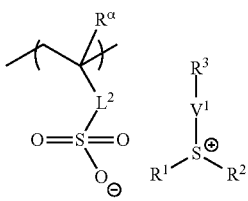
(am0-22)

(am0-23)

In the formulae, $R^\alpha$, $R^1$, $R^2$, $R^3$, $V^1$, $Yd^{10}$ and $Rd^{300}$ are the same as defined above. $L^1$ to $L^3$ each independently represents a single bond or a divalent linking group.

In formulae (am0-21) to (am0-23), examples of the divalent linking group for $L^1$ to $L^3$ include an ester bond, an alkylene group of 1 to 10 carbon atoms, a cycloalkylene group of 5 to 30 carbon atoms, a polycycloalkylene group of 5 to 30 carbon atoms, an arylene group of 6 to 10 carbon atoms, and a combination of any of these groups.

In the component (A12-1), as the structural unit derived from compound (am0-2), one type of structural unit may be used, or two or more structural units may be used.

The amount of the structural unit derived from compound (am0-2) within the component (A12-1) based on the combined total of all structural units constituting the component (A12-1) is preferably 0.5 to 30 mol %, more preferably 1 to 20 mol %, and still more preferably 1.5 to 15 mol %.

When the amount of the structural unit derived from compound (am0-2) is at least as large as the lower limit of the above-mentioned range, roughness can be reduced, and an excellent resist pattern can be reliably obtained. In addition, the solubility in a solvent and the sensitivity are also improved. On the other hand, when the amount of the structural unit derived from compound (am0-2) is no more than the upper limit of the above-mentioned range, a good balance can be achieved with the other structural units, and the lithography properties can be improved.

As the component (A12-1), it is preferable to use a polymeric compound which has, in addition to the structural unit (am0), a structural unit (a1) containing an acid decomposable group that exhibits increased polarity by the action of acid.

The component (A12-1) may contain, in addition to the structural unit (am0) and the structural unit (a1), the structural unit (a2), the structural unit (a3) or other structural unit (such as the structural unit (a4)).

The structural unit (a1), the structural unit (a2), the structural unit (a3) and the other structural units (such as the structural unit (a4)) is the same as defined for the structural unit (a1), the structural unit (a2), the structural unit (a3) and the other structural units (such as the structural unit (a4)) explained above in relation to the first resist composition (specific examples, amount, etc.).

The component (A12-1) is a polymeric compound including the structural unit (am0).

The component (A12-1) is preferably a copolymer containing the structural units (am0) and (a1).

The copolymer containing the structural units (am0) and (a1) is preferably a copolymer further containing at least one of a structural unit (a2) and a structural unit (a3), and still more preferably a copolymer containing the structural units (am0), (a1), (a2) and (a3).

The weight average molecular weight (Mw) (the polystyrene equivalent value determined by gel permeation chromatography) of the component (A12-1) is not particularly limited, but is preferably 1,000 to 50,000, more preferably 1,500 to 30,000, and most preferably 2,000 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the polydispersity (Mw/Mn) of the component (A12-1) is not particularly limited, but is preferably 1.0 to 5.0, more preferably 1.0 to 3.0, and most preferably 1.2 to 2.5.

{Component (A12-2)}

The component (A12-2) is a polymeric compound a polymeric compound including an anion group which generates acid upon exposure on a main chain of the polymeric compound, and a cation moiety containing a cation represented by general formula (m1).

Preferable example of the component (A12-2) include the aforementioned component (A1) having an anion group which generates acid upon exposure on a main chain of the polymeric compound, and a cation represented by general formula (m1) as a counterion of the anion group.

Other examples of the component (A12-2) include the aforementioned component (A11) or (A12-1) having an anion group which generates acid upon exposure on a main chain of the polymeric compound, and a cation represented by general formula (m1) as a counterion of the anion group.

The weight average molecular weight (Mw) (the polystyrene equivalent value determined by gel permeation chromatography) of the component (A12-2) is not particularly limited, but is preferably 1,000 to 50,000, more preferably 1,500 to 30,000, and most preferably 2,000 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the polydispersity (Mw/Mn) of the component (A12-2) is not particularly limited, but is preferably 1.0 to 5.0, more preferably 1.0 to 3.0, and most preferably 1.2 to 2.5.

In the third resist composition, as the component (A12), one type may be used, or two or more types of compounds may be used in combination.

In the third resist composition, the amount of the component (A12) based on the total weight of the base component is preferably 25% by weight or more, more preferably 50% by weight or more, still more preferably 75% by weight or more, and may be even 100% by weight. When the amount of the component (A12) is 25% by weight or more, various lithography properties are improved, such as improvement in mask reproducibility and exposure dose, and reduction of roughness.

In the third resist composition, as the base component, one type may be used, or two or more types of compounds may be used in combination.

In the third resist composition, the amount of the base component can be appropriately adjusted depending on the thickness of the resist film to be formed, and the like.

[Optional Components]

The third resist composition may contain a component other than the aforementioned base component (base component which exhibits changed solubility in a developing solution under action of acid, and generated acid upon exposure).

The third resist composition may preferably include an acid generator component (B) which generates acid upon exposure, in addition to the base component. As the component (B), a compound represented by general formula (b0) shown below (compound (b0)) is preferable.

[Chemical Formula 79]

(b0)

In formula (b0), $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group; and $X1^-$ represents a monovalent organic anion capable of generating a strong acid.

The compound (b0) is the same as defined for the compound (b0) described above in relation to the first resist composition.

Furthermore, in the third resist composition, as the component (B), an acid generator other than the compound (b0) may be used in combination with the compound (b0). The acid generator other than the compound (b0) is not particularly limited as long it does not fall under the definition of the compound (b0), and any of the known acid generators used in conventional chemically amplified resist compositions can be used. Examples of the acid generator include the aforementioned component (B1).

The compound (b0) and the component (B1) are the same as defined for the compound (b0) and the component (B1) explained above in relation to the first resist composition (specific examples, amount, etc.).

The third resist composition may contain, in addition to the aforementioned base component (base component which exhibits changed solubility in a developing solution under action of acid, and generated acid upon exposure), or in addition to the base component and the component (B), an acid diffusion control agent (D). As the component (D), a compound represented by general formula (d0) shown below (compound (d0)) is preferable.

[Chemical Formula 80]

(d0)

In formula (d0), $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; R³ represents an aromatic hydrocarbon group which may have a substituent, an alkenyl group which may have a substituent, or an alkynyl group which may have a substituent; V¹ represents a single bond or an alkylene group, provided that, when R³ is an aromatic hydrocarbon group which may have a substituent, V¹ is an alkylene group; and X2⁻ represents a monovalent organic anion capable of generating a weak acid.

The compound (d0) is the same as defined for the compound (d0) described above in relation to the first resist composition.

Furthermore, in the third resist composition, as the component (D), an acid diffusion control agent other than the compound (d0) may be used in combination with the compound (d0). The acid diffusion control agent other than the compound (d0) is not particularly limited as long it does not fall under the definition of the compound (d0), and any of the known acid diffusion control agents used in conventional chemically amplified resist compositions can be used. Examples of the acid diffusion control agent include the aforementioned components (D1) and (D2).

The compound (d0), the component (D1) and the component (D2) are the same as defined for the compound (d0), the component (D1) and the component (D2) explained above in relation to the first resist composition (specific examples, amount, etc.).

The third resist composition may contain, apart from the aforementioned base component, component (B) and component (D), the aforementioned components (E), (F) and (S) described above in relation to the first resist composition. If desired, other miscible additives can also be added to the second resist composition. Examples of such miscible additives include additive resins for improving the performance of the resist film, dissolution inhibitors, plasticizers, stabilizers, colorants, halation prevention agents, and dyes.

<<Acid Generator>>

The acid generator according to a second aspect of the present invention is a compound represented by general formula (M1) shown below (hereafter, this compound is sometimes referred to as "compound (M1)").

[Chemical Formula 81]

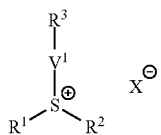

(M1)

In formula (M1), R¹ and R² each independently represents an aryl group which may have a substituent, an alkyl group which may have a substituent, or an alkenyl group which may have a substituent, provided that R¹ and R² may be mutually bonded to form a ring with the sulfur atom; R³ represents an aromatic hydrocarbon group which may have a substituent, an alkenyl group which may have a substituent, or an alkynyl group which may have a substituent; V¹ represents a single bond or an alkylene group, provided that, when R³ is an aromatic hydrocarbon group which may have a substituent, V¹ is an alkylene group; and X represents a sulfonic acid anion, a carboxylic acid anion, an imide anion or a methide anion.

In formula (M1), R¹, R², R³ and V¹ are the same as defined for R¹, R², R³ and V¹ in the aforementioned formula (m0).

In formula (M1), X⁻ represents a sulfonic acid anion, a carboxylic acid anion, an imide anion or a methide anion. As X⁻, for example, the same anions as those defined for the anion of compounds represented by any of the aforementioned general formulae (b-1) to (b-3) and (d1-1) to (d1-3), an organic anion represented by any of the aforementioned general formulae (am0-1-1) to (am0-1-3), and an organic anion represented by any of the aforementioned general formulae (am0-2-1) to (am0-2-3) can be mentioned.

Specific examples of the compound (M1) are shown below.

[Chemical Formula 82]

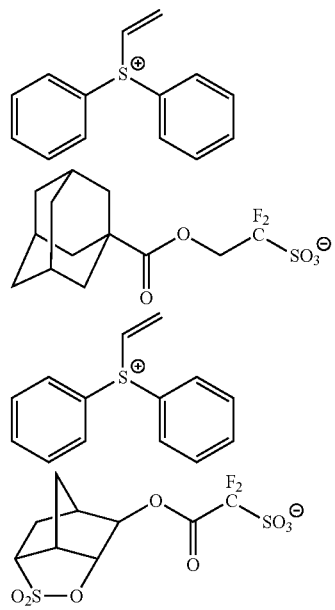

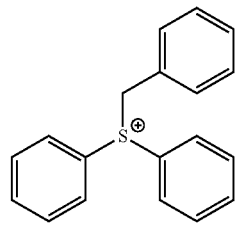

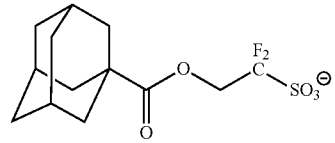

[Chemical Formula 83]

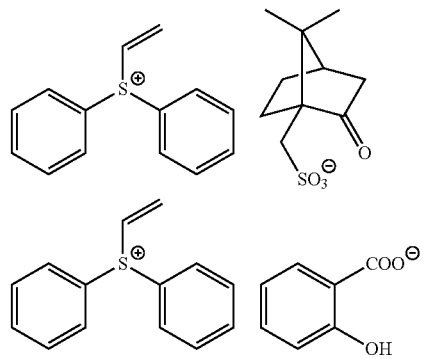

-continued

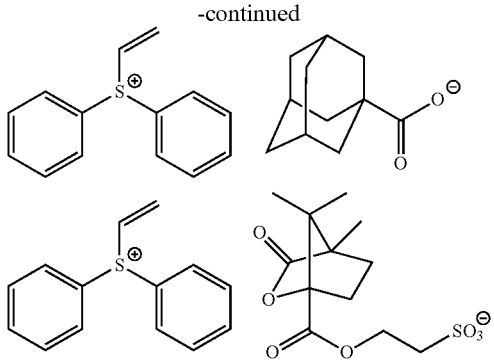

[Chemical Formula 84]

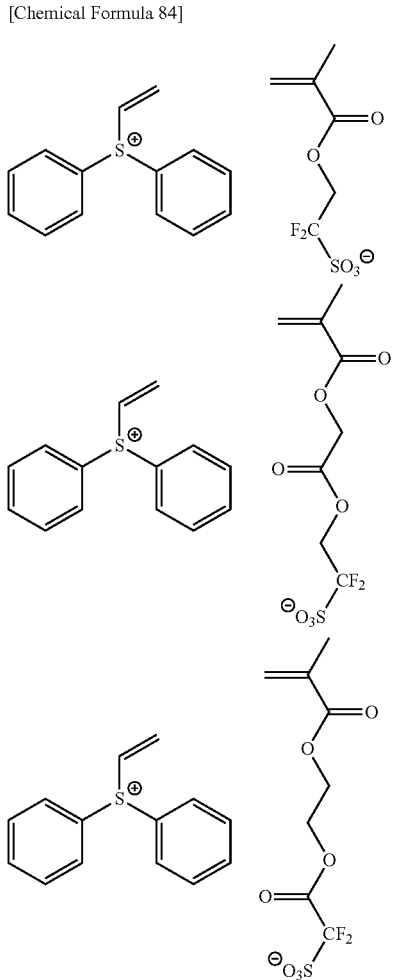

The compound (M1) may be produced, for example, by a method including a step (i) in which a precursor (M1-1) of a compound (M1) is obtained, and a step (ii) in which a compound (M1) is obtained from the precursor (M1-1).

Step (i) in which Precursor (M1-1) of Compound (M1) is Obtained:

The reaction of obtaining the precursor (M1-1) may be conducted in the absence of a solvent, or in an organic solvent (a typical solvent used in Grignard reaction, such as tetrahydrofuran, chloroform or dichloromethane) if desired. The reaction temperature depends on the boiling point of the solvent used, but is about −20 to 150° C. The reaction time is about 1 hour to several tens of hours.

Examples of the method of obtaining the precursor (M1-1) include 1) a method using a Grignard reagent, 2) a method using a Lewis acid, 3) a method using diphosphorus pentoxide, 4) a method using an iodonium salt, and 5) a method using a nucleophilic substitution reaction.

Specific examples of the methods 1) to 5) are shown below.

In the method 5), the reaction formula in the case where the cation moiety in formula (M1) is "$(C_6H_5)(C_6H_5)S^+-CH_2-C_6H_5$" is shown.

[Chemical Formula 85]

1) Method using a Grignard reagent

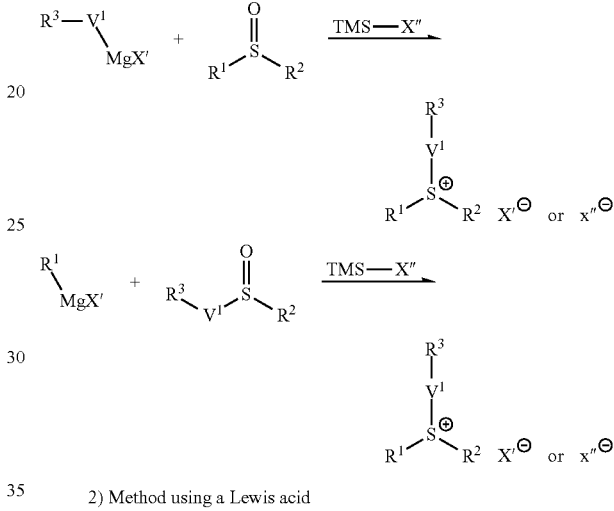

2) Method using a Lewis acid

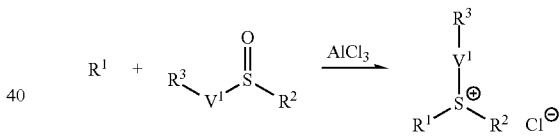

3) Method using a diphosphorus pentoxide

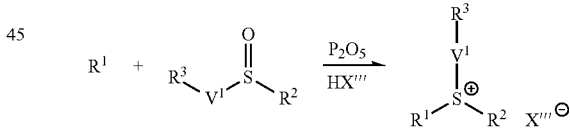

4) Method using a iodonium salt

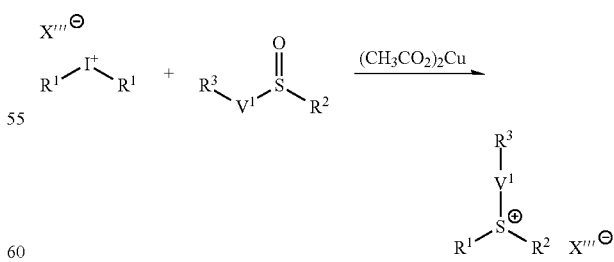

5) Method using a nucleophilic substitution reaction

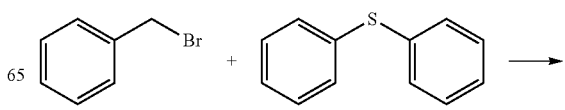

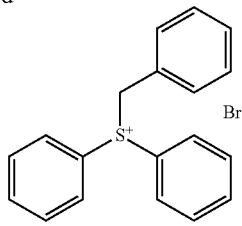

In the reaction formulae, $R^1$, $R^2$, $R^3$ and $V^1$ are the same as defined for $R^1$, $R^2$, $R^3$ and $V^1$ in the aforementioned formula (m0).

X' represents a halogen atom. X" is not particularly limited as long as it serves as an anion, and Cl, Br, $CF_3SO_3$ or an organic anion is preferable.

In the formula TMS-X", TMS represents a trimethylsilyl group.

X''' is not particularly limited, but is preferably a halogen atom.

Step (ii) in which Compound (M1) is Obtained from Precursor (M1-1):

The operation of the step (ii) may be conducted following the reaction of step (i) or after separation (and purification, if desired) of the precursor (M1-1).

In step (ii), the precursor (M1-1) and an aqueous solution of the salt ($M^+X^-$) are mixed together and stirred to effect a double decomposition reaction. Then, the precipitated solid is separated by filtration, or the separated oily substance is extracted with an organic solvent to remove the organic solvent, thereby obtaining the compound (M1) in the form of a solid or a viscous liquid.

The obtained solid or viscous liquid may be washed with an appropriate organic solvent, or purified by recrystallization or column chromatography.

Alternatively, in the method 1), when X'''$^-$ is X$^-$, a compound (M1) can be obtained without conducting the double decomposition reaction.

The chemical structure of the compound (M1) can be identified by a general analytical method (e.g., $^1H-$, $^{11}B-$, $^{13}C-$, $^{19}F-$, $^{31}P$-nuclear magnetic resonance spectroscopy, infrared spectroscopy and/or elemental analysis).

The compound (M1) is useful as a component which generates acid upon exposure in a resist composition.

Examples of the compound (M1) which generates a strong acid upon exposure include a compound in which X$^-$ in formula (M1) is the anion moiety of a compound represented by any one of formulae (b-1) to (b-3), and a compound having an organic anion represented by any one of formulae (am0-1-1) to (am0-1-3). These compounds may be used as the aforementioned acid generator component (component (B)).

Examples of the compound (M1) which generates a weak acid upon exposure include a compound in which X$^-$ in formula (M1) is the anion moiety of a compound represented by any one of formulae (d1-1) to (d1-3), and a compound having an organic anion represented by any one of formulae (am0-2-1) to (am0-2-3). These compounds may be used as the aforementioned acid diffusion control agent (component (D)).

<<Polymeric Compound>>

A third aspect of the present invention is a polymeric compound including an anion group which generates acid upon exposure on a side chain of the polymeric compound, and a structural unit (am0) having a cation moiety containing a cation represented by general formula (m1) shown below.

[Chemical Formula 86]

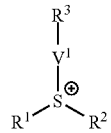

(m1)

In formula (m1), $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group.

The structural unit (am0) is the same as defined for the structural unit (am0) described above in relation to the third resist composition. Preferable examples of the structural unit (am0) include a structural unit derived from the compound (am0-1), and a structural unit derived from the compound (am0-2).

Preferable examples of the polymeric compound according to the present embodiment include the component (A12-1) described above in relation to the third resist composition.

The polymeric compound of the present embodiment can be obtained, for example, by a conventional radical polymerization or the like of a monomer for deriving the structural unit (am0) (e.g., a compound (am0-1), a compound (am0-2) or the like) and a monomer for deriving any other structural unit (any of structural units (a1) to (a4) and the like) if desired, using a radical polymerization initiator such as azobisisobutyronitrile (AIBN).

<<Method of Forming a Resist Pattern>>

The method of forming a resist pattern according to the fourth aspect of the present invention includes: using a resist composition according to the first aspect of the present invention to form a resist film on a substrate; exposing the resist film; and developing the exposed resist film to form a resist pattern.

The method for forming a resist pattern according to the present embodiment can be performed, for example, as follows.

Firstly, a resist composition of the present embodiment is applied to a substrate using a spinner or the like, and a bake treatment (post applied bake (PAB)) is conducted at a temperature of 80 to 150° C. for 40 to 120 seconds, preferably 60 to 90 seconds, to form a resist film.

Subsequently, the resist film is selectively exposed, either by exposure through a mask having a predetermined pattern formed thereon (mask pattern) using an exposure apparatus such as an ArF exposure apparatus, an electron beam lithography apparatus or an EUV exposure apparatus, or by patterning via direct irradiation with an electron beam without using a mask pattern.

Then, baking treatment (post exposure baking (PEB)) is conducted under temperature conditions of 80 to 150° C. for 40 to 120 seconds, and preferably 60 to 90 seconds.

Next, the resist film which has been subjected to the selective exposure and the baking treatment is subjected to a developing treatment. The developing treatment is conducted using an alkali developing solution in the case of an alkali developing process, and a developing solution containing an organic solvent (organic developing solution) in the case of a solvent developing process.

After the developing treatment, it is preferable to conduct a rinse treatment. The rinse treatment is preferably conducted using pure water in the case of an alkali developing process, and a rinse solution containing an organic solvent in the case of a solvent developing process.

In the case of a solvent developing process, after the developing treatment or the rinsing, the developing solution or the rinse liquid remaining on the pattern can be removed by a treatment using a supercritical fluid.

After the developing treatment or the rinse treatment, drying is conducted. If desired, bake treatment (post bake) can be conducted following the developing treatment.

In this manner, a resist pattern can be formed.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present invention is effective to KrF excimer laser, ArF excimer laser, EB and EUV.

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

As an example of the alkali developing solution used in an alkali developing process, a 0.1 to 10% by weight aqueous solution of tetramethylammonium hydroxide (TMAH) can be given.

As the organic solvent contained in the organic developing solution used in a solvent developing process, any of the conventional organic solvents can be used which are capable of dissolving the base component of the resist composition (prior to exposure). Specific examples of the organic solvent include polar solvents such as ketone solvents, ester solvents, alcohol solvents, amide solvents and ether solvents, and hydrocarbon solvents.

If desired, the organic developing solution may have a conventional additive blended. Examples of the additive include surfactants. The surfactant is not particularly limited, and for example, an ionic or non-ionic fluorine and/or silicon surfactant can be used.

When a surfactant is added, the amount thereof based on the total amount of the organic developing solution is generally 0.001 to 5% by weight, preferably 0.005 to 2% by weight, and more preferably 0.01 to 0.5% by weight.

The developing treatment can be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

The rinse treatment using a rinse liquid (washing treatment) can be conducted by a conventional rinse method. Examples of the rinse method include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

EXAMPLES

As follows is a description of examples of the present invention, although the scope of the present invention is by no way limited by these examples.

In the following examples, a compound represented by a chemical formula (1) is designated as "compound (1)", and the same applies for compounds represented by other chemical formulae.

<Production of Compound>

Example 1

Compound (2)

1 g of compound (2-1) was dissolved in 5 g of dichloromethane, and 5 g of water and 0.95 g of compound (2-2) were added thereto, followed by stirring for 30 minutes. Then, liquid separation was conducted with 5 g of water 3 times, so as to wash the organic solvent phase. The obtained organic solvent phase was dropwise added to 50 g of hexane over 60 minutes, followed by stirring for 30 minutes and filtration. The obtained powder was dried at room temperature for 12 hours, thereby obtaining 0.84 g of compound (2).

[Chemical Formula 87]

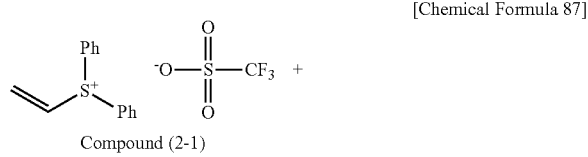

Compound (2-1)

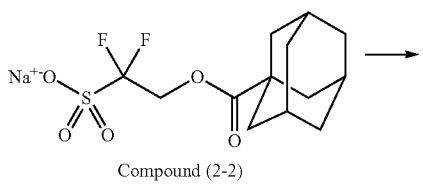

Compound (2-2)

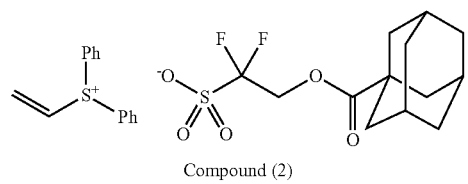

Compound (2)

Examples 2 to 19

Compounds (1) and (3) to (19)

Compounds (1) and (3) to (19) were obtained in the same manner as in Example 1, except that the anion moiety of compound (2-2) was changed to the corresponding anion.

Example 20

Compound (20)

Compound (20) was obtained in the same manner as in Example 1, except that the cation moiety of compound (2-1) was changed to the corresponding cation.

The structures of the obtained compounds (1) to (20) and the results of the $^1$H-NMR (400 MHz, DMSO-d6) analysis are shown in Tables 1 and 2.

TABLE 1

| Compound | Structure of cation moiety | Structure of anion moiety | $^1$H-NMR |
|---|---|---|---|
| (1) | Ph–S$^+$(Ph)–CH=CH$_2$ | (camphorsulfonate structure) | δ (ppm) = 8.00-7.70 (m, 10 H, Ar—H), 7.62 (dd, 1 H, vinyl), 6.82 (dd, 1 H, vinyl), 6.52 (dd, 1 H, vinyl), 2.88 (d, 1 H, CH), 2.66-2.74 (m, 1 H, CH), 2.37 (d, 1 H, CH), 2.17-2.24 (m, 1 H, CH), 1.90 (t, 1 H, CH), 1.74-1.89 (m, 2 H, CH2), 1.22-1.29 (m, 2 H, CH |
| (2) | Ph–S$^+$(Ph)–CH=CH$_2$ | (fluorinated sulfonate adamantyl ester) | δ (ppm) = 8.00-7.70 (m, 10 H, Ar—H), 7.62 (dd, 1H, vinyl), 6.82 (dd, 1 H, vinyl), 6.52 (dd, 1 H, vinyl), 4.55 (t, 2H, CH2), 1.64-1.96 (m, 15H, Adamantyl). |

TABLE 1-continued

| Compound | Structure of cation moiety | Structure of anion moiety | ¹H-NMR |
|---|---|---|---|
| (3) | Vinyl-S⁺(Ph)(Ph) | ⁻O₃S-CF₂-C(O)O-CH₂CH₂-O-C(O)-Adamantyl | δ (ppm) = 8.00-7.70 (m, 10 H, Ar—H), 7.62 (dd, 1 H, vinyl), 6.82 (dd, 1 H, vinyl), 6.52 (dd, 1 H, vinyl), 4.40 (t, 2H, CH2), 4.21 (t, 2H, CH2), 1.61-1.98 (m, 15H, Adamantyl) |
| (4) | Vinyl-S⁺(Ph)(Ph) | ⁻O₃S-CF₂-C(O)O-oxo-norbornane lactone | δ (ppm) = 8.00-7.70 (m, 10 H, Ar—H), 7.62 (dd, 1 H, vinyl), 6.82 (dd, 1 H, vinyl), 6.52 (dd, 1 H, vinyl), 5.46 (t, 1 H, oxo-norbornane), 4.97 (s, 1H, oxo-norbornane), 4.71(d, 1H, oxo-norbornane), 4.57 (d, 1H, oxo-norbornane), 2.69-2.73 (m, 1H, oxo-norborna |
| (5) | Vinyl-S⁺(Ph)(Ph) | ⁻O₃S-CF₂-C(O)O-norbornane sultone | δ (ppm) = 8.00-7.70 (m, 10 H, Ar—H), 7.62 (dd, 1H, vinyl), 6.82 (dd, 1 H, vinyl), 6.52 (dd, 1 H, vinyl), 4.78 (m, 1 H, CH), 4.66 (t, 1 H, CH), 3.88 (t, 1H, CH), 3.34 (m, 1H, CH), 2.47-2.49 (m, 1H, CH), 1.73-2.21 (m, 4H, CH2) |
| (6) | Vinyl-S⁺(Ph)(Ph) | ⁻O-C(O)-Me | δ (ppm) = 8.00-7.70 (m, 10 H, Ar—H), 7.62 (dd, 1 H, vinyl), 6.82 (dd, 1 H, vinyl), 6.52 (dd, 1 H, vinyl), 1.75 (s, 3 H) |
| (7) | Vinyl-S⁺(Ph)(Ph) | ⁻O-C(O)-Adamantyl | δ (ppm) = 8.00-7.70 (m, 10 H, Ar—H), 7.62 (dd, 1 H, vinyl), 6.82 (dd, 1 H, vinyl), 6.52 (dd, 1 H, vinyl), 1.90-1.50 (m, 15 H) |
| (8) | Vinyl-S⁺(Ph)(Ph) | 2-hydroxybenzoate (⁻O-C(O)-C₆H₄-OH) | δ (ppm) = 8.00-7.70 (m, 10 H, Ar—H), 7.62 (dd, 1H, vinyl), 7.65 (m, 1H, ArH), 7.10 (m, 1 H, ArH), 6.82 (dd, 1 H, vinyl), 6.56 (m, 2 H, ArH), 6.52 (dd, 1 H, vinyl). |
| (9) | Vinyl-S⁺(Ph)(Ph) | ⁻O-C(O)-CH₂-O-C(O)-Me | δ (ppm) = 8.00-7.70 (m, 10 H, Ar—H), 7.62 (dd, 1 H, vinyl), 6.82 (dd, 1 H, vinyl), 6.52 (dd, 2 H, vinyl), 4.43(s, 2H, CH2), 2.01 (s, 3H, CH3) |
| (10) | Vinyl-S⁺(Ph)(Ph) | ⁻O-C(O)-CH₂-O-Me | δ (ppm) = 8.00-7.70 (m, 10 H, Ar—H), 7.62 (dd, 1H, vinyl), 6.82 (dd, 1 H, vinyl), 6.52 (dd, 3 H, vinyl), 4.01 (s, 2 H, CH2), 3.23 (s, 3 H, CH3) |
| (11) | Vinyl-S⁺(Ph)(Ph) | ⁻O-C(O)-CH₂-O-C(O)-Adamantyl | δ (ppm) = 8.00-7.70 (m, 10 H, Ar—H), 7.62 (dd, 1 H, vinyl), 6.82 (dd, 1 H, vinyl), 6.52 (dd, 4 H, vinyl), 4.55 (s, 2 H, CH2), 1.68-1.98 (m, 15 H, Adamantyl) |

TABLE 2

| Compound | Structure of cation moiety | Structure of anion moiety | ¹H-NMR |
|---|---|---|---|
| (12) | Ph-S⁺(Ph)-CH=CH₂ | (camphor-sulfonate-glycolate ester structure) | δ (ppm) = 8.00-7.70 (m, 10 H, Ar—H), 7.62 (dd, 1 H, vinyl), 6.82 (dd, 1 H, vinyl), 6.52 (dd, 5 H, vinyl), 4.12 (s, 2 H, CH2), 2.31-2.43 (m, 1 H, CH), 1.87-2.02 (m, 2 H, CH2), 1.49-1.68 (m, 1 H, CH), 0.85-1.15 (m, 9 H, CH3 + CH3 + CH3) |
| (13) | Ph-S⁺(Ph)-CH=CH₂ | (sulfonate-acetate-butyrolactone ester) | δ (ppm) = 8.00-7.70 (m, 10 H, Ar—H), 7.62 (dd, 1 H, vinyl), 6.82 (dd, 1 H, vinyl), 6.52 (dd, 6 H, vinyl), 5.70 (t, 1 H, CH), 4.46-4.30 (m, 2 H, CH2), 3.50 (m, 2 H, CH2), 2.71-2.64 (m, 1 H, CH2), 2.33-2.24 (m, 1 H, CH2) |
| (14) | Ph-S⁺(Ph)-CH=CH₂ | (sulfonate-acetate-adamantyl ester) | δ (ppm) = 8.00-7.70 (m, 10 H, Ar—H), 7.62 (dd, 1H, vinyl), 6.82 (dd, 1 H, vinyl), 6.52 (dd, 7 H, vinyl), 4.80 (s, 1 H, Adamantyl), 3.80 (s, 2 H, CH2), 2.11 (d, 2 H, Adamantyl), 1.30-1.98 (m, 12 H, Adamantyl) |
| (15) | Ph-S⁺(Ph)-CH=CH₂ | (camphanic acid sulfonate ethyl ester) | δ (ppm) = 8.00-7.70 (m, 10 H, Ar—H), 7.62 (dd, 1 H, vinyl), 6.82 (dd, 1 H, vinyl), 6.52 (dd, 8 H, vinyl), 4.43 (t, 2 H, COOCH2), 2.81 (m, 2 H, Camphanic acid), 2.41 (m, 1 H, Camphanic acid), 1.98 (t, 2 H, CCH2SO3), 1.56 (m, 1 H, Camphanic acid), 0.79-1.10 |
| (16) | Ph-S⁺(Ph)-CH=CH₂ | F₃C-SO₂-N⁻-CH₂CH₂-O-C(O)-Adamantyl | δ (ppm) = 8.00-7.70 (m, 10 H, Ar—H), 7.62 (dd, 1H, vinyl), 6.82 (dd, 1 H, vinyl), 6.52 (dd, 1 H, vinyl), 3.82-3.89 (t, 2 H, CH2), 3.00-3.08 (t, 2 H, CH2), 1.58-1.93 (m, 15 H, Adamantyl) |
| (17) | Ph-S⁺(Ph)-CH=CH₂ | ⁻O₃S-CF₂-CH₂-O-C(O)-C(CH₃)=CH₂ | δ (ppm) = 8.00-7.70 (m, 10 H, Ar—H), 7.62 (dd, 1 H, vinyl), 6.82 (dd, 1 H, vinyl), 6.52 (dd, 9 H, vinyl), 6.12 (s, 1 H, CH), 5.65 (s, 1 H, CH), 4.53-4.69 (t, 2 H, CH2), 1.92 (s, 3 H, CH3) |
| (18) | Ph-S⁺(Ph)-CH=CH₂ | ⁻O₃S-CF₂-CH₂-O-C(O)-CH₂-O-C(O)-C(CH₃)=CH₂ | δ (ppm) = 8.00-7.70 (m, 10 H, Ar—H), 7.62 (dd, 1 H, vinyl), 6.82 (dd, 1 H, vinyl), 6.52 (dd, 10 H, vinyl), 6.12 (s, 1 H, CH), 5.78 (s, 1 H, CH), 4.85 (s, 1 H, CH), 4.53-4.68 (t, 2 H, CH2), 1.92 (s, 3 H, CH3) |
| (19) | Ph-S⁺(Ph)-CH=CH₂ | ⁻O₃S-CF₂-C(O)-O-CH₂CH₂-O-C(O)-C(CH₃)=CH₂ | δ (ppm) = 8.00-7.70 (m, 10 H, Ar—H), 7.62 (dd, 1H, vinyl), 6.82 (dd, 1 H, vinyl), 6.52 (dd, 11 H, vinyl), 6.05 (s, 1 H, CH), 5.65 (s, 1 H, CH), 4.49-4.52 (t, 2 H, CH2), 4.28-4.32 (t, 2 H, CH2), 1.86 (s, 3 H, CH3) |

TABLE 2-continued

| Compound | Structure of cation moiety | Structure of anion moiety | ¹H-NMR |
|---|---|---|---|
| (20) | Benzyl diphenyl sulfonium (Ph-CH2-S+(Ph)2) | -O3S-CF2-CH2-O-C(=O)-Adamantyl | δ (ppm) = 7.50-7.20 (m, 15 H, Ar—H), 5.31 (s, 2 H, Ph—CH2—), 4.55 (t, 2H, CH2), 1.64-1.96 (m, 15H, Adamantyl). |

<Production of Resist Composition>

Examples 21 to 31, Comparative Examples 1 to 8

The components shown in Tables 3 to 6 were mixed together and dissolved to obtain each resist composition.

TABLE 3

| | Component (A) | Component (B) | Component (D) | Component (E) | Component (F) | Component (S) | |
|---|---|---|---|---|---|---|---|
| Comp. Ex. 1 | (A)-1 [100] | (B)-1 [14.50] | (D)-1 [5.15] | (E)-1 [0.20] | (F)-1 [4.0] | (S)-1 [100] | (S)-2 [3300] |
| Comp. Ex. 2 | (A)-1 [100] | (B)-2 [14.20] | (D)-1 [5.15] | (E)-1 [0.20] | (F)-1 [4.0] | (S)-1 [100] | (S)-2 [3300] |
| Comp. Ex. 3 | (A)-1 [100] | (B)-3 [14.74] | (D)-1 [5.15] | (E)-1 [0.20] | (F)-1 [4.0] | (S)-1 [100] | (S)-2 [3300] |
| Example 21 | (A)-1 [100] | (B)-4 [12.95] | (D)-1 [5.15] | (E)-1 [0.20] | (F)-1 [4.0] | (S)-1 [100] | (S)-2 [3300] |
| Example 22 | (A)-1 [100] | (B)-5 [13.95] | (D)-1 [5.15] | (E)-1 [0.20] | (F)-1 [4.0] | (S)-1 [100] | (S)-2 [3300] |
| Example 23 | (A)-1 [100] | (B)-6 [14.55] | (D)-1 [5.15] | (E)-1 [0.20] | (F)-1 [4.0] | (S)-1 [100] | (S)-2 [3300] |

TABLE 4

| | Component (A) | Component (B) | Component (D) | Component (E) | Component (F) | Component (S) | |
|---|---|---|---|---|---|---|---|
| Comp. Ex. 4 | (A)-1 [100] | (B)-2 [14.20] | (D)-1 [14.20] | (E)-1 [0.20] | (F)-1 [4.0] | (S)-1 [100] | (S)-2 [3300] |
| Example 24 | (A)-1 [100] | (B)-2 [14.20] | (D)-2 [13.13] | (E)-1 [0.20] | (F)-1 [4.0] | (S)-1 [100] | (S)-2 [3300] |
| Example 25 | (A)-1 [100] | (B)-4 [12.95] | (D)-2 [13.13] | (E)-1 [0.20] | (F)-1 [4.0] | (S)-1 [100] | (S)-2 [3300] |
| Example 26 | (A)-1 [100] | (B)-2 [14.20] | (D)-3 [11.04] | (E)-1 [0.20] | (F)-1 [4.0] | (S)-1 [100] | (S)-2 [3300] |
| Example 27 | (A)-1 [100] | (B)-3 [14.74] | (D)-4 [12.37] | (E)-1 [0.20] | (F)-1 [4.0] | (S)-1 [100] | (S)-2 [3300] |
| Example 28 | (A)-1 [100] | (B)-3 [14.74] | (D)-5 [16.34] | (E)-1 [0.20] | (F)-1 [4.0] | (S)-1 [100] | (S)-2 [3300] |

TABLE 5

| | Component (A) | Component (B) | Component (D) | Component (E) | Component (F) | Component (S) | |
|---|---|---|---|---|---|---|---|
| Comp. Ex. 5 | (A)-2 [100] | (B)-1 [12.33] | (D)-1 [4.38] | (E)-1 [0.20] | (F)-1 [4.0] | (S)-1 [100] | (S)-2 [3300] |
| Comp. Ex. 6 | (A)-2 [100] | (B)-2 [12.07] | (D)-1 [4.38] | (E)-1 [0.20] | (F)-1 [4.0] | (S)-1 [100] | (S)-2 [3300] |
| Comp. Ex. 7 | (A)-2 [100] | (B)-3 [10.65] | (D)-1 [4.38] | (E)-1 [0.20] | (F)-1 [4.0] | (S)-1 [100] | (S)-2 [3300] |
| Example 29 | (A)-2 [100] | (B)-4 [9.36] | (D)-1 [4.38] | (E)-1 [0.20] | (F)-1 [4.0] | (S)-1 [100] | (S)-2 [3300] |
| Example 30 | (A)-2 [100] | (B)-5 [10.08] | (D)-1 [4.38] | (E)-1 [0.20] | (F)-1 [4.0] | (S)-1 [100] | (S)-2 [3300] |

TABLE 6

| | Component (A) | Component (D) | Component (E) | Component (F) | Component (S) | |
|---|---|---|---|---|---|---|
| Comp. Ex. 8 | (A)-3 [100] | (D)-1 [5.15] | (E)-1 [0.20] | (F)-1 [4.0] | (S)-1 [100] | (S)-2 [3300] |
| Example 31 | (A)-4 [100] | (D)-1 [5.15] | (E)-1 [0.20] | (F)-1 [4.0] | (S)-1 [100] | (S)-2 [3300] |

In Tables 3 to 6, the reference characters indicate the following. The values in brackets [ ] indicate the amount (in terms of parts by weight) of the component added.

(A)-1: Polymeric compound represented by chemical formula (A)-1 shown below. The weight average molecular weight (Mw) and the dispersity (Mw/Mn) in terms of the polystyrene equivalent value measured by gel permeation chromatography (GPC) were 7,000 and 1.71, respectively. The composition of the copolymer (ratio (molar ratio) of the respective structural units within the structural formula) as determined by $^{13}$C-NMR was l/m/n=45/35/20.

(A)-2: Polymeric compound represented by chemical formula (A)-2 shown below. The weight average molecular weight (Mw) and the dispersity (Mw/Mn) in terms of the polystyrene equivalent value measured by gel permeation chromatography (GPC) were 7,000 and 1.71, respectively. The composition of the copolymer (ratio (molar ratio) of the respective structural units within the structural formula) as determined by $^{13}$C-NMR was l/m/n=45/35/20.

[Chemical Formula 88]

(A)-1

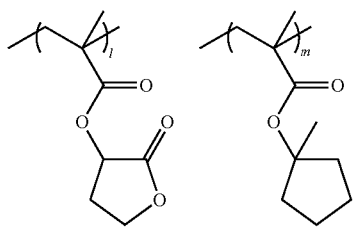

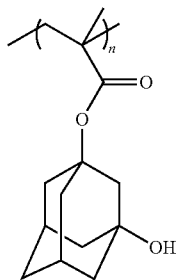

(A)-2

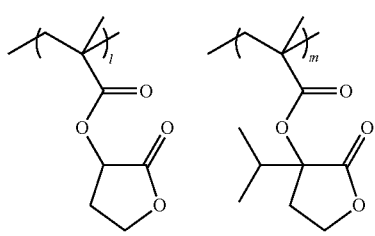

-continued

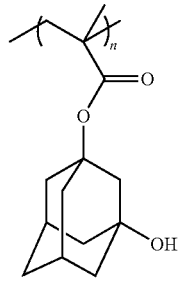

(A)-3: Polymeric compound represented by chemical formula (A)-3 shown below. The weight average molecular weight (Mw) and the dispersity (Mw/Mn) in terms of the polystyrene equivalent value measured by gel permeation chromatography (GPC) were 7,000 and 1.81, respectively. The composition of the copolymer (ratio (molar ratio) of the respective structural units within the structural formula) as determined by $^{13}$C-NMR was l/m/n/o=41/32/19/8.

(A)-4: Polymeric compound represented by chemical formula (A)-4 shown below. The weight average molecular weight (Mw) and the dispersity (Mw/Mn) in terms of the polystyrene equivalent value measured by gel permeation chromatography (GPC) were 7,000 and 1.81, respectively. The composition of the copolymer (ratio (molar ratio) of the respective structural units within the structural formula) as determined by $^{13}$C-NMR was l/m/n/o=41/32/19/8.

[Chemical Formula 89]

(A)-3

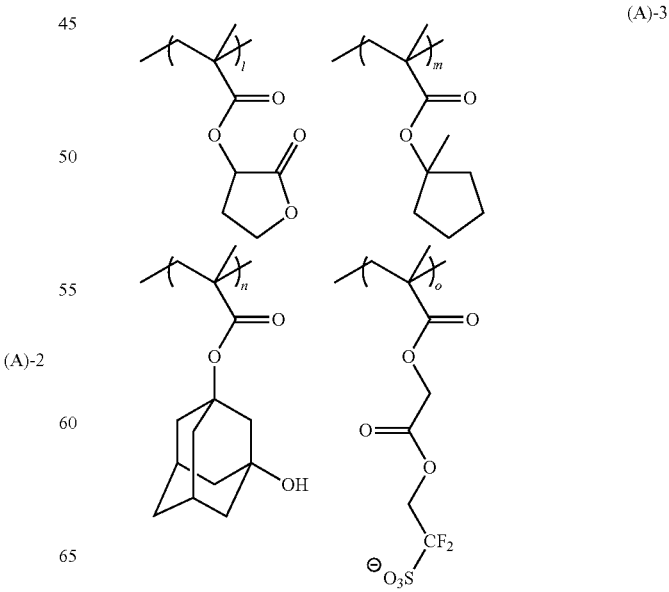

[Chemical Formula 90]

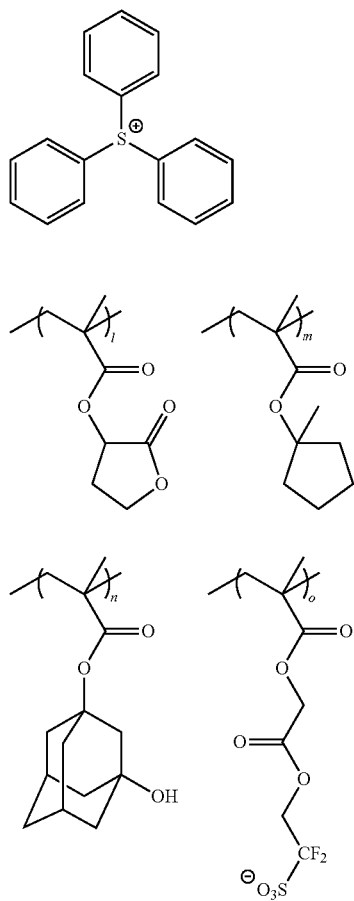

(A)-4

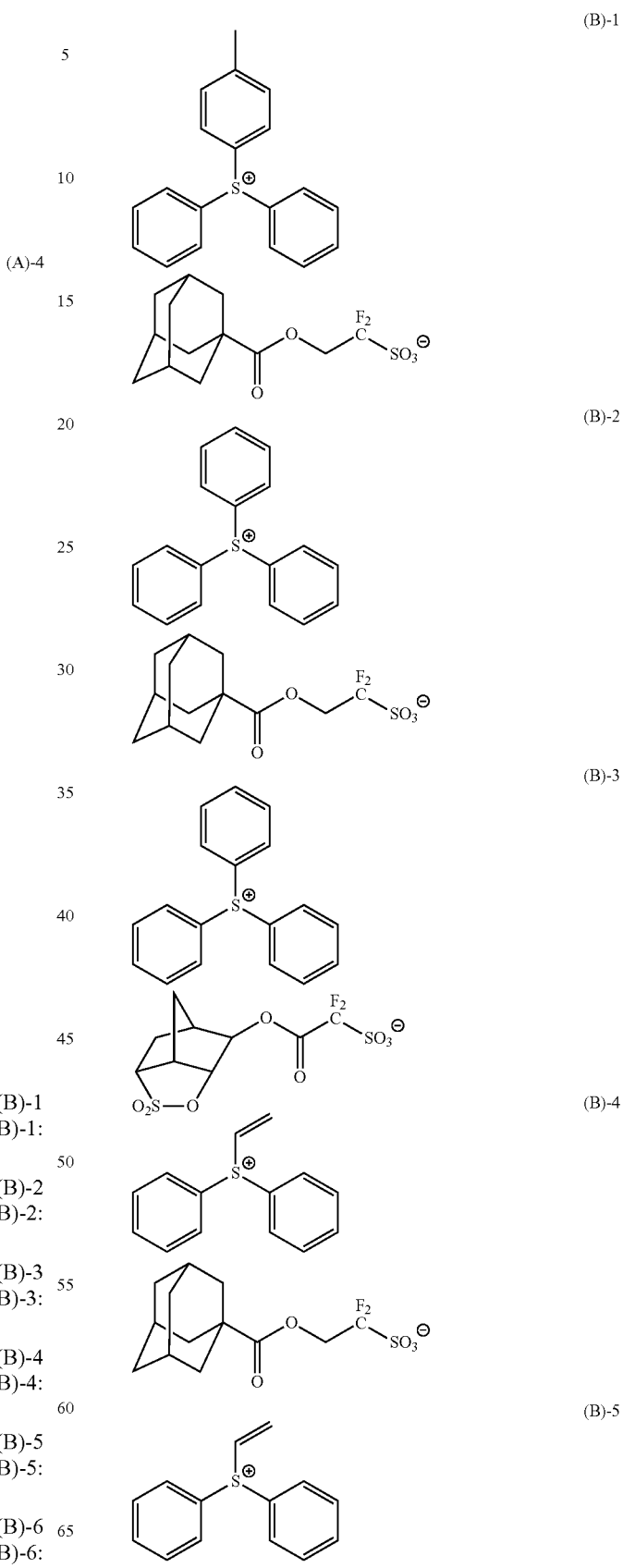

(B)-1: Compound represented by chemical formula (B)-1 shown below; pKa of acid generated from compound (B)-1: −2.70.

(B)-2: Compound represented by chemical formula (B)-2 shown below; pKa of acid generated from compound (B)-2: −2.70.

(B)-3: Compound represented by chemical formula (B)-3 shown below; pKa of acid generated from compound (B)-3: −3.39.

(B)-4: Compound represented by chemical formula (B)-4 shown below; pKa of acid generated from compound (B)-4: −2.70.

(B)-5: Compound represented by chemical formula (B)-5 shown below; pKa of acid generated from compound (B)-5: −3.39.

(B)-6: Compound represented by chemical formula (B)-6 shown below; pKa of acid generated from compound (B)-6: −2.70.

-continued

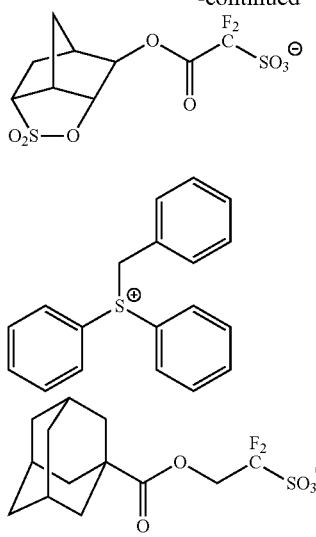

(D)-1: Compound represented by chemical formula (D)-1 shown below; pKa of acid generated from compound (D)-1: 1.17.

(D)-2: Compound represented by chemical formula (D)-2 shown below; pKa of acid generated from compound (D)-2: 1.17.

(D)-3: Compound represented by chemical formula (D)-3 shown below; pKa of acid generated from compound (D)-3: 3.01.

(D)-4: Compound represented by chemical formula (D)-4 shown below; pKa of acid generated from compound (D)-4: 4.86.

(D)-5: Compound represented by chemical formula (D)-5 shown below; pKa of acid generated from compound (D)-5: 1.44.

[Chemical Formula 91]

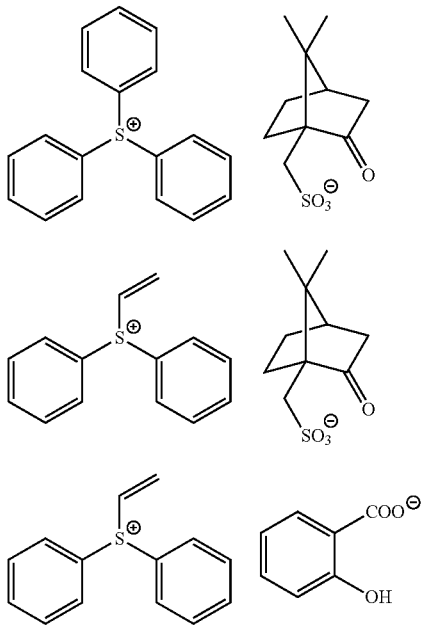

-continued

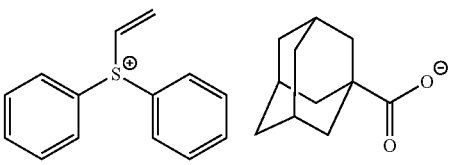

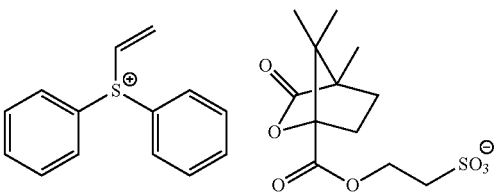

(E)-1: salicylic acid (F)-1: fluorine-containing polymeric compound represented by chemical formula (F)-1 below. The weight average molecular weight (Mw) and the dispersity (Mw/Mn) in terms of the polystyrene equivalent value measured by gel permeation chromatography (GPC) were 23,100 and 1.78, respectively. The composition of the copolymer (ratio (molar ratio) of the respective structural units within the structural formula) as determined by $^{13}$C-NMR was l/m=77/23.

[Chemical Formula 92]

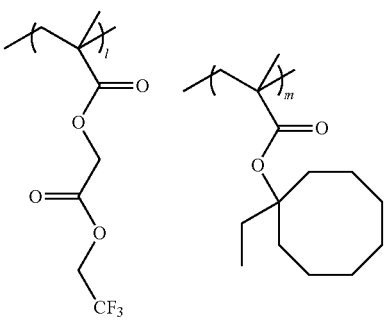

(S)-1: γ-butyrolactone (S)-2: a mixed solvent of PGMEA/PGME/cyclohexanone=45/30/25 (weight ratio)

<Formation of Resist Pattern (1)>

An organic anti-reflection film composition (product name: ARC95, manufactured by Brewer Science Ltd.) was applied to an 12-inch silicon wafer using a spinner, and the composition was then baked at 205° C. for 60 seconds and dried, thereby forming an organic anti-reflection film having a film thickness of 90 nm.

Then, each of the resist compositions indicated in Tables 3, 4 and 6 was applied to the organic antireflection film, and was then prebaked (PAB) on a hotplate at 110° C. for 60 seconds and dried, thereby forming a resist film having a film thickness of 90 nm.

Subsequently, the resist film was selectively irradiated with an ArF excimer laser (193 nm) through a mask, using an immersion lithography ArF exposure apparatus NSR-5609B (manufactured by Nikon Corporation; NA (numerical aperture)=1.07; Dipole 0.97/0.78 w/P; immersion medium: water).

Then, a post exposure bake (PEB) treatment was conducted at 95° C. for 60 seconds.

Thereafter, alkali developing was conducted for 10 seconds at 23° C. in a 2.38% by weight aqueous solution of tetramethylammonium hydroxide (TMAH) (product name: NMD-3; manufactured by Tokyo Ohka Kogyo Co., Ltd.).

As a result, in each of the examples, a line and space pattern having a line width of 50 nm and a pitch of 100 nm was formed.

[Evaluation of Optimum Exposure Dose (Eop)]

The optimum exposure dose Eop (mJ/cm$^2$) with which a line and space pattern having a target size (line width of 50 nm and pitch of 100 nm) was formed in the "Formation of resist pattern (1)" was determined. The results are indicated under "Eop (mJ/cm$^2$)" in Tables 7 to 9.

[Evaluation of Exposure Latitude (EL Margin)]

In the "Formation of resist pattern (1)", the exposure dose with which a line and space pattern having a line width of about ±5% of the target dimension (line width of 50 nm) was determined, and the EL margin (unit: %) was determined by the following formula. The results are indicated "5% EL (%)" in Tables 7 to 9.

EL margin(%)=(|E1−E2|/Eop)×100

E1: Exposure dose (mJ/cm$^2$) with which a line and space pattern having a line width of 47.5 nm was formed E2: Exposure dose (mJ/cm$^2$) with which a line and space pattern having a line width of 52.5 nm was formed The larger the value of the "EL margin", the smaller the change in the pattern size by the variation of the exposure dose.

[Evaluation of Line Width Roughness (LWR)]

With respect to each of the line and space patterns formed in the "Formation of resist pattern (1)" having a line width of 50 nm and a pitch of 100 nm, the line width at 400 points in the lengthwise direction of the line were measured using a measuring scanning electron microscope (SEM) (product name: S-9380, manufactured by Hitachi High-Technologies Corporation; acceleration voltage: 300V). From the results, the value of 3 times the standard deviation s (i.e., 3s) was determined, and the average of the 3s values at 400 points was calculated as a yardstick of LWR. The results are indicated under "LWR (nm)" in Tables 7 to 9.

The smaller this 3s value is, the lower the level of roughness of the line width, indicating that a line and space pattern with a uniform width was obtained.

[Evaluation of Mask Error Factor (MEEF)]

In accordance with the same procedure as in the "Formation of resist pattern (1)", a line and space pattern having a pitch of 100 nm was formed with the same exposure dose and using a mask pattern in which the target size of the line width was 45 to 55 nm (11 target sizes at intervals of 1 nm).

The value of the mask error factor was determined as the gradient of a graph obtained by plotting the target size (nm) on the horizontal axis, and the line width (nm) of the pattern formed on the resist film using each mask pattern on the vertical axis. The results are indicated under "MEEF" in Tables 7 to 9.

A MEEF value (gradient of the plotted line) closer to 1 indicates that a resist pattern faithful to the mask pattern was formed.

TABLE 7

|  | Eop (mJ/cm$^2$) | 5% EL (%) | LWR (nm) | MEEF |
|---|---|---|---|---|
| Comp. Ex. 1 | 26.80 | 7.32 | 2.91 | 1.78 |
| Comp. Ex. 2 | 25.30 | 7.73 | 2.63 | 1.87 |
| Comp. Ex. 3 | 28.20 | 7.91 | 2.58 | 1.72 |
| Example 21 | 20.12 | 8.92 | 2.21 | 1.58 |
| Example 22 | 21.32 | 9.02 | 2.18 | 1.51 |
| Example 23 | 21.59 | 8.85 | 2.32 | 1.65 |

TABLE 8

|  | Eop (mJ/cm$^2$) | 5% EL (%) | LWR (nm) | MEEF |
|---|---|---|---|---|
| Comp. Ex. 4 | 25.3 | 7.73 | 2.63 | 1.87 |
| Example 24 | 23.1 | 8.16 | 2.51 | 1.79 |
| Example 25 | 19.8 | 8.56 | 2.21 | 1.63 |
| Example 26 | 23.5 | 8.67 | 2.36 | 1.59 |
| Example 27 | 23.8 | 8.72 | 2.18 | 1.54 |
| Example 28 | 22.1 | 8.53 | 2.25 | 1.62 |

TABLE 9

|  | Eop (mJ/cm$^2$) | 5% EL (%) | LWR (nm) | MEEF |
|---|---|---|---|---|
| Comp. Ex. 8 | 30.2 | 8.32 | 2.32 | 1.48 |
| Example 31 | 28.3 | 8.45 | 2.25 | 1.41 |

From the results shown in Tables 7 to 9, it was confirmed that, according to the resist composition of the present invention, various lithography properties were excellent, and a resist pattern with an excellent shape could be formed.

<Formation of Resist Pattern (2)>

An organic anti-reflection film composition ARC-95 (product name; manufactured by Brewer Science Ltd.) and an organic anti-reflection film composition ARC-212 (product name; manufactured by Brewer Science Ltd.) were applied to a 12-inch silicon wafer using a spinner, and the compositions were then baked at 205° C. for 60 seconds and dried, thereby forming an organic anti-reflection film in which an anti-reflection film of "ARC-212" with a film thickness of 14 nm was laminated on an anti-reflection film of "ARC-95" with a film thickness of 72 nm.

Then, each of the resist compositions indicated in Table 5 was applied to the organic antireflection film, and was then prebaked (PAB) on a hotplate at 110° C. for 50 seconds and dried, thereby forming a resist film having a film thickness of 85 nm.

Subsequently, the resist film was selectively irradiated with an ArF excimer laser (193 nm) through a mask, using an immersion lithography ArF exposure apparatus NSR-5609B (manufactured by Nikon Corporation; NA (numerical aperture)=1.07; Annular 0.78/0.97 w/o P; immersion medium: water).

Then, a post exposure bake (PEB) treatment was conducted at 90° C. for 50 seconds.

Next, a solvent development was conducted at 23° C. for 31 seconds using butyl acetate, followed by drying by shaking.

As a result, in each of the examples, a space and line pattern (hereafter, referred to as "SL pattern") having a space width of 47 nm and a pitch of 110 nm was formed.

[Evaluation of Optimum Exposure Dose (Eop)]

The optimum exposure dose Eop (mJ/cm$^2$) with which an SL pattern having a target size (line width of 47 nm and pitch of 110 nm) was formed in the "Formation of resist pattern (2)" was determined. The results are indicated under "Eop (mJ/cm²)" in Table 10.

[Evaluation of Exposure Latitude (EL Margin)]

In the "Formation of resist pattern (2)", the exposure dose with which a space and line pattern having a space width of about ±5% of the target dimension (space width of 47 nm) was determined, and the EL margin (unit: %) was determined by the following formula. The results are indicated "5% EL (%)" in Table 10.

EL margin(%)=(|E3−E4|/Eop)×100

E3: Exposure dose (mJ/cm²) with which an SL pattern having a space width of 44.5 nm was formed E4: Exposure dose (mJ/cm²) with which an SL pattern having a space width of 49.5 nm was formed

[Evaluation of Line Width Roughness (LWR)]

With respect to each of the SL patterns formed in the "Formation of resist pattern (2)" having a space width of 47 nm and a pitch of 110 nm, the space width at 400 points in the lengthwise direction of the space were measured using a measuring scanning electron microscope (SEM) (product name: S-9380, manufactured by Hitachi High-Technologies Corporation; acceleration voltage: 300V). From the results, the value of 3 times the standard deviation s (i.e., 3s) was determined, and the average of the 3s values at 400 points was calculated as a yardstick of LWR. The results are indicated under "LWR (nm)" in Table 10.

[Evaluation of Mask Error Factor (MEEF)]

In accordance with the same procedure as in the "Formation of resist pattern (2)", an SL pattern having a pitch of 110 nm was formed with the same exposure dose and using a mask pattern in which the target size of the space width was 43 to 52 nm (10 target sizes at intervals of 1 nm).

The value of the mask error factor was determined as the gradient of a graph obtained by plotting the target size (nm) on the horizontal axis, and the space width (nm) of the pattern formed on the resist film using each mask pattern on the vertical axis. The results are indicated under "MEEF" in Table 10.

TABLE 10

|  | Eop (mJ/cm²) | 5% EL (%) | LWR (nm) | MEEF |
|---|---|---|---|---|
| Comp. Ex. 5 | 18.2 | 3.32 | 2.82 | 2.32 |
| Comp. Ex. 6 | 17.5 | 3.56 | 2.91 | 2.35 |
| Comp. Ex. 7 | 19.1 | 3.61 | 2.93 | 2.52 |
| Example 29 | 15.4 | 4.69 | 2.32 | 2.12 |
| Example 30 | 16.2 | 5.12 | 2.43 | 1.98 |

From the results shown in Table 10, it was confirmed that, according to the resist composition of the present invention, various lithography properties were excellent, and a resist pattern with an excellent shape could be formed.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition comprising:
a base component (A) which exhibits changed solubility in a developing solution under action of acid, and
an acid-generator component (B) which generates acid upon exposure,
the acid-generator component (B) comprising a compound represented by general formula (b0) shown below:

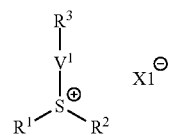

(b0)

wherein $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an alkenyl group which may have a substituent, or an alkynyl group which may have a substituent; $V^1$ represents a single bond or an alkylene group; and $X1^-$ represents an anion represented by any one of general formulae (an-1), (an-2), (an-3), (b'-2) or (b'-3) shown below:

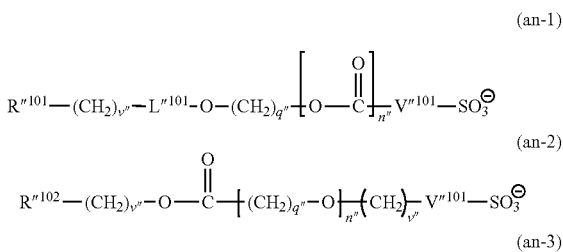

wherein $R''^{101}$ represents an aliphatic cyclic group which may have a substituent, a group represented by any one of formulae (r-hr-1) to (r-hr-6) shown below or a chain-like alkyl group which may have a substituent; $R''^{102}$ represents an aliphatic cyclic group which may have a substituent, a lactone-containing cyclic group represented by any one of general formulae (a2-r -1) to (a2-r-7) shown below or an —SO₂—containing cyclic group represented by any one of general formulae (a5-r-1) to (a5-r-4) shown below; $R'''^{103}$ represents an aromatic cyclic group which may have a substituent, an aliphatic cyclic group which may have a substituent or a chain-like alkenyl group which may have a substituent; $V'''^{101}$ represents a fluorinated alkylene group; $L''^{101}$ represents —C(=O)—or —SO₂—; v" represents an integer of 0 to 3; q" represents an integer of 1 to 20; and n" represents 0 or 1:

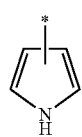

(r-hr-1)

-continued

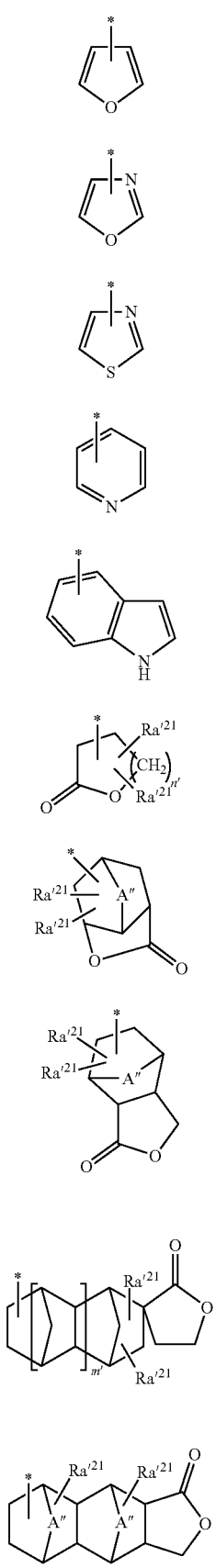

(r-hr-2)
(r-hr-3)
(r-hr-4)
(r-hr-5)
(r-hr-6)
(a2-r-1)
(a2-r-2)
(a2-r-3)
(a2-r-4)
(a2-r-5)

-continued

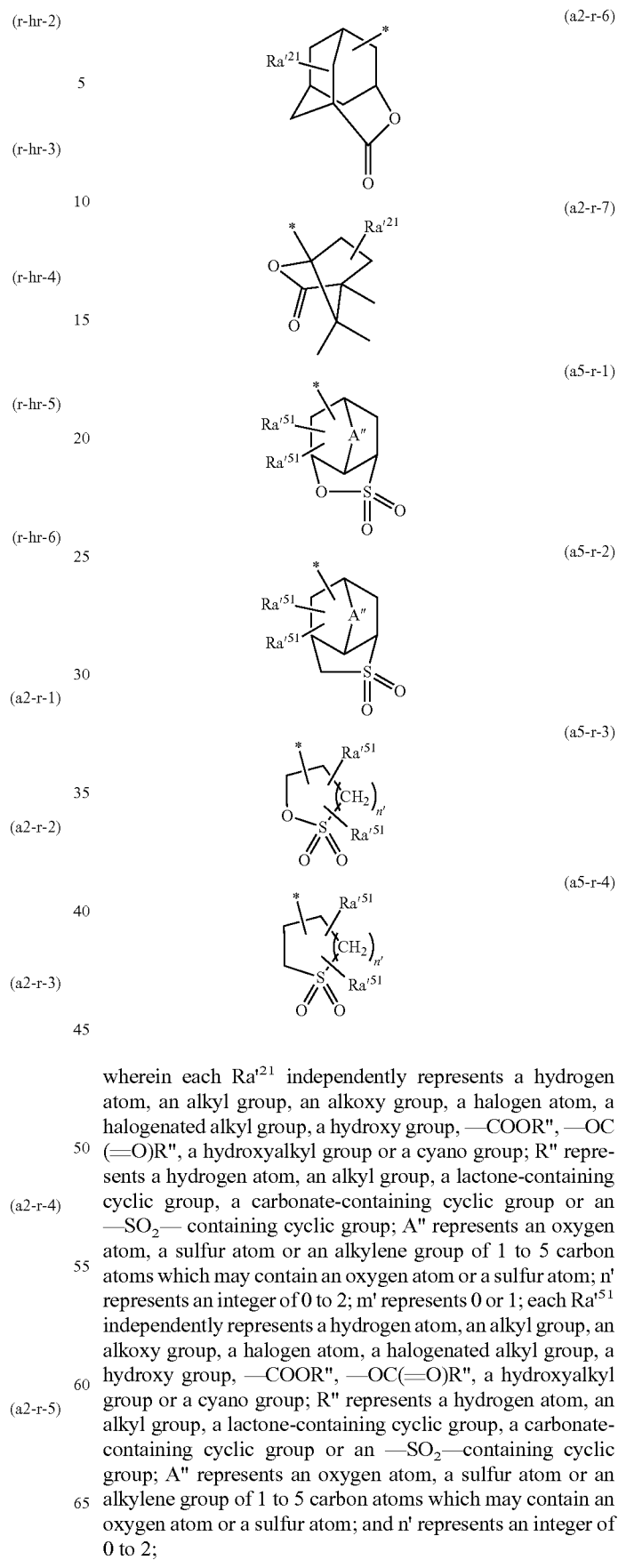

(a2-r-6)
(a2-r-7)
(a5-r-1)
(a5-r-2)
(a5-r-3)
(a5-r-4)

wherein each $Ra'^{21}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom, a sulfur atom or an alkylene group of 1 to 5 carbon atoms which may contain an oxygen atom or a sulfur atom; n' represents an integer of 0 to 2; m' represents 0 or 1; each $Ra'^{51}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —SO$_2$—containing cyclic group; A" represents an oxygen atom, a sulfur atom or an alkylene group of 1 to 5 carbon atoms which may contain an oxygen atom or a sulfur atom; and n' represents an integer of 0 to 2;

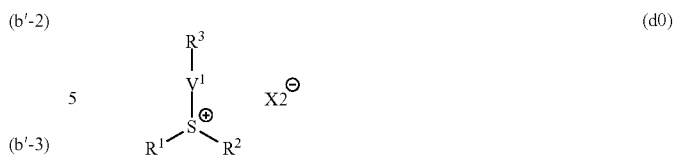

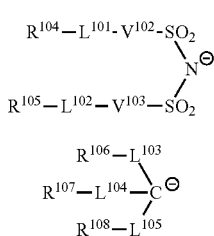

$R^{101}$ and $R^{104}$ to $R^{108}$ each independently represents a cyclic group which may have a substituent, a chain-like alkyl group which may have a substituent or a chain-like alkenyl group which may have a substituent, provided that $R^{104}$ and $R^{105}$ may be mutually bonded to form a ring; $R^{106}$ to $R^{108}$ may be mutually bonded to form a ring; $R^{102}$ represents a fluorine atom or a fluorinated alkyl group of 1 to 5 carbon atoms; $Y^{101}$ represents a single bond or a divalent linking group containing an oxygen atom; $V^{101}$ to $V^{103}$ each independently represents a single bond, an alkylene group, a fluorinated alkylene group, an arylene group or a fluorinated arylene group; $L^{101}$ and $L^{102}$ each independently represents a single bond or an oxygen atom; $L^{103}$ to $L^{105}$ each independently represents a single bond, —CO— or —SO$_2$—; and m represents an integer of 1 or more.

2. The resist composition according to claim 1, further comprising an acid diffusion control agent (D).

3. The resist composition according to claim 2, wherein the acid diffusion control agent (D) comprises a compound represented by general formula (d0) shown below:

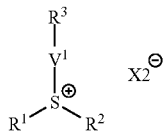

wherein $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group; and X2$^-$ represents a monovalent organic anion capable of generating a weak acid.

4. A method of forming a resist pattern, comprising:
   using a resist composition of claim 1 to form a resist film on a substrate,
   exposing the resist film, and
   developing the exposed resist film to form a resist pattern.

5. A resist composition which generates acid upon exposure and exhibits changed solubility in a developing solution under action of acid,
   the resist composition comprising an acid diffusion control agent (D) comprising a compound represented by general formula (d0) shown below:

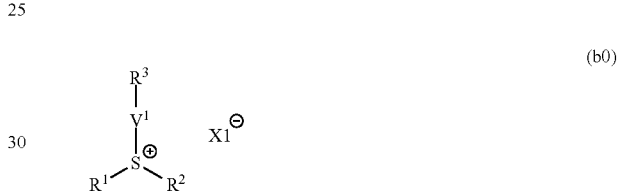

wherein $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an alkenyl group which may have a substituent, or an alkynyl group which may have a substituent; $V^1$ represents a single bond or an alkylene group; and X2$^-$ represents a monovalent organic anion capable of generating a weak acid.

6. The resist composition according to claim 5, further comprising an acid-generator component (B) which generates acid upon exposure.

7. The resist composition according to claim 6, wherein the acid-generator component (B) comprises a compound represented by general formula (b0) shown below:

$$\begin{array}{c} R^3 \\ | \\ V^1 \\ | \\ R^1 - S^+ - R^2 \end{array} \quad X1^{\ominus} \qquad (b0)$$

wherein $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group; and X1$^-$ represents a monovalent organic anion capable of generating a strong acid.

8. The resist composition according to claim 5, wherein $R^1$ and $R^2$ each independently represents a phenyl group.

9. A method of forming a resist pattern, comprising:
   sing a resist composition of claim 5 to form a resist film on a substrate,
   exposing the resist film, and
   developing the exposed resist film to form a resist pattern.

10. An acid generator comprising a compound represented by general formula (M1) shown below:

wherein $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; R³ represents, an alkenyl group which may have a substituent, or an alkynyl group which may have a substituent; V¹ represents a single bond or an alkylene group; and X⁻ represents an anion represented by any one of general formulae (an-1), (an-2), (an-3), (b'-2) or (b'-3) shown below:

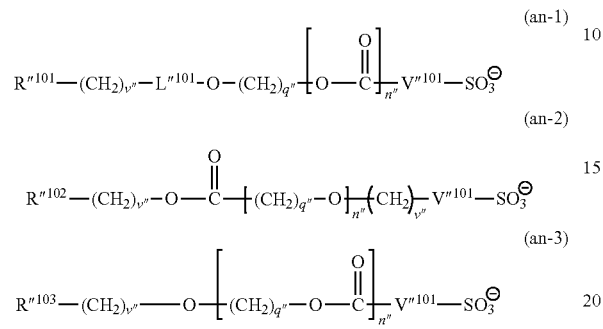

wherein $R''^{101}$ represents an aliphatic cyclic group which may have a substituent, a group represented by any one of formulae (r-hr-1) to (r-hr-6) shown below or a chain-like alkyl group which may have a substituent; $R''^{102}$ represents an aliphatic cyclic group which may have a substituent, a lactone-containing cyclic group represented by any one of general formulae (a2-r-1) to (a2-r-7) shown below or an —SO₂— containing cyclic group represented by any one of general formulae (a5-r-1) to (a5-r-4) shown below; $R''^{103}$ represents an aromatic cyclic group which may have a substituent, an aliphatic cyclic group which may have a substituent or a chain-like alkenyl group which may have a substituent; $V'''^{101}$ represents a fluorinated alkylene group; $L''^{101}$ represents —C(=O)— or —SO₂—; v" represents an integer of 0 to 3; q" represents an integer of 1 to 20; and n" represents 0 or 1:

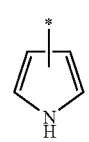
(r-hr-1)

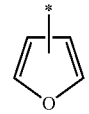
(r-hr-2)

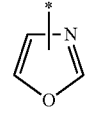
(r-hr-3)

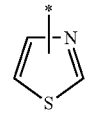
(r-hr-4)

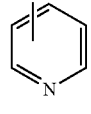
(r-hr-5)

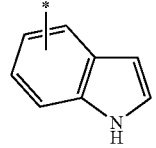
(r-hr-6)

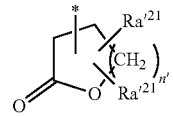
(a2-r-1)

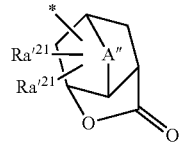
(a2-r-2)

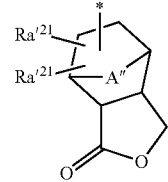
(a2-r-3)

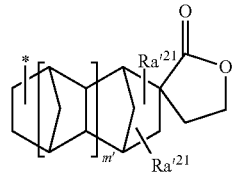
(a2-r-4)

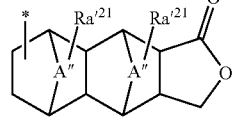
(a2-r-5)

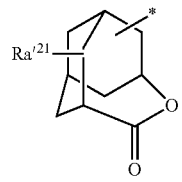
(a2-r-6)

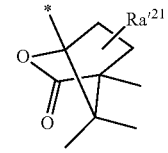
(a2-r-7)

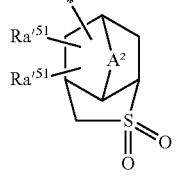
(a5-r-1)

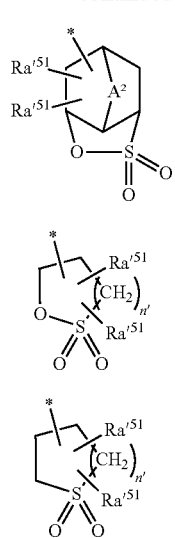

wherein each $Ra'^{21}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —SO$_2$—containing cyclic group; A" represents an oxygen atom, a sulfur atom or an alkylene group of 1 to 5 carbon atoms which may contain an oxygen atom or a sulfur atom; n' represents an integer of 0 to 2; m' represents 0 or 1; each $Ra'^{51}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —SO$_2$—containing cyclic group; A" represents an oxygen atom, a sulfur atom or an alkylene group of 1 to 5 carbon atoms which may contain an oxygen atom or a sulfur atom; and n' represents an integer of 0 to 2;

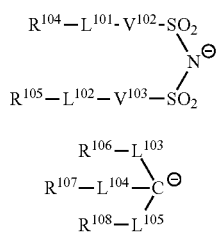

$R^{101}$ and $R^{104}$ each independently represents a cyclic group which may have a substituent, a chain-like alkyl group which may have a substituent or a chain-like alkenyl group which may have a substituent, provided that $R^{104}$ and $R^{105}$ may be mutually bonded to form a ring; $R^{106}$ to $R^{108}$ may be mutually bonded to form a ring; $R^{102}$ represents a fluorine atom or a fluorinated alkyl group of 1 to 5 carbon atoms; $Y^{101}$ represents a single bond or a divalent linking group containing an oxygen atom; $V^{101}$ to $V^{103}$ each independently represents a single bond, an alkylene group, a fluorinated alkylene group, an arylene group or a fluorinated arylene group; $L^{101}$ and $L^{102}$ each independently represents a single bond or an oxygen atom; $L^{103}$ to $L^{105}$ each independently represents a single bond, —CO— or —SO$_2$—; and m represents an integer of 1 or more.

11. A resist composition comprising a base component which exhibits changed solubility in a developing solution under action of acid and generates acid upon exposure, the base component comprising an anion group which generates acid upon exposure and a cation moiety comprising a cation represented by general formula (m1) shown below:

wherein $R^1$ and $R^2$ each independently represents a phenyl group; $R^3$ represents an alkenyl group which may have a substituent, or an alkynyl group which may have a substituent; $V^1$ represents a single bond or an alkylene group.

12. The resist composition according to claim 11, further comprising an acid-generator component (B) which generates acid upon exposure.

13. The resist composition according to claim 12, wherein the acid-generator component (B) comprises a compound represented by general formula (b0) shown below:

wherein $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group; and X1$^-$ represents a monovalent organic anion capable of generating a strong acid.

14. The resist composition according to claim 11, further comprising an acid diffusion control agent (D).

15. The resist composition according to claim 14, wherein the acid diffusion control agent (D) comprises a compound represented by general formula (d0) shown below:

wherein $R^1$ and $R^2$ each independently represents an aryl group which may have a substituent, an alkyl group which may have a substituent, or an alkenyl group which may have a substituent, provided that $R^1$ and $R^2$ may be mutually bonded to form a ring with the sulfur atom; $R^3$ represents an aromatic hydrocarbon group which may have a substituent, an alkenyl group which may have a substituent, or an alkynyl group which may have a substituent; $V^1$ represents a single bond or an alkylene group, provided that, when $R^3$ is an aromatic hydrocarbon group which may have a substituent, $V^1$ is an alkylene group; and $X2^-$ represents a monovalent organic anion capable of generating a weak acid.

16. A method of forming a resist pattern, comprising:
    using a resist composition of claim 11 to form a resist film on a substrate,
    exposing the resist film, and
    developing the exposed resist film to form a resist pattern.

17. A polymeric compound comprising:
    an anion group which generates acid upon exposure on a side chain of the polymeric compound, and
    a cation moiety comprising a cation represented by general formula (m1) shown below:

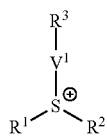

(m1)

wherein $R^1$ and $R^2$ each independently represents a phenyl group; $R^3$ represents an alkenyl group which may have a substituent, or an alkynyl group which may have a substituent; $V^1$ represents a single bond or an alkylene group.

* * * * *